US010627407B2

(12) United States Patent
Marshall et al.

(10) Patent No.: US 10,627,407 B2
(45) Date of Patent: Apr. 21, 2020

(54) ULTRA HIGH RESOLUTION MASS SPECTROMETRY AND METHODS OF USING THE SAME

(71) Applicant: MARS, INCORPORATED, McLean, VA (US)

(72) Inventors: James W. Marshall, Leicestershire (GB); Andrew J. Taylor, Leicestershire (GB)

(73) Assignee: MARS, INCORPORATED, McLean, VA (US)

(*) Notice: Subject to any disclaimer, the term of this patent is extended or adjusted under 35 U.S.C. 154(b) by 238 days.

(21) Appl. No.: 15/557,387

(22) PCT Filed: Mar. 11, 2016

(86) PCT No.: PCT/US2016/022149
§ 371 (c)(1),
(2) Date: Sep. 11, 2017

(87) PCT Pub. No.: WO2016/145390
PCT Pub. Date: Sep. 15, 2016

(65) Prior Publication Data
US 2018/0120327 A1    May 3, 2018

Related U.S. Application Data

(60) Provisional application No. 62/132,492, filed on Mar. 12, 2015, provisional application No. 62/269,897, filed on Dec. 18, 2015.

(51) Int. Cl.
*G01N 33/02* (2006.01)
*G01N 33/68* (2006.01)
*H01J 49/00* (2006.01)

(52) U.S. Cl.
CPC ......... *G01N 33/6848* (2013.01); *G01N 33/02* (2013.01); *H01J 49/0036* (2013.01)

(58) Field of Classification Search
CPC ..... G01N 33/02; G01N 33/6848; H01J 49/00; H01J 49/0027; H01J 49/0036
USPC .................... 436/20, 86, 147, 173
See application file for complete search history.

(56) References Cited

U.S. PATENT DOCUMENTS

| | | | |
|---|---|---|---|
| 4,008,388 A | 2/1977 | McLafferty et al. | |
| 5,948,610 A | 9/1999 | Ho et al. | |
| 6,536,599 B1 | 3/2003 | Nielsen | |
| 6,629,040 B1 | 9/2003 | Goodlett et al. | |
| 7,078,684 B2 | 7/2006 | Beu et al. | |
| 7,696,476 B2 | 4/2010 | Kim et al. | |
| 7,799,211 B2 | 9/2010 | Koseoglu et al. | |
| 8,012,764 B2 | 9/2011 | Denny et al. | |
| 8,440,966 B2 | 5/2013 | Choi et al. | |
| 8,969,287 B2 | 3/2015 | Hellerstein | |
| 8,975,084 B2 | 3/2015 | Qian et al. | |
| 2002/0040864 A1 | 4/2002 | Serio et al. | |
| 2004/0029120 A1* | 2/2004 | Goodenowe | G01N 33/6848 435/6.13 |
| 2006/0199279 A1 | 9/2006 | Lopez-avila et al. | |
| 2007/0114394 A1* | 5/2007 | Combs | H01J 49/0463 250/292 |
| 2010/0190260 A1* | 7/2010 | Marshall | C09K 8/524 436/29 |
| 2011/0077155 A1 | 3/2011 | Goodwin | |
| 2011/0269161 A1 | 11/2011 | Gygi et al. | |
| 2012/0197535 A1 | 8/2012 | Goodlett et al. | |
| 2012/0258886 A1 | 10/2012 | Marto et al. | |
| 2012/0291343 A1 | 11/2012 | Schendel et al. | |
| 2014/0238835 A1 | 8/2014 | Mullen et al. | |
| 2014/0377871 A1 | 12/2014 | Zahlsen et al. | |
| 2015/0038333 A1 | 2/2015 | Von Saint et al. | |
| 2015/0106028 A1 | 4/2015 | Koseoglu et al. | |
| 2015/0126384 A1 | 5/2015 | Hogdall et al. | |

FOREIGN PATENT DOCUMENTS

| | | |
|---|---|---|
| CA | 2381685 A1 | 10/2003 |
| WO | WO 83/03676 A1 | 10/1983 |
| WO | WO 00/65354 A1 | 11/2000 |
| WO | WO 2004/008480 A2 | 1/2004 |
| WO | WO 2006/003429 A2 | 1/2006 |

(Continued)

OTHER PUBLICATIONS

Bingol et al., "Metabolomics Beyond Spectroscopic Databases: A Combined MS/NMR Strategy for the Rapid Identification of New Metabolites in Complex Mixtures," Analytical Chemistry, 2015 (7 pages).

Channell et al., "Identification and Monitoring of Intermediates and Products in the Acrylamide Pathway using Online Analysis," Journal of Agricultural and Food Chemistry, 56:6097-6104 (2008).

Ellis et al., "Fingerprinting food; current technologies for the detection of food adulteration and contamination," Chem. Soc. Rev., 41:5706-5727 (2012).

(Continued)

*Primary Examiner* — Maureen Wallenhorst
(74) *Attorney, Agent, or Firm* — Baker Botts L.L.P.

(57) ABSTRACT

The presently disclosed subject matter provides methods for analyzing complex mixtures with ultra high resolution mass spectrometry. In particular, the presently disclosed subject matter provides methods for identifying and monitoring the presence of a compound within a complex mixture. In certain embodiments, the method includes providing a sample of the complex mixture; performing mass spectrometry on the sample of the complex mixture to obtain a mass spectrum; and identifying one or more peaks from the mass spectrum corresponding to the compound. In certain embodiments, the sample is obtained during production of the complex mixture, e.g., a pet food product. In certain embodiments, the sample is prepared by a single alcohol/water extraction step.

41 Claims, 68 Drawing Sheets

(56) References Cited

FOREIGN PATENT DOCUMENTS

| WO | WO 2006/042187 A2 | 4/2006 |
|---|---|---|
| WO | WO 2007/030948 A1 | 3/2007 |
| WO | WO 2008/070391 A2 | 6/2008 |
| WO | WO 2011/042027 A2 | 4/2011 |
| WO | WO 2012/053799 A1 | 4/2012 |
| WO | WO 2013/181758 A1 | 12/2013 |
| WO | WO 2015/051310 A2 | 4/2015 |

OTHER PUBLICATIONS

Garcia et al., "Whisky analysis by electrospray ionization-Fourier transform mass spectrometry," Food Research International, 51:98-106 (2013).

Garrett et al., "Arabica and Robusta Coffees: Identification of Major Polar Compounds and Quantification of Blends by Direct-Infusion Electrospray Ionization-Mass Spectrometry," Journal of Agricultural and Food Chemistry, 60:4253-4258 (2012).

Golon et. al., "An Investigation of the Complexity of Maillard Reaction Product Profiles from the Thermal Reaction of Amino Acids with Sucrose Using High Resolution Mass Spectrometry," Foods 3:461-475 (2014).

Green et al., "Fast Graphically Inspired Algorithm for Assignment of Molecular Formulae in Ultrahigh Resolution Mass Spectrometry," Analytical Chemistry, 2015 (9 pages).

Hwang et al., "Thermally Generated Flavors from Seal Protein Hydrolysate," in Flavor and Lipid Chemistry of Seafoods, F. Shahidi and K.R. Cadwallader, Eds. 1997, Amer. Chemical Soc: Washington. p. 76-84.

Kim et al., "Graphical method for Analysis of Ultrahigh-Resolution Broadband Mass Spectra of Natural Organic Matter, the Van Krevelen Diagram" Anal. Chem. 75:5336-5344 (2003).

Kuhnert et al., "Mass spectrometric characterization of black tea thearubigins leading to an oxidative cascade hypothesis for thearubigin formation," Rapid Communications in Mass Spectrometry, 24:3387-3404 (2010).

Lohne et al., "Application of Single-Stage Orbitrap Mass Spectrometry and Differential Analysis Software to Nontargeted Analysis of Contaminants in Dog Food: Detection, Identification, and Quantification of Glycoalkaloids," Journal of Agricultural and Food Chemistry, 2015 (9 pages).

Perdue et al., "Isobaric Molecular Formulae of C, H, and O: A View from the Negative Quadrants of van Krevelen Space," Analytical Chemistry, 2015 (7 pages).

Porcari et al., "High throughput MS techniques for caviar lipidomics," Analytical Methods, 6:2436-2443 (2014).

Roullier-Gall, C. et al., How Subtle Is the "Terroir" Effect? Chemistry-Related Signatures of Two "Climats de Bourgogne," PLoS One, 9(5):e97615 (2014), 12 pages.

Sleighter et al., "The application of electrospray ionization coupled to ultrahigh resolution mass spectrometry for the molecular characterization of natural organic matter," J Mass Spectrom. 42:559-574 (2007).

Wang et al., "The latest developments and applications of mass spectrometry in food-safety and quality analysis," Trends in Analytical Chemistry, 52:170-185 (2013).

Wu et al., "Characterization of Vegetable Oils: Detailed Compositional Fingerprints Derived from Electrospray Ionization Fourier Transform Ion Cyclotron Resonance Mass Spectrometry," Journal of Agricultural and Food Chemistry, 52:5322-5328 (2004).

Golon, et al., "An Investigation of the Complexity of Maillard Reaction Product Profiles from the Thermal Reaction of Amino Acids with Sucrose Using High Resolution Mass Spectrometry", Foods, vol. 3, No. 3, Aug. 7, 2014 (Aug. 7, 2014), pp. 461-475, XP055498806, DOI: 10.3390/foods3030461.

Marshall, et al., "Monitoring chemical changes during food sterilisation using ultrahigh resolution mass spectrometry", Food Chemistry, Elsevier Ltd, NL, vol. 242, Sep. 14, 2017 (Sep. 14, 2017), pp. 316-322, XP085213115, ISSN: 0308-8146, DOI: 10.1016/J.FOODCHEM.2017.09.074.

Roullier-Gall, et al., "High precision mass measurements for wine metabolomics", Frontiers in Chemistry, vol. 2, Nov. 13, 2014 (Nov. 13, 2014), XP055498813, DOI: 10.3389/fchem.2014.00102.

Amrein et al., "Occurrence of acrylamide in selected foods and mitigation options," Food Additives and Contaminants, 24(S1):13-25 (2007).

Awad et al., "Mass Spectrometry, Review of the Basics: Ionization," Applied Spectroscopy Reviews, 50:158-175 (2015).

Balagiannis et al., "Kinetic Modeling of the Formation of Volatile Compounds in Heated Beef Muscle Extracts Containing Added Ribose," Chapter 2, American Chemical Society: Washington DC. pp. 13-25 (2010).

Engel et al., "Solvent assisted flavor evaporation—a new and versatile technique for the careful and direct isolation of aroma compounds from complex food matrices," Eur Food Res Technol, 209:237-241 (1999).

Frank et al., "Sensory Activity, Chemical Structure, and Synthesis of Maillard Generated Bitter-Tasting 1-Oxo-2,3-dihydro-1H-indolizinium-6-olates," J. Agric. Food Chem., 51:2693-2699 (2003).

Graf et al., "Reducing the acrylamide content of a semi-finished biscuit on industrial scale," LWT 39:724-728 (2006).

Hammes, Principles of Chemical Kinetics, Chapter 1—Empirical Analysis of Reaction Rates, Academic Press: London, 1978, pp. 1-23.

Harrison et al., "Analysis of high-molecular-weight fructan polymers in crude plant extracts by high-resolution LC-MS," Analytical and Bioanalytical Chemistry, 401:2955-2963 (2011).

International Search Report dated Aug. 29, 2016 in International Application No. PCT/US2016/022149.

Jia et al., "Analysis of additives in dairy products by liquid chromatography coupled to quadrupole-orbitrap mass spectrometry," Journal of Chromatography A, 1336:67-75 (2014).

Koutsidis et al., "Investigations on the Effect of Amino Acids on Acrylamide, Pyrazines, and Michael Addition Products in Model Systems," J. Agric. Food Chem., 57:9011-9015 (2009).

Lin et al., "Ultrahigh resolution mass spectrometry-based metabolic characterization reveals cerebellum as a disturbed region in two animal models," Talanta, 118:45-53 (2014).

Schieberle, "The Carbon Module Labeling (CAMOLA) Technique: A Useful Tool for Identifying Transient Intermediates in the Formation of Maillard-Type Target Molecules," Ann. N.Y. Acad. Sci., 1043:236-248 (2005).

Stadler, "Formation and mitigation of process toxicants," Toxicology Letters, 229S: S26-S27 (2014).

Vahur et al., "Analysis of dammar resin with MALDI-FT-ICR-MS and APCI-FT-ICR-MS," Journal of Mass Spectrometry, 47:392-409 (2012).

Wang et al., "Identification and elucidation of the structure of in vivo metabolites of diaveridine in chicken," Journal of Chromatography B, 965:91-99 (2014).

\* cited by examiner

Filtering to identify compounds containing compounds with composition $C_xH_yO_3$

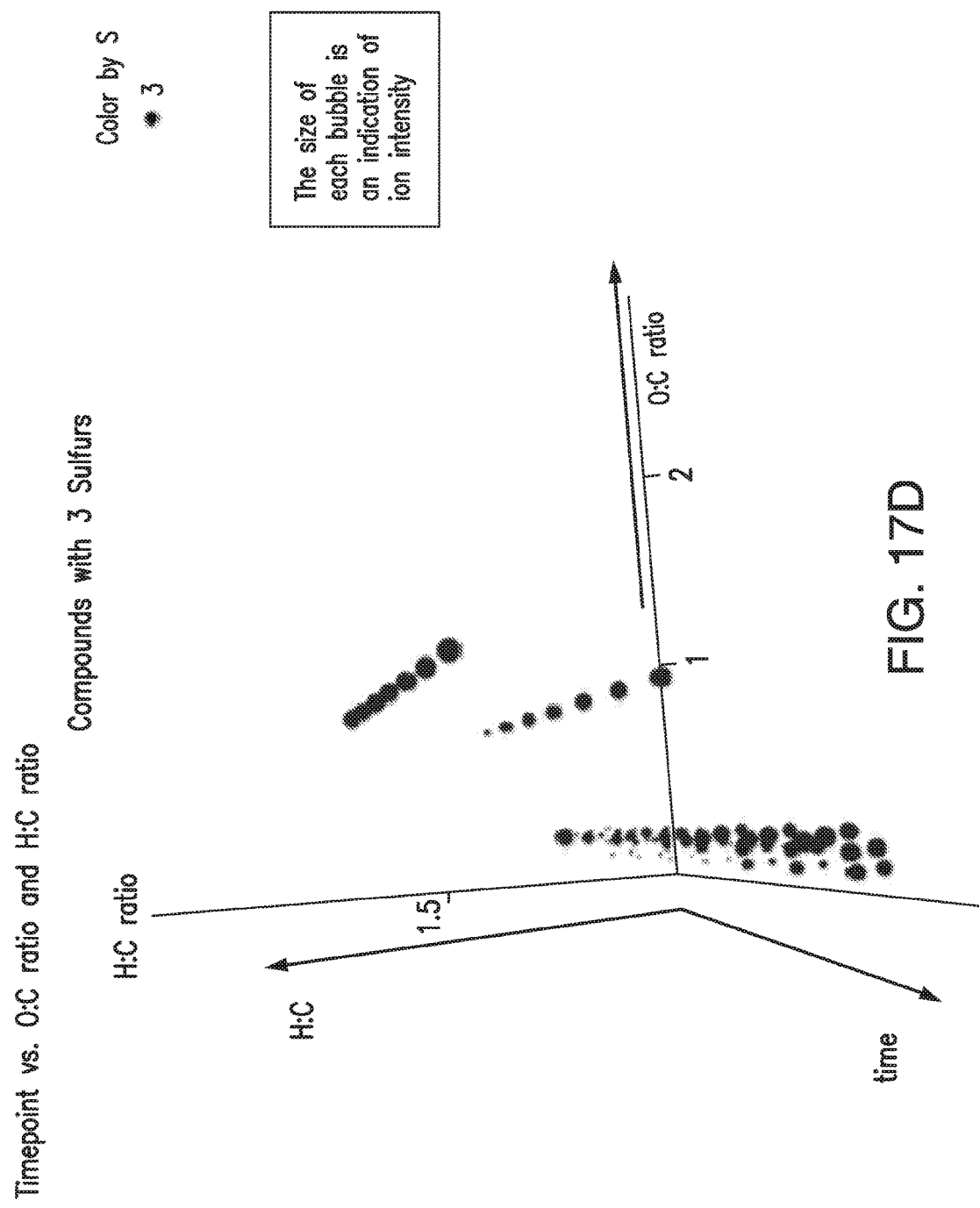

Chemical Formula: $C_8H_{15}NO_7$
4-enaminol

RRMent

FIG. 20B

ADDN = Addition DH = Dehydration; RR = Rearrangement; ELIM = Elimination; C = Cyclisation

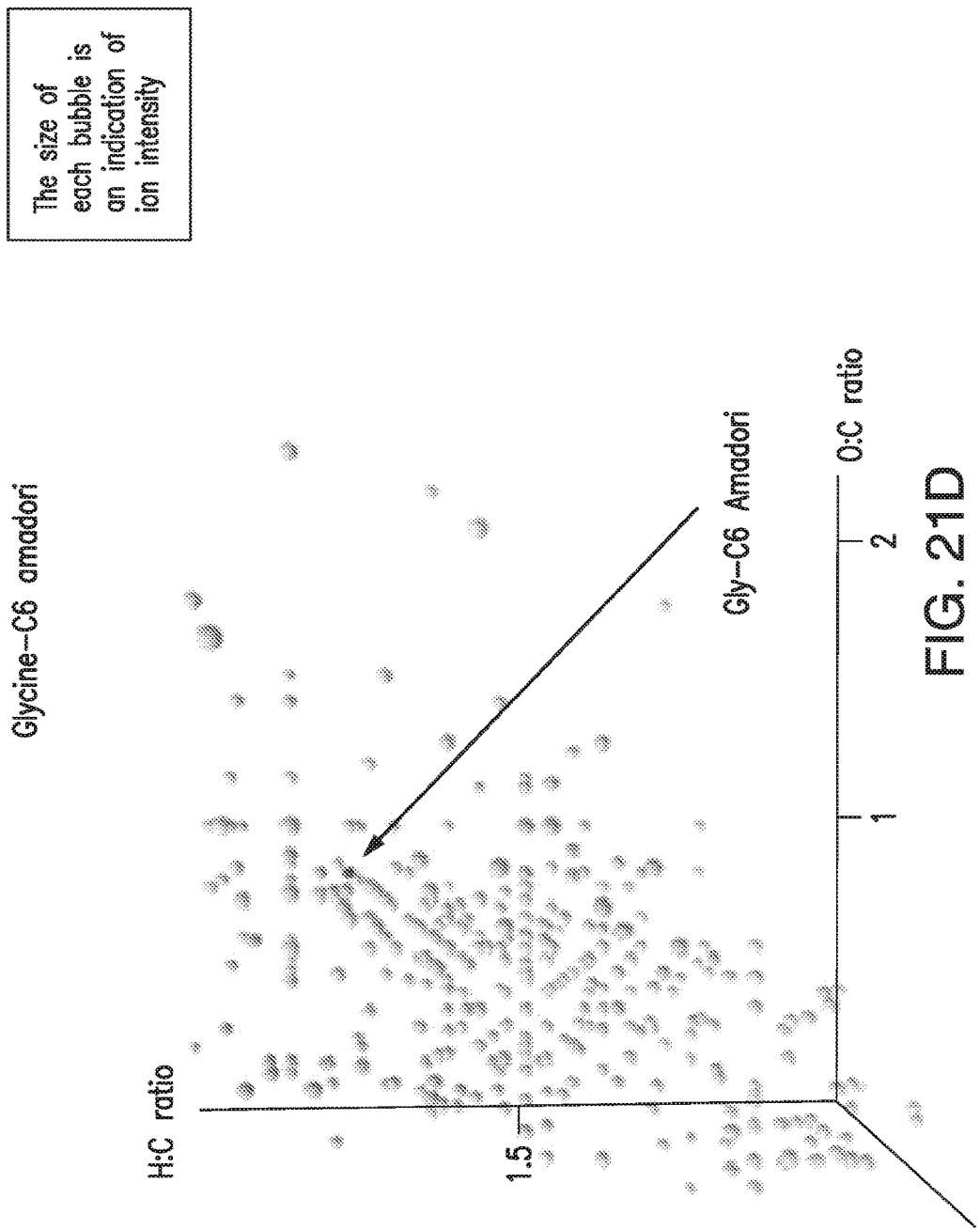

ULTRA HIGH RESOLUTION MASS SPECTROMETRY AND METHODS OF USING THE SAME

CROSS-REFERENCE TO RELATED APPLICATIONS

This application is a U.S. National Stage Patent Application under 35 U.S.C. § 371 of International Application No. PCT/US2016/022149, filed on Mar. 11, 2016, which claims priority to U.S. Provisional Application No. 62/132,492, filed Mar. 12, 2015, and U.S. Provisional Application No. 62/269,897, filed Dec. 18, 2015, which are incorporated by reference herein in their entireties.

FIELD

The presently disclosed subject matter relates to ultra high resolution mass spectrometry and methods of its use in analyzing complex mixtures. In particular, the subject matter of the present disclosure includes methods for analyzing compounds present in a food product.

BACKGROUND

Mass spectrometry is an analytical technique used to analyze the compounds contained within a sample. A sample can be ionized to generate ions that can be subjected to the influences of electric and magnetic fields and separated into various space components dependent on the mass-to-charge ratio within a mass spectrometer. In this manner it is possible to study the products of ionization of a particular sample, and, by using appropriate calibrations, analyze an unknown sample to determine the relative concentrations of its components. In detecting and measuring the ionic component existing in the exit field of a mass spectrometer, ions of a given mass-to-charge (m/z) ratio can be directed upon an ion collector and the intensity of the corresponding ion current can be measured by means of a direct current amplifier. By varying an analyzing electric or magnetic field or moving the collector in the exit field, various types of ions are caused to fall upon the collector successively and the respective intensities are measured, which can allow the identification and quantification of compounds that correspond to the ions.

A typical process for analyzing the changes in the chemical composition of a food product during processing can include preparing multiple samples (pre-thermal processing) in small vessels (e.g., sealed glass ampoules), which are heated for different times and then rapidly cooled to stop the reactions (Balagiannis et al., 2010, American Chemical Society: Washington D.C. p. 13-25). Each sample is then extracted and concentrated, which can take several days. The composition of each sample is then analyzed using gas chromatography-mass spectrometry (GC-MS) or liquid chromatography-mass spectrometry (LC-MS) to measure the composition at each time point. Each GC-MS or LC-MS run can take up to 60 minutes to complete and with 3 replicates per sample, can give a maximum throughput of 8 samples per day per instrument. In addition, multiple runs may be required to identify different classes of compounds of interest, e.g., amino acids, free fatty acids and nucleotides, due to the different sample preparation methods used for the different chemical classes. The analysis then produces two types of information, the number of compounds resolved by the chromatography and the number of compounds identified. Typically GC-MS will resolve around 100-200 compounds and identify about 40-50 compounds from the spectral libraries and the available retention indices.

From the data obtained from GC-MS and/or the LC-MS analysis, chemical changes can be plotted to examine the course of the reactions or the kinetics of specific reactions (Balagiannis et al., 2010, American Chemical Society: Washington D.C. p. 13-25). However, such a technique can have limitations. For example, heating individual samples to mimic the exact time/temperature conditions that occur in a real food product can be very difficult. In particular, there can be lags in the time to reach the desired temperature and to cool the vessels to stop the reactions, which can result in the introduction of experimental error in the form of variation and lack of correlation with a real food process.

In addition, analyses with GC-MS and LC-MS provide identification for known compounds, i.e., those compounds whose spectra and chromatographic behavior (retention indices) are known and published. Whereas, identifying unknown compounds detected using GC-MS and LC-MS is a time-consuming task and is not always successful as GC-MS and LC-MS analyses alone provide insufficient data to enable structure elucidation; therefore, the results of such targeted LC- and GC-based analyses are not as "data rich" as they could be. This lack of depth in the analytical data then limits the interpretation that can be achieved using data analysis techniques like principal component analysis (PCA) or partial least squares analysis (PLS), which correlate sample properties with the chemical variables. As data analysis techniques based on GC-MS and LC-MS data consider only a limited number of known chemical entities, it is not possible to fully understand the chemistry occurring during processing of real, complex food systems which contain many previously undescribed entities. Therefore, suggestions about ways to intervene to improve flavor, reduce nutrient destruction or control the formation of undesirable compounds like bitter compounds (Frank et al., Journal of Agricultural and Food Chemistry, 2003. 51(9): p. 2693-2699) or potentially toxic compounds (Stadler, Toxicology Letters, 2014. 229: p. S26-S27) are also limited.

Furthermore, to monitor the chemical reactions involving known chemical entities that occur during food processing using conventional approaches can be challenging unless labeled precursors are added to the food product at the initiation of the food process, e.g., using the CAMOLA technique (Schieberle, Annals of the New York Academy of Sciences, 2005. 1043: p. 236-248). This technique requires the precursors to be synthesized from isotopically enriched starting materials and assumes the added labeled compounds behave exactly the same as the "native" compounds. However, isotopically enriched precursors can react and interact with other compounds in a complex food matrix at a different rate to the non-isotopically labeled compound (the kinetic isotope effect), leading to potentially inaccurate results.

Therefore, there is a need in the art for methods that allow for monitoring, evaluating and identifying chemical reactions that occur during processing of complex food products.

SUMMARY OF THE INVENTION

The presently disclosed subject matter provides methods for analyzing compounds present within complex mixtures and for identifying and monitoring chemical reactions during the production of complex mixtures using ultra high resolution mass spectrometry.

In one aspect, the presently disclosed subject matter provides methods for identifying the presence of a compound within a complex mixture. In certain embodiments, the method comprises providing a sample of the complex mixture. The method can include performing mass spectrometry, e.g., ultra high resolution mass spectrometry, on the sample of the complex mixture to obtain a mass spectrum and identifying one or more peaks from the mass spectrum corresponding to the compound. In certain embodiments, the sample is obtained during production and/or thermal processing of the complex mixture. In certain embodiments, the sample is prepared by a single alcohol/water extraction step.

In another aspect, the presently disclosed subject matter provides methods for quantifying and/or monitoring a change in the amount of a compound between two or more samples of a complex mixture. In certain embodiments, the method comprises providing a first sample and a second sample of the complex mixture. The method can comprise performing mass spectrometry, e.g., ultra high resolution mass spectrometry, on the first sample of the complex mixture to obtain a first mass spectrum and performing mass spectrometry on the second sample of the complex mixture to obtain a second mass spectrum. In certain embodiments, the method further comprises comparing one or more peaks of the first mass spectrum corresponding to a compound to one or more peaks of the second mass spectrum corresponding to the compound and determining a difference in the amount of the compound within the first sample as compared to the amount of the compound in the second sample. In certain embodiments, the method can further comprise providing a third sample of the complex mixture; performing mass spectrometry on the third sample of the complex mixture to obtain a third mass spectrum; and comparing one or more peaks of the third mass spectrum corresponding to the compound to one or more peaks of the first mass spectrum and/or second mass spectrum corresponding to the compound and determining a difference in the amount of the compound within the third sample as compared to the amount of the compound in the first and/or second samples.

In certain embodiments, the first, second and/or third samples can be obtained at different time points during production of the complex mixture. For example, and not by way of limitation, the first sample can be obtained at an earlier time point during the production process of the complex mixture than the second sample. In certain embodiments, the first, second and/or third samples are samples from different production batches of the same product, e.g., pet food product. In certain embodiments, the first, second and/or third samples are samples of different but related complex mixtures. For example, and not by way of limitation, the first, second and/or third samples can be products, e.g., commercial products, of a similar type and/or similar products, e.g., pet food products, prepared using different recipes. In certain embodiments, one or more of the first, second, and/or third samples can be a reference sample having a known chemical composition.

In certain embodiments, the methods of the present disclosure can be used to analyze and/or compare the chemical compositions of two or more, three or more, four or more, five or more, six or more, seven or more, eight or more, nine or more or ten or more samples, which can be from different time points during a production process and/or can be from different batches of the same product and/or can be from similar products manufactured using different recipes or combinations thereof.

The presently disclosed subject matter further provides a method for quantifying the amount of a compound within a complex mixture that comprises providing a sample of the complex mixture and performing mass spectrometry on the sample of the complex mixture to obtain a mass spectrum. In certain embodiments, the method can further include identifying one or more peaks from the mass spectrum corresponding to the compound and determining the intensity of the one or more peaks corresponding to the compound to quantify the amount of the compound within the complex mixture. For example, and not by way of limitation, the amount of a compound in a complex mixture can be determined by comparing the peak intensity that corresponds to that compound to the peak intensity of a second compound within the complex mixture that is of a known concentration, e.g., an isotopically labeled compound and/or a compound that was added to the sample (e.g., immediately prior to analysis).

In certain embodiments, the mass spectrometry performed within the disclosed methods is performed using an ultra high resolution mass spectrometer. In certain embodiments, the ultra high resolution mass spectrometer is a Fourier transform ion cyclotron resonance mass spectrometer.

In certain embodiments, the compound analyzed by the disclosed methods can be a precursor flavor compound, flavor compound, nutrient, trace metal, amino acid, peptide, protein, anti-nutritional compound, undesirable compound, toxic compound, food additive, impurity, carbohydrate, sugar, oligosaccharide, lipid, fatty acid, mineral, pro-oxidant, antioxidant, a product, a reaction intermediate or reactant of a chemical reaction, a reactant of a Maillard reaction, a product of a Maillard reaction, a Maillard reaction intermediate or combinations thereof. Non-limiting examples of nutrients include Vitamin B compounds, thiamine, taurine, riboflavin, a Vitamin A compound, retinol, essential amino acids, fatty acids, sugars and combinations thereof. In certain embodiments, the compound is a reaction product or a degradation product of the compound. In certain embodiments, the compound is indicative of a raw material used to prepare the complex mixture.

In certain embodiments, the complex mixture comprises a food product. Non-limiting examples of food products include a pet food product, a chocolate product, a candy product, a gum product, a processed food product or combinations thereof. In certain embodiments, the sample is obtained during production of the complex mixture.

The presently disclosed subject matter further provides a method for monitoring and/or modulating the production of a complex mixture to reduce the amount of one or more compounds within the complex mixture and/or for determining how to reduce the level of one or more compounds during production of the complex mixture. In certain embodiments, the method can comprise providing a first sample and a second sample of the complex mixture, wherein the first sample is obtained prior to the second sample during a process of producing the complex mixture. In certain embodiments, the method further comprises performing mass spectrometry on the first sample of the complex mixture to obtain a first mass spectrum and performing mass spectrometry on the second sample of the complex mixture to obtain a second mass spectrum. In certain embodiments, the method can further comprise comparing one or more peaks of the first mass spectrum corresponding to the compound to one or more peaks of the second mass spectrum corresponding to the compound to determine the amount of the compound within the second sample as compared to the amount of the compound in the first sample.

In certain embodiments, the methods can include modulating the process of producing the complex mixture to reduce the amount of the compound in the complex mixture. In certain embodiments, the method can further comprise analyzing a reduction of the compound within the complex mixture. In certain embodiments, the compound can be a toxic compound, a vitamin degradation product, nutrient, an anti-nutritional compound, a peptide, a pro-oxidant, an undesirable compound, an undesirable flavor compound, an impurity or combinations thereof.

The presently disclosed subject matter further provides a method for monitoring and/or modulating the production of a complex mixture to increase the amount of one or more compounds within the complex mixture and/or for determining how to increase the level of one or more compounds during production of the complex mixture. In certain embodiments, the method can comprise providing a first sample and a second sample of the complex mixture, wherein the first sample is obtained prior to the second sample during a process of producing the complex mixture. In certain embodiments, the method can further comprise performing mass spectrometry on the first sample of the complex mixture to obtain a first mass spectrum and performing mass spectrometry on the second sample of the complex mixture to obtain a second mass spectrum. The method can further comprise comparing one or more peaks of the first mass spectrum corresponding to the compound to one or more peaks of the second mass spectrum corresponding to the compound to determine the amount of the compound within the second sample as compared to the amount of the compound in the first sample and modulating the process of producing the complex mixture to increase the amount of the compound in the complex mixture. In certain embodiments, the method can further comprise analyzing an increase of the compound within the complex mixture. In certain embodiments, the compound can be a flavor compound, a nutrient, a vitamin, a degradation product, a peptide, a mineral, an antioxidant, a product of a Maillard reaction or combinations thereof.

In certain embodiments, a method for monitoring and/or modulating the production of a complex mixture can include identifying the occurrence of one or more chemical reactions that increases or decreases the concentration of a compound. The method can include altering the identified chemical reaction. In certain embodiments, a method for monitoring and/or modulating the production of a complex mixture can include increasing or decreasing the temperature of the process.

The presently disclosed subject matter further provides a method for determining the occurrence of and/or monitoring a chemical reaction during production of a complex mixture. The method can comprise providing a first sample and a second sample of the complex mixture, wherein the first sample is obtained prior to the second sample during a process of producing the complex mixture, performing mass spectrometry on the first sample of the complex mixture to obtain a first mass spectrum, performing mass spectrometry on the second sample of the complex mixture to obtain a second mass spectrum and comparing one or more peaks of the first mass spectrum corresponding to a compound to one or more peaks of the second mass spectrum corresponding to a chemical reaction product of the compound to determine the occurrence of a chemical reaction. In certain embodiments, the chemical reaction product and/or reactant(s) of a chemical reaction can be determined by predicting the chemical formulas of such compounds from the accurate mass of the compound. In certain embodiments, the chemical reaction can be, but is not limited to, Maillard reactions, a condensation reaction, an elimination reaction, a hydrolysis reaction, a hydration reaction, an oxidation reaction, a decarboxylation reaction, a sulfur-oxygen exchange reaction, an amination reaction, a reaction involving disulfide bond formation or cleavage, a deamination reaction, a transamination reaction, a reduction reaction, a redox reaction, a nucleophilic substitution reaction, a nucleophilic addition reaction, an electrophilic aromatic substitution reaction, a glycosylation reaction and/or a phosphorylation reaction.

The presently disclosed subject matter further provides methods for determining the reaction rate of a chemical reaction occurring within a complex mixture. The method can comprise providing a first sample and a second sample of the complex mixture, performing mass spectrometry on the first sample of the complex mixture using an ultra high resolution mass spectrometer to obtain a first mass spectrum, performing mass spectrometry on the second sample of the complex mixture using an ultra high resolution mass spectrometer to obtain a second mass spectrum, identifying one or more compounds that correspond to the one or more peaks of the first mass spectrum and the second mass spectrum, analyzing the intensity differences between the one or more peaks corresponding to the one or more compounds to identify the change in concentration of the one or more compounds, determining a rate of change in concentration of the one or more compounds from the change in concentration of the one or more compounds; and determining the reaction rate of a chemical reaction from the rate of change in concentration of the one or more compounds. In certain embodiments, the first sample can be obtained prior to the second sample during a process of producing the complex mixture. In certain embodiments, the method can further include increasing or decreasing the concentration of one or more compounds in the second sample compared to the first sample. In certain embodiments, the method can further include determining the reaction rate of two or more chemical reactions in a multicomponent or stepwise reaction and determining the reaction rate of the multicomponent or stepwise reaction therefrom. The method can further include providing a third sample of the complex mixture, performing mass spectrometry on the third sample of the complex mixture using an ultra high resolution mass spectrometer to obtain a third mass spectrum, and comparing one or more peaks of the third mass spectrum corresponding to the compound to one or more peaks of the first mass spectrum and/or second mass spectrum corresponding to the compound. In certain embodiments, these steps can be repeated for a fourth sample and, optionally, a fifth sample.

In certain embodiments, the first sample and the second sample can be from a first complex mixture. The method can further comprise providing a third sample and a fourth sample of a second complex mixture, performing mass spectrometry on the third sample of the second complex mixture using an ultra high resolution mass spectrometer to obtain a third mass spectrum, performing mass spectrometry on the fourth sample of the second complex mixture using an ultra high resolution mass spectrometer to obtain a fourth mass spectrum, identifying one or more compounds that correspond to the one or more peaks of the third mass spectrum and the fourth mass spectrum, analyzing the intensity differences between the one or more peaks corresponding to the one or more compounds to identify the change in concentration of the one or more compounds, determining a rate of change in concentration of the one or more compounds from the change in concentration of the one or more compounds, and determining the reaction rate of a chemical reaction from the rate of change in concentration of the one or more compounds in the first complex mixture and the rate of change in concentration of the one or more compounds in the second complex mixture. In certain embodiments, the first complex mixture can be thermally processed at a higher temperature than the second complex mixture. In certain embodiments, the method can further include increasing or decreasing the concentration of one or more compounds in the second complex mixture compared to the first complex mixture.

The presently disclosed subject matter provides methods for identifying the presence of a compound, for monitoring the change in the presence of a compound, for quantifying the amount of a compound and/or for modulating the level of a compound during the processing of cocoa beans, e.g., during the fermentation of cocoa beans or the roasting of cocoa beans, and/or the processing of peanuts, e.g., the roasting of peanuts. For example, and not by way of limitation, a method for determining the level of a compound that is produced during the fermentation of cocoa beans, e.g., fermentation product, can comprise providing a first sample and a second sample of fermented cocoa beans, wherein the first sample is obtained prior to the second sample during a cocoa bean fermentation process, performing mass spectrometry on the first sample of the fermented cocoa beans to obtain a first mass spectrum, performing mass spectrometry on the second sample of the fermented cocoa beans to obtain a second mass spectrum and comparing one or more peaks of the first mass spectrum corresponding to a cocoa bean fermentation product to one or more peaks of the second mass spectrum corresponding to the cocoa bean fermentation product to determine the level of cocoa bean fermentation. In certain embodiments, the method can further comprise providing a third sample of fermented cocoa beans; performing mass spectrometry on the third sample of the fermented cocoa beans to obtain a third mass spectrum; and comparing one or more peaks of the third mass spectrum corresponding to the cocoa bean fermentation product to one or more peaks of the first mass spectrum and/or second mass spectrum corresponding to the cocoa bean fermentation product and determining a difference in the amount of the product within the third sample as compared to the amount of the product in the first and/or second samples. In certain embodiments, the first, second and/or third samples are obtained at different time points during a cocoa bean fermentation process. For example, and not by way of limitation, the first sample can be obtained at an earlier time point during the cocoa bean fermentation process than the second sample. In certain embodiments, the third sample can be obtained at a later time point during a cocoa bean fermentation process than the first and/or second sample. In certain embodiments, the cocoa bean fermentation product can be a sugar molecule, fat molecule, peptide, protein, flavor precursor compound, flavor compound or combinations thereof. In certain embodiments, the cocoa bean fermentation product can be a compound that indicates when fermentation is complete, e.g., fermentation marker.

The presently disclosed subject matter further provides a method for determining the level of lipid oxidation during production of a complex mixture, e.g., during thermal processing or other types of processing of a complex mixture such as a food product. In certain embodiments, the method can comprise providing a first sample and a second sample of the complex mixture, wherein the first sample is obtained prior to the second sample during a process of producing the complex mixture. The method can further include performing mass spectrometry on the first sample of the complex mixture to obtain a first mass spectrum, performing mass spectrometry on the second sample of the complex mixture to obtain a second mass spectrum and comparing one or more peaks of the first mass spectrum corresponding to a product of lipid oxidation to one or more peaks of the second mass spectrum corresponding to the product to determine the level of lipid oxidation in the complex mixture. In certain embodiments, the disclosed method can also be used to determine changes in the level of lipids over time, e.g., a decrease in the level of lipids due to lipid oxidation, during a process of producing the complex mixture.

The presently disclosed subject matter further provides a method for monitoring protein hydrolysis reactions during production of a complex mixture, e.g., by monitoring amino acid and peptide levels, which can comprise providing a first sample and a second sample of the complex mixture, wherein the first sample is obtained prior to the second sample during a process of producing the complex mixture. In certain embodiments, the method can further comprise performing mass spectrometry on the first sample of the complex mixture to obtain a first mass spectrum, performing mass spectrometry on the second sample of the complex mixture to obtain a second mass spectrum and comparing one or more peaks of the first mass spectrum corresponding to a peptide and/or amino acid from a hydrolyzed protein to one or more peaks of the second mass spectrum corresponding to the peptide and/or amino acid to monitor hydrolysis reactions over time.

The presently disclosed subject matter further provides method for identifying the presence and/or level of a food additive, e.g., emulsifier, within a complex mixture, where the method comprises providing a sample of the complex mixture. In certain embodiments, the method can further comprise performing mass spectrometry on the sample of the complex mixture using an ultra high resolution mass spectrometer to obtain a mass spectrum and identifying one or more peaks from the mass spectrum corresponding to the food additive, e.g., emulsifier. In certain embodiments, the complex mixture can be a pet food product, e.g., a commercially available pet food product. In certain embodiments, the disclosed methods can be used to identify the presence of a compound and/or determine the amount of a compound that is added to the recipe of a complex mixture prior, e.g., added at the beginning of the production process of a complex mixture (e.g., a thermal process).

The presently disclosed subject matter further provides a method for measuring a difference in the amount of a compound between samples of two or more, three or more, four or more, five or more, six or more, seven or more, eight or more, nine or more, ten or more complex mixtures. In certain embodiments, the method can comprise providing a sample of a first complex mixture and providing a sample of a second complex mixture. The method can further comprise performing mass spectrometry on the sample of the first complex mixture using an ultra high resolution mass spectrometer to obtain a first mass spectrum, and performing mass spectrometry on the sample of the second complex mixture using an ultra high resolution mass spectrometer to obtain a second mass spectrum. In certain embodiments, the method comprises comparing one or more peaks of the first mass spectrum corresponding to a compound to one or more peaks of the second mass spectrum corresponding to the compound and determining a difference in the amount of the compound within the sample of the first complex mixture as compared to the amount of the compound in the sample of the second complex mixture. In certain embodiments, one of the samples can be from a reference complex mixture having a known chemical composition. In certain embodiments, the complex mixtures can be different production batches of the same product and/or similar products having different recipes.

BRIEF DESCRIPTION OF THE DRAWINGS

FIG. 17D. Van Krevelen diagram of the level of compounds containing 3 sulfur atoms during the processing of a pet food product.

FIG. 20B. The types of reactions that can occur during a Maillard reaction (non-limiting).

FIG. 21D. Van Krevelen diagram showing the presence of a glycine-$C_6$ Amadori product during the production of a pet food.

DETAILED DESCRIPTION

Figure 1:
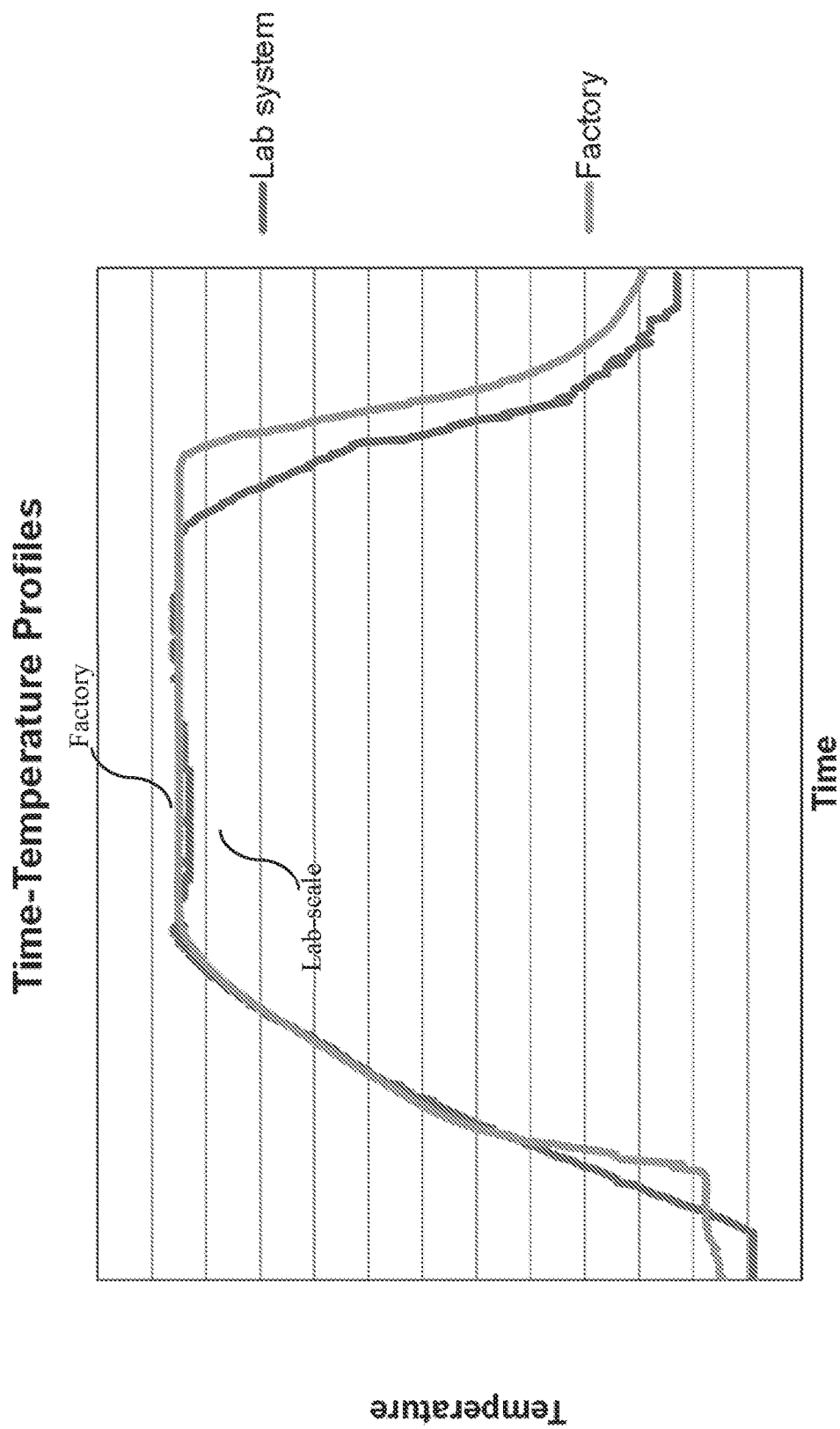
FIG. 1. Comparison of the time and temperature profiles of a lab-scale sterilization process and a factory-scale sterilization process.

The presently disclosed subject matter provides targeted and untargeted methods for analyzing complex mixtures with ultra high resolution mass spectrometry and methods for visualizing information obtained from ultra high resolution mass spectrometry of such complex mixtures. In particular, the presently disclosed subject matter includes methods for identifying one or more compounds in a complex mixture, e.g., using chemical formula predictions from accurate mass data, and methods for monitoring and identifying the reactions that occur during the production of a complex mixture, e.g., by identifying correlations between potential reactants and products using chemical formula differences. In certain embodiments, the presently disclosed subject matter includes methods for measuring the change in the amount of one or more compounds between two or more samples of a complex mixture, and provides methods for identifying differences in the compositions of two or more complex mixtures, e.g., two or more products of a similar type. The present disclosure further provides methods for identifying and monitoring the Maillard reactions that occur during the production of a complex mixture.

1. Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, "taste profile" refers to a combination of tastes, such as, for example, one or more of a sweet, sour, salt, bitter, umami, kokumi and free fatty acid taste. In certain embodiments, a taste profile is produced by one or more tastant that is present in a composition at the same or different concentrations. In certain embodiments, a taste profile refers to the intensity of a taste or combination of tastes, for example, a sweet, sour, salt, bitter, umami, kokumi and free fatty acid taste, as detected by a subject or any assay known in the art. In certain embodiments, modifying, changing or varying the combination of tastants in a taste profile can change the sensory experience of a subject.

As used herein, "flavor" refers to one or more sensory stimuli, such as, for example, one or more of taste (gustatory), smell (olfactory), touch (tactile) and temperature (thermal) stimuli. In certain non-limiting embodiments, the sensory experience of a subject exposed to a flavor can be classified as a characteristic experience for the particular flavor. For example, a flavor can be identified by the subject as being, but not limited to, a floral, citrus, berry, nutty, caramel, chocolate, peppery, smoky, cheesy, meaty, etc., flavor. As used herein, a flavor composition can be selected from a liquid, solution, dry powder, spray, paste, suspension and any combination thereof. The flavor can be a natural composition, an artificial composition, a nature identical,\ or any combination thereof.

As used herein, "flavor profile" refers to a combination of sensory stimuli, for example, tastes, such as sweet, sour, bitter, salty, umami, kokumi and free fatty acid tastes, and/or olfactory, tactile and/or thermal stimuli. In certain embodiments, the flavor profile comprises one or more flavors which contribute to the sensory experience of a subject. In certain embodiments, modifying, changing or varying the combination of stimuli in a flavor profile can change the sensory experience of a subject.

As used herein, "palatability" can refer to the overall willingness of an individual to eat a certain food product. For example, and not by way of limitation, the individual can be a mammal such as a human or a companion animal. In certain embodiments, "palatability" can mean a relative preference of an individual for one food product over another. For example, when an individual shows a preference for one of two or more food products, the preferred food product is more "palatable," and has "enhanced palatability." In certain embodiments, the relative palatability of one food product compared to one or more other food products can be determined, for example, in side-by-side, free-choice comparisons, e.g., by relative consumption of the food products, or other appropriate measures of preference indicative of palatability. In certain embodiments, the methods of the presently disclosed subject matter can be used to increase the palatability of a food product, e.g., a pet food product. In certain embodiments, increasing the "palatability" of a pet food product can lead to an increase in the enjoyment and acceptance of the pet food by the companion animal to ensure the animal eats a "healthy amount" of the pet food. The term "healthy amount" of a pet food as used herein refers to an amount that enables the companion animal to maintain or achieve an intake contributing to its overall general health in terms of micronutrients, macronutrients and calories, such as set out in the Association of American Feed Control Officials (AAFCO) Nutritional Standards, e.g., in the AAFCO 2015 Official Publication, or the European Pet Food Industry Federation (FEDIAF) Nutritional Guidelines, available at http://www.fediaforg/self-regulation/nutrition/.

As used herein, the term "complex mixture" refers to a mixture that comprises at least about 3, at least about 4 or at least about 5 compounds that can be identified and/or quantified in the disclosed methods. In certain embodiments, a "complex mixture" can include at least about 10, at least about 20, at least about 30, at least about 40, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1,000, at least about 1,500, at least about 2,000, at least about 2,500, at least about 3,000, at least about 3,500, at least about 4,000, at least about 4,500, at least about 5,000, at least about 5,500 at least about 6,000, at least about 6,500, at least about 7,000, at least about 7,500, at least about 8,000, at least about 8,500, at least about 9,000, at least about 9,500, at least about 10,000, at least about 10,500, at least about 11,000, at least about 11,500 or at least about 12,000 compounds having different identities or comprising different species. In certain embodiments, a complex mixture of the presently disclosed subject can comprise from about 2,000 to about 3,000 non-volatile compounds. In certain embodiments, a complex mixture of the presently disclosed subject can comprise from about 100 to about 1,000 volatile compounds. Non-limiting examples of complex mixtures include food products, pet food products, candy products, chocolate products, gum products and combinations thereof.

The term "food product," as used herein, refers to any food product, for example, those set forth in 21 CFR 101.12, the contents of which are hereby incorporated by reference. Non-limiting examples of such food products include frozen desserts, baked goods, fillings, nutritional drinks, beverages, salad dressing or similar dressing, sauces, icings, puddings and custards, batters, and the like. Additional non-limiting examples of food products include food product ingredients, meat stews, tagines, hotpots, stir-fries and processed food products such as pasta sauces, soups, cook-in sauces, vegetable stocks and meat stocks. Various baked goods are disclosed in U.S. Pat. No. 6,536,599, the disclosure of which is herein incorporated by reference in its entirety. Non-limiting examples of bakery goods includes cookies, cakes, rolls, pastries, pie dough, brownies, breads, bagels and the like. The flavor compositions are also suitable as a component in frozen foods.

The terms "pet food" or "pet food product", used interchangeably herein, refer to a product or composition that is intended for consumption by a companion animal, such as cats, dogs, guinea pigs, rabbits, birds and horses. For example, but not by way of limitation, the companion animal can be a "domestic" cat such as *Felis silvestris catus* or *Felis domesticus*. In certain embodiments, the companion animal can be a "domestic" dog, e.g., *Canis lupus familiaris* or *Canis familiaris*. A "pet food" or "pet food product" includes any food, feed, snack, food supplement, liquid, beverage, treat, meal substitute or meal replacement. For example, and not by way of limitation, the pet food product can be a wet food product, dry food product, moist food product, a pet food supplement (e.g., vitamins) or combinations thereof. In certain embodiments, the pet food product is a nutritionally complete wet food product.

As used herein, the term "commercially available," when used in conjunction with a pet food, including a cat food, wet cat food, or wet pet food, means available for purchase by a consumer. Commercially available pet foods can be prepared with various ingredients, depending, for example, on the manufacturer and recipe, and the ingredients can be tailored, e.g., to a particular species, age, or breed of pet. For example, commercially available pet foods can contain animal products (e.g., chicken, turkey, beef, pork, lamb, fish, shellfish), animal byproducts, (e.g., organs, liver, giblets, bone marrow), and/or carbohydrates (e.g., fruits, vegetables, rice, potatoes). For further example, commercially available pet food products can further include food additives, e.g., flavor compounds, nutrients, amino acids, vitamins and minerals, bioactives, texturizers, thickening agents, humectants, food coloring agents, bulking agents, hydrocolloids, stabilizers, preservatives, gelling agents, and/or emulsifiers. Additional non-limiting examples of ingredients in commercially available pet foods are provided at www.catinfo.org/docs/FoodChartPublic9-22-12.pdf; which is hereby incorporated by reference in its entirety.

A "chocolate product," as used herein, refers to a solid or semi-plastic food and is intended to refer to all chocolate, chocolate-like and chocolate-flavored compositions containing a fat-based component phase or fat-like composition. The term is intended to include standardized or nonstandardized compositions conforming to the U.S. Standards of Identity (SOI), CODEX *Alimentarius* and/or other international standards and compositions not conforming to the U.S. Standards of Identity or other international standards. The term can include dark chocolate, baking chocolate, sweet chocolate, bittersweet or semisweet chocolate, milk chocolate, buttermilk chocolate, skim milk chocolate, mixed dairy product chocolate, white chocolate, sweet cocoa and vegetable fat coating, sweet chocolate and vegetable fat coating, milk chocolate and vegetable fat coating, vegetable fat based coating, pastels including white chocolate or coating made with cocoa butter or vegetable fat or a combination of these, nutritionally modified chocolate-like compositions (chocolates or coatings made with reduced calorie ingredients) and low fat chocolates, aerated chocolates, compound coatings, non-standardized chocolates and chocolate-like compositions, unless specifically identified otherwise.

As used herein, the term "compound" refers to any chemical entity, species and/or substance present in a complex mixture. The term "compound" can be used synonymously with the term "component." Non-limiting examples of such compounds include precursor flavor compounds, flavor compounds, nutrients, trace metals, pre-biotics, amino acids, peptides, proteins, anti-nutritionals, food additives, undesirable compounds, toxic compounds, impurities, carbohydrates, sugars, polyphenols, oligosaccharides, lipids, fatty acids, minerals, pro-oxidants, antioxidants, and products of a chemical reaction, e.g., products of one or more Maillard reactions. Additional non-limiting examples of compounds include colorants, texturizers, thickening agents, e.g., polysaccharide thickening agents, hydrocolloids, *cassia* gum, alginate and pectin, and emulsifiers. In certain embodiments, the compound can include a nutrient such as, but not limited to, vitamins and co-factors, Vitamin B compounds, thiamine, riboflavin, a Vitamin A compound, functional carbohydrates, retinol and retinol esters, and/or essential nutrients such as choline, taurine, essential fatty acids and essential amino acids.

In certain embodiments, the compound can be an undesirable compound, e.g., a compound that is not desired within the complex mixture or a compound that is banned from being an ingredient in a food product, e.g., a pet food product. For example, and not by way of limitation, an undesirable compound can be a compound that is banned from being an ingredient in a pet food product and/or an ingredient that is regulated by the European Commission, the U.S. Food and Drug Administration (FDA) and/or the European Food Safety Authority (EFSA). Non-limiting examples of such compounds include mycotoxins, e.g., Aflatoxin $B_1$ and Rye ergot, deoxynivalenol, zearalenone, fumonisins $B_1$ and $B_2$, hydrocyanic acid, theobromine, vinyl thiooxazolidone, hexachlorobenzene, hexachlorocyclohexane, polychlorinated dibenzo-para-dioxins (PCDDs), polychlorinated dibenzofurans (PCDFs), polychlorinated biphenyls (PCBs), decoquinate, halofuginone hydrobromide, maduramicin ammonium alpha, diclazuril, lasalocid A sodium, monensin sodium, dioxins, narasin, nicarbazin, robenidine hydrochloride, salinomycin sodium, semduramicin sodium, gentian violet, propylene glycol, 3-monochloropropane-1,2-diol (3-MCPD) and monochloro glycerophosphates. Additional non-limiting examples include polycyclic aromatic hydrocarbons (PAHs) such as benz(a)anthracene, benzo(b)fluoranthene, benzo(j)fluoranthene, benzo(k)fluoranthene, benzo(g,h,i)perylene, chrysene, cyclopenta(c,d)pyrene, dibenz(a,h)anthracene, dibenzo(a,e)pyrene, dibenzo(a,h)pyrene, dibenzo(a,i)pyrene, dibenzo(a,l)pyrene, indeno(1,2,3-cd)pyrene and 5-methylchrysene. Additional non-limiting examples are provided in the Directive 2002/32/EC of the European Parliament and of the Council (May 7, 2002); the European Union Register of Feed Additives pursuant to Regulation (EC) No 1831/2003 (Edition 156; Mar. 6, 2013); http://ec.europa.eu/food/food/animalnutrition/contaminants/index_en.htm; http://www.fda.gov/food/guidanceregulation/guidancedocuments-regulatoryinformatio n/chemicalcontaminantsmetalsnaturaltoxinspesticides/ucm077969.htm; http://www.accessdata.fda.gov/scripts/cdrh/cfdocs/cfCFR/CFRSearch.cfm?CFRPart=589&showFR=1; the contents of which are hereby incorporated by reference in their entireties.

An "essential amino acid," as used herein, refers to an amino acid that cannot be synthesized within the body and must be supplied through diet. Non-limiting examples of essential amino acids can be species dependent. For example, and not by way of limitation, examples of essential amino acids for humans include phenylalanine, valine, threonine, tryptophan, methionine, leucine, isoleucine, lysine and histidine. Essential amino acids for cats include, but are not limited to, arginine, histidine, isoleucine, leucine, lysine, methionine, phenylalanine, threonine, tryptophan, valine and taurine. Essential amino acids for dogs include, but are not limited to, arginine, methionine, histidine, phenylalanine, isoleucine, threonine, leucine, tryptophan, lysine and valine.

As used herein, a "flavor compound" refers to at least one compound or biologically acceptable salt thereof that modulates, including enhancing, multiplying, potentiating, decreasing, suppressing, or inducing, the tastes, smells, flavors and/or textures of a natural or synthetic tastant, flavoring agent, taste profile, flavor profile and/or texture profile in an animal or a human. In certain embodiments, the flavor compound can include an odorant, a volatile compound, a furanone compound, an amino acid, a nucleotide, a transmembrane agonist, a nucleotide derivative, a fatty acid, an agonist of a taste receptor and/or an antagonist of a taste receptor. Non-limiting examples of taste receptors include sweet, sour, salt, bitter, kokumi, fatty acid and umami taste receptors.

As used herein, the term "anti-nutritional" refers to a natural or synthetic compound that can reduce the availability, e.g., interfere with the absorption, of nutrients. Non-limiting examples of an anti-nutritional compound include arabinoxylans, beta-glucans, cyclopropenoid fatty acids, gossypol, L-canavanine, lectins, phytate, protease inhibitors, amylase inhibitors, lipase inhibitors, saponins and tannins.

As used herein, the term "sample" refers to a compound or mixture of compounds obtained from the complex mixture. In certain embodiments, the sample is in aqueous form and comprises one or more compounds that were present within the complex mixture. In certain embodiments, the sample is a fraction, i.e., a portion, of the complex mixture and is obtained by a single extraction step. In certain embodiments, the sample is obtained by a methanol/water extraction step. In certain embodiments, the sample is obtained by Solvent Assisted Flavor Evaporation (SAFE) distillation (see, e.g., Engel, European Food Res. and Tech., 1999, 209(3-4): p. 237-241). In certain embodiments, the sample refers to the aqueous portion of a wet pet food product.

As used herein, the terms "peak intensity" refers to the intensity of an ion corresponding to a peak on a mass spectrum. The mass spectrum can be produced by mass spectrometry. The term "peak intensity" can be used interchangeably with the term "ion intensity."

2. Mass Spectrometry

The presently disclosed subject matter relates to the use of mass spectrometry to analyze the chemical composition of complex mixtures. For example, and not by way of limitation, the presently disclosed subject matter relates to methods for monitoring the changes in the chemical composition of a complex mixture during its production using mass spectrometry.

Mass spectrometers for use in the presently disclosed matter include ultra high resolution mass spectrometers. Ultra high resolution mass spectrometry is an advanced form of mass spectrometry that gives accurate mass data and allows the molecular formula of ions to be determined with a high level of confidence. In particular, ultra high resolution mass spectrometry allows the determination of mass data up to six (6) decimal places. In certain embodiments, the difference between the mass values obtained from the mass spectrometer for two or more compounds can be at least about 0.00001 Da or at least about 0.000001 Da.

By comparison, other forms of mass spectrometry provide mass data with lower mass resolution. The ability of ultra high resolution mass spectrometry to obtain such accurate mass data allows the tentative identification of the thousands of compounds present in complex mixture, e.g., a pet food product, as compared to more conventional mass spectrometry methods such as Time of Flight (ToF)-MS, which only provides molecular weights up to 4 decimal places and which are less able to resolve similar masses. Furthermore, the ability to measure such differences in mass data allows superior resolution and the correct identification of compounds which are very similar in mass that would not have been able to be identified using more traditional methods of mass spectrometry as they would not be resolved. On a conventional mass spectrometer, many ions corresponding to compounds of very similar mass in a complex mixture would not be resolved and would be interpreted by the mass spectrometer as a distribution of a single mass ion, rather than as a number of discrete different species with very similar mass. However, ultra high resolution mass spectrometry allows the ability to resolve chemical compounds that are similar in mass and within the same chemical species in complex samples that would have otherwise appeared as "isobaric" using quadrupole or even conventional ion trap/Time of Flight (ToF) mass spectrometers. In addition, such resolution reduces the need for separation and extensive processing of the sample prior to subjecting the sample to mass spectrometry (e.g., using chromatography).

In certain embodiments, in the methods disclosed herein, the mass spectrum data obtained, e.g., one or more peaks, can be converted to molecular formulas to identify the compounds present within the sample through use of an algorithm. In certain embodiments, the ultra high resolution mass spectrometry used in the disclosed methods allows the identification of at least about 10%, at least about 20%, at least about 30%, at least about 40%, at least about 50%, at least about 60% or at least about 70% of the compounds present in the complex mixture. In certain embodiments, the ultra high resolution mass spectrometer for use in the disclosed methods allows the collection of data at high speeds. For example, and not by way of limitation, data can be collected at rates such as about 10 minutes per sample, about 20 minutes per sample or about 30 minutes per sample.

A non-limiting example of an ultra high resolution mass spectrometer includes a Fourier transform ion cyclotron resonance mass spectrometer (FT-ICR-MS). FT-ICR-MS instruments use cryogenically-cooled, super-conducting magnets to assert precise control over ions and the measurement of their mass to charge ratio (m/z). Non-limiting examples of FT-ICR-MS for use in the presently disclosed subject matter are disclosed in U.S. Pat. Nos. 7,078,684, 7,696,476 and 8,440,966, and PCT Application Nos. WO 2007/030948 and WO 2012/053799, the disclosures of which are incorporated herein by reference. Additional non-limiting examples of ultra high resolution mass spectrometers include Orbitrap mass spectrometers and mass spectrometers available from Thermo Scientific (Somerset, N.J.).

In certain embodiments, prior to being analyzed by mass spectrometry, a sample is subjected to ionization. Non-limiting examples of ionization techniques that can be used with the disclosed methods include Electrospray Ionization (ESI), nano Electrospray Ionization (nanoESI or nano spray), Atmospheric Pressure Chemical Ionization (APCI), Atmospheric Pressure Photo Ionization (APPI), Proton Transfer Reaction Ionization (PTR), "soft ionization," Atmospheric Solids Analysis Probe (ASAP), Selected Ion Flow Tube (SIFT), Direct Analysis in Real Time (DART), Desorption Electrospray Ionization (DESI), and Matrix Assisted Laser Desorption Ionization (MALDI). The selection of an ionization technique can be significant to determining which chemical components are detected using ultra high resolution mass spectrometry. Non-limiting examples of ionization techniques for use in the presently disclosed subject matter are disclosed in Applied Spectroscopy Reviews, Vol. 50(2): 158-175 (2015), which is hereby incorporated by reference in its entirety. In certain embodiments, the ionization technique can be selected to detect certain classes of compounds.

In certain embodiments, the sample is subjected to ESI prior to being subjected to mass spectrometry. In certain embodiments, the ionization technique can be performed in positive and negative ionization modes and different reagents for ionization can be used such as, but not limited to, ESI, proton transfer from water, or other charge transfer reagents. In certain embodiments, the ionization technique is performed in the negative ionization mode using ESI or nanoESI.

In certain embodiments, the mass spectra can be calibrated and filtered to remove signals that have a particular signal to noise ratio. For example, and not by way of limitation, signals that have a signal to noise ratio less than or equal to about 7, less than or equal to about 6, less than or equal to about 5 or less than or equal to about 4 can be removed.

3. Methods of Use

The presently disclosed subject matter provides targeted and untargeted methods for analyzing the chemical composition of complex mixtures. In particular, the presently disclosed subject matter provides methods for analyzing the chemical composition and/or analyzing the changes in the chemical composition of a complex mixture, e.g., a pet food product. For example, and not by way of limitation, the methods of the disclosed subject matter can be used to monitor the chemical composition of a complex mixture during the production process of that complex mixture and/or monitor the chemical reactions, e.g., Maillard reactions, that are occurring during the production of the complex mixture, e.g., pet food product. In certain embodiments, the presently disclosed subject matter further provides methods for monitoring chemical reaction kinetics, e.g., by determining the reaction rate of one or more chemical reactions from changes in the concentration of one or more compounds within the complex mixture. In certain embodiments, the presently disclosed subject matter further provides methods for modulating the process for producing a complex mixture by analyzing the changes in the chemical composition of the complex mixture during production. The presently disclosed subject matter further provides methods and techniques for visualizing and analyzing the information obtained from ultra high resolution mass spectrometry of complex mixtures.

In one aspect, the present disclosure provides methods for identifying the presence of one or more compounds in a complex mixture. In certain embodiments, the method for identifying the presence of a compound in a complex mixture can comprise providing one or more samples of the complex mixture. For example, and not by way of limitation, two or more, three or more, four or more, five or more, six or more, seven or more, eight or more, nine or more or ten or more samples of the complex mixture can be provided. In certain embodiments, about 7 or about 8 samples of the complex mixture are provided. In certain embodiments, about 7 samples of the complex mixture are provided.

In certain embodiments, the sample can comprise a fraction of the complex mixture and/or comprise one or more compounds that are present within the complex mixture. In certain embodiments, the sample can comprise one or more of the compounds present in the complex mixture, e.g., from about one compound to about 12,000 compounds. By way of example, and not limitation, the sample can comprise at least about 1, at least about 2, at least about 3, at least about 4, at least about 5, at least about 6, at least about 7, at least about 8, at least about 9, at least about 10, at least about 20, at least about 30, at least about 40, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1,000, at least about 1,500, at least about 2,000, at least about 2,500, at least about 3,000, at least about 3,500, at least about 4,000, at least about 4,500, at least about 5,000, at least about 5,500, at least about 6,000, at least about 6,500, at least about 7,000, at least about 7,500, at least about 8,000, at least about 8,500, at least about 9,000, at least about 9,500, at least about 10,000, at least about 10,500, at least about 11,000, at least about 11,500 or at least about 12,000 of the compound(s) present in the complex mixture.

In certain embodiments, the methods of the present disclosure can be used to detect and/or identify one or more compounds present within a complex mixture and/or a sample of a complex mixture that has a mass/charge (m/z) ratio up to about 5,000 Da. For example, and not by way of limitation, the methods of the present disclosure can be used to identify a compound that has a m/z ratio of up to about 50 Da, up to about 100 Da, up to about 200 Da, up to about 300 Da, up to about 400 Da, up to about 500 Da, up to about 600 Da, up to about 700 Da, up to about 800 Da, up to about 900 Da, up to about 1,000 Da, up to about 1,100 Da, up to about 1,200 Da, up to about 1,300 Da, up to about 1,400 Da, up to about 1,500 Da, up to about 1,600 Da, up to about 1,700 Da, up to about 1,800 Da, up to about 1,900 Da, up to about 2,000 Da, up to about 2,100 Da, up to about 2,200 Da, up to about 2,300 Da, up to about 2,400 Da, up to about 2,500 Da, up to about 2,600 Da, up to about 2,700 Da, up to about 2,800 Da, up to about 2,900 Da, up to about 3,000 Da, up to about 3,100 Da, up to about 3,200 Da, up to about 3,300 Da, up to about 3,400 Da, up to about 3,500 Da, up to about 3,600 Da, up to about 3,700 Da, up to about 3,800 Da, up to about 3,900 Da, up to about 4,000 Da, up to about 4,100 Da, up to about 4,200 Da, up to about 4,300 Da, up to about 4,400 Da, up to about 4,500 Da, up to about 4,600 Da, up to about 4,700 Da, up to about 4,800 Da, up to about 4,900 Da or up to about 5,000 Da present within the complex mixture and/or a sample of a complex mixture. In certain embodiments, the methods of the present disclosure can be used to identify a compound that has a m/z ratio from about 50 to about 3,000 Da, from about 90 to about 3,000 Da, from about 250 to about 3,000 Da, from about 500 to about 3,000 Da, from about 500 to about 2,500 Da, from about 500 to about 2,000 Da, from about 500 to about 1,500 Da, from about 500 to about 1,000 Da or from about 800 to about 900 Da. In certain embodiments, the methods of the present disclosure can be used to identify a compound that has a m/z ratio from about 50 to about 2,000 Da, from about 90 to about 1,500 Da or from about 90 to about 1,000 Da.

The method can further include performing mass spectrometry on the sample of the complex mixture to obtain a mass spectrum. In certain embodiments, the mass spectrum can provide the accurate and exact mass or mass-to-charge ratio for the compound. In certain embodiments, the method can further include identifying one or more peaks from the mass spectrum that correspond to a compound. For example, and not by way of limitation, the one or more peaks of the mass spectrum can be compared to a database that includes chemical formula and accurate mass data from previously known or predicted compounds to identify the compound present within the complex mixture.

In certain embodiments, the database for use in the presently disclosed methods will include mass spectra or chemical formula for compounds present in food products. For example, and not by way of limitation, the database can include mass spectra for predicted or known Maillard reaction precursors (e.g., reactants), Maillard reaction intermediates (theoretical and/or previously characterized) and Maillard reaction products, volatile compounds, aroma compounds, precursor flavor compounds, undesirable compounds, flavor compounds, taste active compounds, peptides, phosphopeptides, glycosides, lipids, glycopeptides, nucleotides, amino acids, sugars, sugar phosphates, free fatty acids, monoglycerides, diglycerides, triglycerides, phenolic and polyphenolic compounds, colorants, nutrients, essential nutrients, food additives, anti-nutritionals, toxic compounds, anti-oxidants, thickeners, vitamins and emulsifiers.

In certain embodiments, the chemical compounds detected in the complex mixtures by ultra high resolution mass spectrometry can be further analyzed by data interrogation and visualization techniques (such as, but not limited to, through the use of van Krevelen diagrams) to identify whether a chemical reaction occurred during the production of the complex mixture. Non-limiting examples of data visualization and interrogation techniques are described below.

In certain embodiments, the disclosed method can be used to determine the identity of the raw materials used to produce the complex mixture by identifying components present in the complex mixture. For example, and not by way of limitation, the identification of a compound in the complex mixture that is a product or intermediate of the Maillard reaction can be used to determine the raw materials that reacted to form the product of the Maillard reaction, i.e., the Maillard precursor compounds (see, for example, FIGS. 20 and 21). In certain embodiments, the identification of one or more compounds in the complex mixture can be indicative of certain raw materials. For example, the disclosed method can identify certain free fatty acids characteristic of particular species (e.g., Docosahexaenoic acid and/or Eicosapentaenoic acid which can indicate that fish or fish oil was used as a raw material, or branched chain fatty acids which can indicate that a ruminant was used as a raw material). As a further example, the disclosed method can identify certain bile salts and/or bile acids which can indicate that certain organs (e.g., organs involved in digestion) were used as raw materials. In certain embodiments, the complex mixture can be a commercially available food product and/or a product obtained after a thermal process.

The presently disclosed subject matter further provides methods for identifying the presence of a food additive in a complex mixture. Non-limiting examples of food additives include flavors and/or flavor compositions, e.g., hydrolysates, yeast extracts and amino acids; nutrients; amino acids; vitamins and minerals; bioactives, e.g., essential oils and anti-microbials; texturizers; thickening agents, e.g., alginin, guar gum, xanthum gum, cellulose gum, *cassia* gum and hydroxypropyl cellulose; humectants, e.g., glycerine; food coloring agents; bulking agents; hydrocolloids; stabilizers; preservatives, e.g., propionates, nitrates and nitrites; gelling agents, e.g., agar, alginate, gelatin and pectin; and emulsifiers, e.g., sodium phosphates, bile acids, lecithin and diglycerides. In certain embodiments, the method can comprise providing a sample of the complex mixture. In certain embodiments, the methods can further include performing mass spectrometry on the sample of the complex mixture to obtain a mass spectrum and identifying one or more peaks from the mass spectrum that correspond to the food additive, e.g., emulsifier. For example, and not by way of limitation, the sample can be obtained from a pet food product, e.g. a commercially available pet food product, and, in certain embodiments, the identification of an emulsifier in the pet food product can be used to identify the raw materials used to produce the pet food product.

The present disclosure further provides methods for analyzing changes in the chemical composition of a complex mixture. For example, and not by way of limitation, the methods disclosed herein can be used to analyze the changes in the amount of one or more compounds present in the complex mixture during the production process of the complex mixture by analyzing the mass spectra of two or more samples obtained during the production process. In certain embodiments, the mass spectra of three or more, four or more, five or more, six or more, seven or more or eight or more samples of the complex mixture can be analyzed and the changes in the chemical composition of the samples and/or the changes in the amount of a compound within the samples can be determined.

In certain embodiments, the method for analyzing changes in the chemical composition of a complex mixture can comprise providing one or more samples of the complex mixture. For example, and not by way of limitation, two or more, three or more, four or more, five or more, six or more, seven or more, eight or more, nine or more or ten or more samples can be provided. In certain embodiments, the method can comprise providing seven samples of a complex mixture. In certain embodiments, the method can comprise providing a first sample and a second sample of a complex mixture. In certain embodiments, the samples can be obtained from a single production batch of a complex mixture and/or obtained during the production of a single batch of the complex mixture. Alternatively or additionally, the method can comprise providing samples from multiple production batches of a complex mixture, e.g., providing one or more samples of a first production batch of a complex mixture and one or more samples of a second production batch of the complex mixture.

The method can further comprise performing mass spectrometry on the one or more samples to obtain one or more mass spectra. For example, and not by way of limitation, the method can comprise performing mass spectrometry, e.g., by using an ultra high resolution mass spectrometer, on a first sample of the complex mixture to obtain a first mass spectrum. In certain embodiments, the method can comprise performing mass spectrometry on a second sample of the complex mixture to obtain a second mass spectrum. To determine the relative changes in the amount of the compound between the samples, the method can further include determining the intensity of one of more peaks in the first mass spectrum that corresponds to the compound and comparing the intensity of the one or more peaks in the first mass spectrum to the intensity of the one of more peaks in the second mass spectrum that correspond to the compound. For example, and not by way of limitation, an increase in the amount of a compound in the second sample will be indicated by a peak with a greater intensity in the second mass spectrum compared to the same peak in the first mass spectrum.

In certain embodiments, the one or more samples, e.g., first and second samples, can be obtained at different time points during production of the complex mixture. For example, and not by way of limitation, the complex mixture can be a food product, and the first and second samples can be obtained at different time points during production of the food product. Alternatively, the first sample can be a sample of a first production batch of the complex mixture and the second sample can be a sample of a second production batch of the complex mixture. In certain embodiments, the food product can be a pet food product such as a wet pet food product, where the wet pet food product undergoes a severe heating process to ensure safety of the product. For example, and not by way of limitation, the wet pet food product can undergo a thermal heating process, i.e., sterilization process, at a temperature of about 110° C. to about 140° C. for about 10 to about 50 minutes. In certain embodiments, the first sample can be obtained prior to sterilization of the food product and the second sample can be obtained during or after the sterilization of the food product. Alternatively or additionally, the first sample can be obtained during sterilization of the food product and the second sample can be obtained at a later time point during the process or after sterilization of the food product is complete.

In certain embodiments, two or more samples, e.g., first and second samples, can be obtained from multiple production batches of a complex mixture. For example, and not by way of limitation, a first sample can be obtained from a first production batch and a second sample can be obtained from a second production batch. The first and second production batches can produce the same or different complex mixtures (e.g., food products). In certain embodiments, the first and second production batches can produce the same complex mixture. Mass spectrometry can be performed on the first and second samples to obtain mass spectra. The methods described above can be used to determine the differences in the amounts of chemical compounds between the two samples using the mass spectra. In certain embodiments, the multiple production batches can be produced under the same conditions, e.g., to analyze the consistency in complex mixtures between multiple production batches. In certain other embodiments, various parameters can be altered between the multiple production batches, e.g., to determine the effect (if any) on chemical composition. For example, the multiple production batches can originate from different factories or be subject to different thermal processing. For further example, raw materials can be sourced from different providers, can have different qualities, or can have other variations, e.g., based on seasonality.

Alternatively or additionally, a first sample can be compared against a reference sample, e.g., using the methods described above. The reference sample can have a known chemical composition. For example, the reference sample can be a quality control sample having a standard or target chemical composition. In certain embodiments, the first sample and the quality control sample can be compared to identify deviations from a standard or target chemical composition. The method can include performing mass spectrometry on the first sample and the reference sample to obtain mass spectra. In certain embodiments, the mass spectrometry can be performed for both the first sample and the reference sample at the same time. In other certain embodiments, the mass spectra of the first sample can be compared to an existing mass spectra of a reference sample.

The method can further include performing mass spectrometry on a control sample at the same time as the first sample, and comparing the mass spectra obtained from the control sample to an existing mass spectra of the control sample created at an earlier point in time to analyze the consistency of the mass spectrometry over time.

The presently disclosed subject matter further provides methods for determining the occurrence of a chemical reaction during production of a complex mixture. In certain embodiments, the production process, e.g., heating process, can promote the occurrence of chemical reactions between components present in the food product, which in turn can result in an increase in the presence of chemical reaction products in the food product. In certain embodiments, the chemical reaction can result in the presence of a beneficial compound within the complex mixture, e.g., a desirable flavor compound or precursor flavor compound. Alternatively, the chemical reaction can result in the presence of an undesirable compound within the complex mixture and/or can result in the degradation of beneficial nutrients, e.g., vitamins, within the complex mixture.

In certain embodiments, the method for determining the occurrence of a chemical reaction during production of a complex mixture can comprise providing one or more samples of the complex mixture, wherein the samples are obtained at different time points during the production process of the complex mixture. For example, and not by way of limitation, the method can comprise providing a first sample and a second sample of the complex mixture, wherein the first sample is obtained prior to the second sample during a process of producing the complex mixture. The method can comprise performing mass spectrometry on the first sample of the complex mixture to obtain a first mass spectrum and performing mass spectrometry on the second sample of the complex mixture to obtain a second mass spectrum. In certain embodiments, the method further comprises comparing one or more peaks of the first mass spectrum corresponding to a compound to one or more peaks of the second mass spectrum corresponding to a chemical reaction product of the compound to determine the occurrence and/or prevalence of a chemical reaction. As indicated above, the one or more peaks of the mass spectrum can be compared to a database that includes chemical formula and accurate mass data from previously known or predicted compounds to identify a compound present within the complex mixture, e.g., by identifying the one or more peaks in the first mass spectrum. In addition, in certain embodiments, the method can include predicting the chemical formula of the chemical reaction product and identifying one or more peaks that correspond to that chemical reaction product within the mass spectra of the second mass spectrum.

Alternatively or additionally, the methods of the disclosed subject matter can be used to monitor the increase and/or decrease in the presence of compounds in the complex mixture that are products, precursors (e.g., reactants) or intermediates of chemical reactions. For example, and not by way of limitation, the method can further include comparing one or more peaks of the first mass spectrum corresponding to a chemical reaction product to one or more peaks of the second mass spectrum corresponding to the chemical reaction product to determine whether the product increases during the production of the complex mixture. In certain embodiments, the method of the disclosed subject matter can be used to monitor the increase and/or decrease in the presence of compounds that are reactants of chemical reactions. For example, and not by way of limitation, the method can include comparing one or more peaks of the first mass spectrum corresponding to a compound that is a reactant of a chemical reaction to one or more peaks of the second mass spectrum corresponding to the compound to determine whether the level of the reactant decreases during the production of the complex mixture, which can indicate that the reactant is being consumed by the chemical reaction during the production of the complex mixture. By analyzing the changes in the presence of a compound that is a reactant of a chemical reaction between the first sample and second sample and/or analyzing the changes in the presence of a compound that is a product of the chemical reaction, one could determine the occurrence and/or prevalence of the chemical reaction during the production of the complex mixture.

In certain embodiments, methods for determining the occurrence of chemical reactions during production of a complex mixture can comprise adding an isotopically labeled compound, e.g., a potential chemical reactant, at the beginning of the production of the complex mixture. For example, and not by way of limitation, the isotopically labeled compound can be enriched with a low abundance stable isotope, e.g., $^2$H (deuterium), $^{13}$C (carbon-13), $^{15}$N (nitrogen-15), $^{18}$O (oxygen 18) or $^{34}$S (sulfur-34). In certain embodiments, the method can further include providing two or more samples of the complex mixture, wherein the samples are obtained at different time points during the production process of the complex mixture, e.g., one of the samples is obtained at the beginning of the production process and the second sample is obtained during the middle of the production process or at the end of the production process. In certain embodiments, the first sample of the complex mixture is subjected to mass spectrometry to obtain a first mass spectrum and the second sample of the complex mixture is subjected to mass spectrometry to obtain a second mass spectrum. In certain embodiments, one or more peaks of the first mass spectrum corresponding to a compound that is labeled with an isotope is compared to one or more peaks of the second mass spectrum corresponding to the compound that is labeled with the isotope to determine the occurrence and/or prevalence of a chemical reaction that involved the compound that was isotopically labeled. For example, and not by way of limitation, such methods can be used to identify the occurrence of Maillard reactions during the production, e.g., sterilization, of a complex mixture by the addition of isotopically labeled precursors with the raw materials at the beginning of the production process, e.g., sterilization process, of the complex mixture and the identification of isotopically labeled Maillard reaction products that are present in the complex mixture during and/or at the end of the production process, e.g., sterilization process.

In certain embodiments, the chemical reactions that can be monitored using the disclosed methods include, but are not limited to, Maillard reactions, condensation reactions, hydrolysis reactions, hydration reactions, elimination reactions, oxidation reactions, decarboxylation reactions, sulfuroxygen exchange reactions, amination reactions, reactions involving disulfide bond formation or cleavage, deamination reactions, transamination reactions, reduction reactions, redox reactions, nucleophilic substitution reactions, nucleophilic addition reactions, electrophilic aromatic substitution reactions, glycosylation reactions, or phosphorylation reactions.

In certain embodiments, the type of reaction(s) taking place during the production of a chemical mixture and/or during the storage of a chemical mixture can be assessed by identifying all the compounds that differ by a specific mass difference. For example, and not by way of limitation, the addition of a water molecule (which has a mass of about 18 Daltons (Da) and, in its most abundant isotopomer, a characteristic exact mass of 18.010565 Da) can be indicative of a hydration reaction, and the loss of a water molecule can be indicative of a dehydration reaction. In certain embodiments, the phosphorylation of a sugar by the addition of a phosphate group (effectively adding $HPO_3$, which has a mass of about 80 Da and, in its most abundant isotopomer, a characteristic exact mass of 79.966333 Da) to a sugar is indicative of phosphorylation. In certain embodiments, the loss of $CO_2$ (which has a mass of about 44 Da and, in its most abundant isotopomer, a characteristic exact mass of 43.989830 Da) is indicative of a decarboxylation reaction and the addition of an oxygen (which has a mass of about 16 Da and, in its most abundant isotope, a characteristic exact mass of 15.994915 Da) or loss of two hydrogens ($H_2$; which has a mass of about 2 Da and, in its most abundant isotopomer, a characteristic exact mass of 2.015650 Da) represents an oxidation reaction. In certain embodiments, reduction reactions can include, but are not limited to, the addition of one or more hydrogens and/or the removal of one or more oxygens. In certain embodiments, an elimination reaction can include the loss of a moiety and/or a chemical group from a compound. For example, and not by way of limitation, the loss of an amino acid from a compound, can be indicative of an elimination reaction, e.g., such as an elimination reaction that occurs during a Maillard reaction. In certain embodiments, an addition reaction can include the addition of a moiety and/or a chemical group to a compound. For example, and not by way of limitation, the addition of an amino acid to a compound, e.g., a sugar, can be indicative of an addition reaction, e.g., such as an addition reaction that occurs during a Maillard reaction.

In certain embodiments, the disclosed methods can include identifying a compound in a first sample (e.g., by analyzing the mass spectrum of the first sample) of a complex mixture and identifying a second compound in a second sample (e.g., by analyzing the mass spectrum of the second sample) that differs from the first compound by a specific mass difference, as described above. The identification of such compounds can be indicative that a chemical reaction is occurring during the production of the complex mixture. In certain embodiments, the method can further include comparing the levels of the two compounds present in the first and the second samples to determine whether the levels of such compounds change during the production of the chemical mixture. For example, and not by way of limitation, if the level of the first compound decreases in the second sample as compared to the first sample and the level of the second compound increases in the second sample as compared the first sample, it is predicted that the chemical reaction that consumes the first compound to produce the second compound is occurring during the chemical mixture production process.

In addition to determining the occurrence of and monitoring chemical reactions, the disclosed subject matter provides methods of monitoring chemical reaction kinetics. For example, in certain embodiments, methods can include monitoring or determining the concentration of one of more chemical compounds and/or the reaction rate of one or more chemical reactions. The reaction rates of chemical reactions occurring within a complex mixture can be determined experimentally from changes in the concentration of one or more compounds within the complex mixture, and in particular from the rate of change in concentration of one or more compounds that are reactants, products, or intermediates in the chemical reactions. See, e.g., Gordon G. Hammes, *Principles of Chemical Kinetics*, Chapter 1—Empirical Analysis of Reaction Rates, Academic Press: London, 1978, which is hereby incorporated by reference in its entirety.

A rate of change in the concentration of a compound can be determined using the methods described above. For example, and not by way of limitation, the method can comprise performing mass spectrometry, e.g., by using an ultra high resolution mass spectrometer, on a first sample of the complex mixture to obtain a first mass spectrum and performing mass spectrometry on a second sample of the complex mixture to obtain a second mass spectrum. The method can further include determining the change in the concentration of one or more chemical compounds between the first sample and the second sample, for example, by determining the intensity of one of more peaks in the first mass spectrum that corresponds to the one or more compounds and comparing the intensity of the one or more peaks in the first mass spectrum to the intensity of the one of more peaks in the second mass spectrum that correspond to the one or more compounds. By way of example, the rate of change can be determined from the concentrations and the time elapsed between taking the two samples. The rate of change in the concentrations of one or more compounds can be used to determine the reaction rate of one or more chemical reactions. Additional mass spectra can be obtained from further samples of the complex mixture to refine the rate of change. Obtaining and comparing mass spectra from more than two samples can provide a more precise determination of the reaction rate. In certain embodiments, mass spectra from at least three, at least four, or at least five different samples can be obtained and compared to determine the rate of change in the concentrations of one or more compounds.

In certain embodiments, methods can include determining a reaction rate by measuring the rate of change in the concentration of one or more compound as a reaction proceeds (see, e.g., FIGS. 15C, 15D, 21C, 21E, 21G, and 21I). Thus, both the first sample and the second sample can be taken from the same complex mixture, but at different points during the processing of the complex mixture. For example, the first sample can be taken from an earlier point in processing than the second sample. The rate of change in the concentration of one or more compounds in the complex mixture can be used to determine the rate of a reaction that occurs during the processing of the complex mixture.

In certain other embodiments, methods can include determining a reaction rate by measuring the rate of change in concentration of a compound in a complex mixture after the complex mixture is processed at different temperatures. For example, a first complex mixture can be processed at a first temperature, and a second complex mixture can be processed at a second temperature. The first complex mixture and the second complex mixture can have the same composition. The method can include determining the rate of change in concentration of a compound in the first complex mixture and determining the rate of change in concentration of the compound in the second complex mixture. The method can further include comparing the rate of change in concentration of the compound in the first complex mixture and second complex mixture, e.g., to determine the effect of temperature on the rate of change. These methods can be used to determine the effect of temperature on reaction rate to obtain a better understanding of the chemical reaction kinetics.

In still other embodiments, methods can include determining a reaction rate by measuring the effect on the rate of change in the concentration of a first compound of changing the concentration of a second compound within a complex mixture. For example, and not limitation, the first compound can be a target compound, and the second compound can be involved in the formation or onward reaction of said target compound. The rate of change in concentration of the first compound can be determined for a first complex mixture and a second complex mixture, where the second complex mixture has a different concentration of the second compound than the first complex mixture. The concentration of the second compound can be either increased or decreased, and the effect of the increase or decrease on the rate of change in the concentration of the first compound can be used to determine the effect of the second compound on the reaction rate of a chemical reaction involving the first compound.

Figure 18:
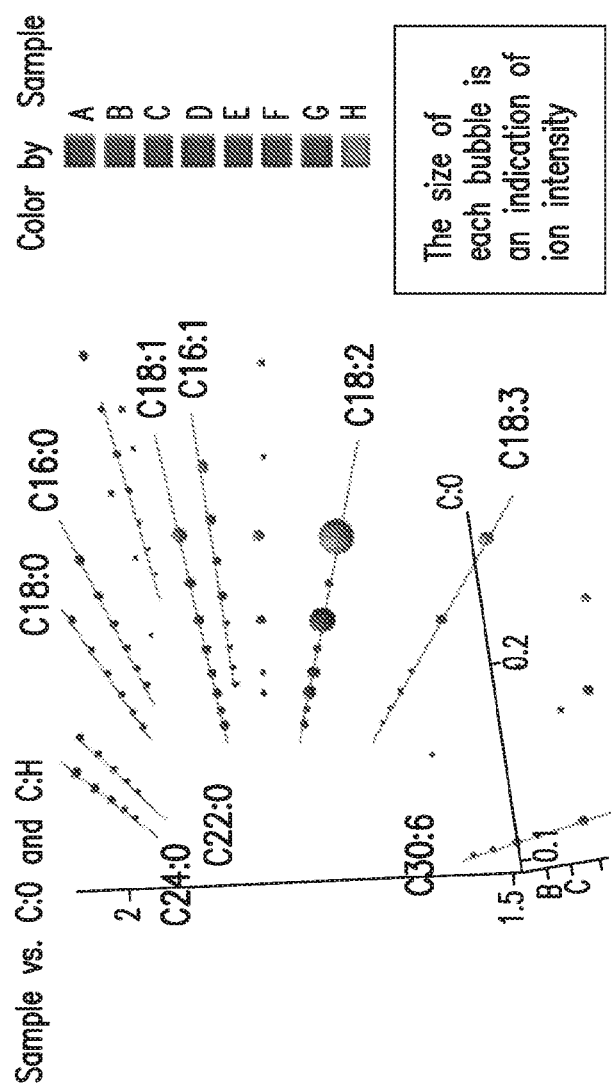
FIG. 18. Van Krevelen diagram that depicting the differences in the chemical compositions of fatty acids in 8 different pet food products.

In certain embodiments, methods of monitoring chemical reaction kinetics can include determining the reaction rates of two or more steps of a multicomponent or stepwise reaction and determining the reaction rate of the multicomponent or stepwise reaction therefrom. Additionally, determining a reaction rate can be used to indicate that a chemical compound, such as a reaction intermediate, is in steady state. For example, a chemical compound in steady state will have a constant concentration over time (see FIG. 18, fatty acids C16:0 and C18:0).

In certain embodiments, the reaction rate can be determined for a chemical reaction including, but not limited to, Maillard reactions (see FIGS. 15C, 15D, 21C, 21E, 21G, and 21I), a condensation reaction, an elimination reaction, a hydrolysis reaction, a dehydration reaction (see FIGS. 21E and 21I), an oxidation reaction, a decarboxylation reaction, a sulfur-oxygen exchange reaction, an amination reaction, a reaction involving disulfide bond formation or cleavage, a deamination reaction, a transamination reaction, a reduction reaction, a redox reaction, a nucleophilic substitution reaction, a nucleophilic addition reaction (see FIGS. 21C and 21G), an electrophilic aromatic substitution reaction, a glycosylation reaction and/or a phosphorylation reaction.

The presently disclosed subject matter further provides methods for altering the presence of a compound within a complex mixture. In certain embodiments, the presently disclosed subject matter provides methods for determining how to change the level of one or more compounds within a complex mixture by identifying chemical pathways that can be altered to result in a change in the level of a compound within the complex mixture. For example, and not by way of limitation, a chemical pathway can be altered by modifying the concentrations of the reactants present in the raw materials and/or by adding additional components that may preferentially react with the reactants to form other compounds. To provide one non-limiting example, the occurrence of acrylamide (which is considered to be a potential carcinogen) in a complex mixture can be reduced or eliminated, e.g., by altering the relative levels of certain amino acids and/or changing process temperature and/or providing a reducing sugar. See, e.g., Food Additives and Contaminants, Vol. 24: 13-25 (2007), Lwt-Food Science and Technology, Vol. 39(7): 724-728 (2006), and Journal of Agricultural and Food Chemistry, Vol. 57(19): 9011-9015 (2009), which are hereby incorporated by reference in their entireties.

In certain embodiments, the methods can further include monitoring the altered chemical pathway during the production of the complex mixture, e.g., by producing a second batch of the complex mixture, to analyze the resulting levels of the compound. For example, the method can include analyzing a reduction or an increase in the compound in the complex mixture.

In certain embodiments, the methods of the disclosed subject matter can be used to reduce the presence of a compound within the complex mixture. Alternatively or additionally, the methods of the disclosed subject matter can be used to increase the presence of a compound within the complex mixture. For example, and not by way of limitation, the method can comprise providing a first sample and a second sample of the complex mixture, wherein the first sample is obtained prior to the second sample during a process of producing the complex mixture. In certain embodiments, the method can further comprise performing mass spectrometry on the first sample of the complex mixture to obtain a first mass spectrum and performing mass spectrometry on the second sample of the complex mixture to obtain a second mass spectrum. In certain embodiments, the method can further comprise comparing one or more peaks of the first mass spectrum corresponding to the compound to one or more peaks of the second mass spectrum corresponding to the compound to determine the amount of the compound within the second sample as compared to the amount of the compound in the first sample. In certain embodiments, the method can further include identifying the occurrence of a chemical reaction that consumes and/or generates the compound during the production process. In certain embodiments, the method can further comprise modulating the process of producing the complex mixture, e.g., by altering a chemical reaction pathway, to reduce the amount of the compound in the complex mixture. Alternatively, the method can comprise modulating the process of producing the complex mixture to increase the presence of the compound within the complex mixture. By way of non-limiting example, modulating the process can include varying certain process parameters, e.g., varying temperature, pressure, process time, flow rate, stoichiometry, concentration of various process components, e.g., starting materials, at the beginning, etc. In certain embodiments, the method can further include analyzing a reduction or increase of the compound within the complex mixture. For example, the method can include monitoring the composition of the complex mixture produced by the modulated production process, e.g., by using mass spectrometry as described above. A reduction or increase in the compound can be analyzed by comparing the composition of the complex mixture prior to modulating the process with the composition of the complex mixture after modulation.

In certain embodiments, the methods of the presently disclosed subject matter can be used to monitor the chemical composition of a complex mixture during its production process, which can, in turn, be used to inform how the production process can be modified to reduce or increase the presence of one or more compounds in subsequent batches (e.g., lots) of the complex mixture. For example, and not by way of limitation, the method for reducing or increasing the presence of a compound within a complex mixture can comprise providing a first sample, a second sample and a third sample of one or more batches of a complex mixture. The method can further include performing mass spectrometry on the first sample of the complex mixture to obtain a first mass spectrum and performing mass spectrometry on the second sample of the complex mixture to obtain a second mass spectrum. In certain embodiments, the method can further comprise comparing one or more peaks of the first mass spectrum corresponding to the compound to one or more peaks of the second mass spectrum corresponding to the compound to determine the amount of the compound within the second sample as compared to the amount of the compound in the first sample. In certain embodiments, the method can further comprise modulating the process of producing the complex mixture to reduce or increase the amount of the compound in the third sample of the complex mixture. In certain embodiments, the first sample and second sample are samples from the same production batch of the complex mixture. By way of non-limiting example, the first sample can be obtained prior to the second sample during a process of producing the complex mixture. In certain embodiments, the third sample can be obtained from a later time point during the production process of the complex mixture than the second sample. Alternatively, in certain embodiments, the third sample can be obtained from a second production batch of the complex mixture, and the analysis of the first and second samples can inform the modulation of the production process used to generate the second production batch. The modulation of the production process can then result in a change in the amount of the compound present in the third sample. The use of the disclosed method would allow the modulation of the production process to reduce the presence and/or increase the presence of a compound within a complex mixture during a single production process or in further production processes.

In certain embodiments, where the method is being used for reducing the presence of a compound within the complex mixture, the compound can be a toxic compound, a vitamin degradation product, a pro-oxidant, an undesirable compound, an undesirable flavor compound or precursor flavor compound, an impurity or combinations thereof. In certain embodiments, such methods can be used to determine whether certain compounds are present within the complex mixture after the production process at the proper levels. For example, and not by way of limitation, the disclosed method can be used to determine whether undesirable compounds in the complex mixture are present at levels below the maximum level allowed in a food product, e.g., as determined by the FDA.

In certain embodiments, where the method is being used for increasing the presence of a compound within the complex mixture, the compound can be a vitamin, nutrient, a peptide, an antioxidant, a flavor compound or combinations thereof. For example, and not by way of limitation, the process of producing the complex mixture can be modulated to result in an increase in the flavor profile and/or palatability of the complex mixture. In certain embodiments, the process of producing the complex mixture can be modulated to result in an increase in the presence of a flavor compound in the complex mixture. In certain embodiments, such methods can be used to determine whether certain compounds are present within the complex mixture at the proper levels upon completion of the production process. For example, and not by way of limitation, the disclosed method can be used to determine whether a pet food product includes the proper level of nutrients as set out in the Association of American Feed Control Officials (AAFCO) Nutritional Standards, e.g., in the AAFCO 2015 Official Publication, or the European Pet Food Industry Federation (FEDIAF) Nutritional Guidelines, available at http://www.fediaforg/self-regulation/nutrition/.

In certain embodiments, the methods disclosed above can be used to identify compounds present during one or more steps of cocoa bean processing and/or peanut processing. The present disclosure further provides methods for identifying compounds that change in quantity and/or for identifying chemical reactions that occur during one or more steps of cocoa bean processing and/or peanut processing. For example, and not by way of limitation, one or more samples analyzed in the methods disclosed above can be obtained during one or more steps of cocoa bean processing and/or peanut processing. For cocoa bean processing, such steps include, but are not limited to, the fermentation of the cocoa beans, the drying of the cocoa beans, the roasting of the cocoa beans, the conching of the cocoa beans, the storage of the cocoa pods and the separation of the cocoa beans from the cocoa pod. For peanut processing, such steps include, but are not limited to, peanut roasting and peanut grinding.

In certain embodiments, the presently disclosed subject matter provides methods for determining the level of cocoa bean roasting or peanut roasting by monitoring the presence of one or more compounds that are indicators of proper cocoa bean roasting or peanut roasting. In certain embodiments, the presently disclosed subject matter provides methods for determining the level of fermentation of cocoa beans by monitoring the presence of one or more compounds that are indicators of cocoa bean fermentation, e.g., a fermentation product. In certain embodiments, the method can comprise providing a first sample and a second sample of fermented cocoa beans, wherein the first sample is obtained prior to the second sample during a cocoa bean fermentation process. In certain embodiments, the method can further comprise performing mass spectrometry on the first sample of the fermented cocoa beans to obtain a first mass spectrum, performing mass spectrometry on the second sample of the fermented cocoa beans to obtain a second mass spectrum and comparing one or more peaks of the first mass spectrum corresponding to a cocoa bean fermentation product to one or more peaks of the second mass spectrum corresponding to the cocoa bean fermentation product to determine the level of cocoa bean fermentation. In certain embodiments, the first sample is obtained prior to cocoa bean fermentation or immediately after initiation of fermentation and the second sample is obtained at a later timepoint during the fermentation process. In certain embodiments, the cocoa bean fermentation product can be a sugar molecule, fat molecule, peptide, protein, flavor precursor compound or combinations thereof. In certain embodiments, the cocoa bean fermentation product can be a compound that is present at high levels at the end of the fermentation process.

The presently disclosed subject matter further provides methods for determining the level of lipid oxidation and/or monitoring decreases and/or increases in lipid levels that occur during production of a complex mixture. For example, and not by way of limitation, such decreases and/or increases in lipid levels may be due to oxidation and/or hydrolysis of the lipids. In certain embodiments, the method can comprise providing a first sample and a second sample of the complex mixture, wherein the first sample is obtained prior to the second sample during a process of producing the complex mixture. In certain embodiments, the methods can further include performing mass spectrometry on the first sample of the complex mixture to obtain a first mass spectrum, performing mass spectrometry on the second sample of the complex mixture to obtain a second mass spectrum and comparing one or more peaks of the first mass spectrum corresponding to a product of lipid oxidation to one or more peaks of the second mass spectrum corresponding to the product to determine the level of lipid oxidation and/or lipolysis in the complex mixture.

The presently disclosed subject matter further provides a method for determining the level of protein hydrolysis during production of a complex mixture. In certain embodiments, the methods can be used to monitor the generation of peptides and/or amino acids during the production of a complex mixture, which can be used to monitor the level of protein hydrolysis. The disclosed methods allow the determination of whether a protein present in a food product, e.g., pet food product, is hydrolyzed and/or degraded during processing of the food product, e.g., sterilization. In certain embodiments, the method can comprise providing a first sample and a second sample of the complex mixture, wherein the first sample is obtained prior to the second sample during a process of producing the complex mixture. In certain embodiments, the method can further comprise performing mass spectrometry on the first sample of the complex mixture to obtain a first mass spectrum, performing mass spectrometry on the second sample of the complex mixture to obtain a second mass spectrum and comparing one or more peaks of the first mass spectrum corresponding to a peptide from a hydrolyzed protein to one or more peaks of the second mass spectrum corresponding to the peptide to determine the level of protein hydrolysis in the complex mixture. For example, but not by way of limitation, measuring the level of hydrolysis of proteins within the complex mixture, which can be used to determine the digestibility of the complex mixture.

The presently disclosed subject matter further provides methods for analyzing the stability of a complex mixture, e.g., a pet food product, during storage and/or packaging conditions. For example, and not by way of limitation, the method can comprise providing a complex mixture and adding an isotopically labeled compound to the complex mixture. In certain embodiments, the isotopically labeled compound can be added to the complex mixture after production of the complex mixture and/or just prior to storage of the complex mixture. In certain embodiments, the method can further include subjecting the complex mixture to a certain storage period and/or subjecting the complex mixture to certain storage conditions and/or packaging conditions, and providing one or more samples of the complex mixture after the certain storage period and/or storage conditions. The one or more samples can then be subjected to mass spectrometry to generate one or more mass spectra. One or more peaks of the mass spectrum that correspond to the isotopically labeled compound can be compared to one or more peaks of a mass spectra that correspond to the isotopically labeled compound from a sample of the complex mixture that was obtained prior to the storage of the complex mixture. Such methods can determine the effect that storage conditions and/or time periods have on the stability of the complex mixture and its chemical components.

4. Complex Mixture Production and Sample Preparation

In certain embodiments, the complex mixtures analyzed by the disclosed methods can be produced in a factory-scale process or a lab-scale reactor. In certain embodiments, the complex mixture is produced in a lab-scale reactor (See Example 1). In certain embodiments, the lab-scale reactor can allow sampling of a complex mixture, e.g., a liquid phase of a food product, during a production process. For example, and not by way of limitation, the production process can occur in a 600 gram lab-scale reactor to mimic factory-scale production processes. In certain embodiments, the time and/or temperature profiles of the lab-scale reactor can be aligned with that from the factory-scale process and the complex mixture can be made in the lab-scale reactor using the same raw materials used in the factory-scale production process (see FIG. 1). The chemical profile of complex mixtures obtained from the lab-scale reactor and factory processes can be analyzed and compared to determine that the profiles are identical or nearly identical (see, for example, FIGS. 2-3). Non-limiting examples of the lab-scale system for use in the disclosed methods include systems manufactured by Parr Instrument Co. (Moline, Ill.).

Samples analyzed by the disclosed methods can be prepared according to any method known in the art. As disclosed above, in certain embodiments, the sample can be prepared to include one or more compounds from the complex mixture. For example, and not by way of limitation, the sample can be prepared to include from about 1 compound to about 12,000 compounds from the complex mixture (as disclosed above). In certain embodiments, a sample can be prepared by performing a simple extraction with a solvent, e.g., water, and/or an organic solvent, e.g., an alcohol, or a water/organic solvent mixture. Non-limiting examples of water/organic solvent mixtures include mixtures of acetone and water and mixtures of ethanol and water. In certain embodiments, the sample can be prepared via a simple aqueous methanolic extraction, i.e., a water/methanol extraction step. In certain embodiments, the ratio of methanol to water during methanolic extraction can be from about 95:5 MeOH:$H_2O$ to about 5:95 MeOH:$H_2O$. In another embodiment, the ratio of methanol to water is about 1:1 MeOH:$H_2O$.

By using particular extraction methods, the samples analyzed in the disclosed method can be prepared in such a way so as to include particular types of compounds, e.g., chemical classes, from the complex mixture. For example, lipids and other fats, e.g., triglycerides, can be removed from the sample using a hydrophobic solvent immiscible with water. Non-limiting examples of such immiscible solvents include pentane, hexane, methyl tert-butyl ether (MTBE), chloroform and dichloromethane. Immiscible solvents can be used alone or in a mixture with methanol, dichloromethane or combinations thereof. The use of such hydrophobic solvents can result in the removal of fats, e.g., triglycerides, from the sample, while retaining free fatty acids, which can, in turn, be analyzed by the disclosed methods. In certain embodiments, the sample can be prepared to specifically include volatile compounds. By way of example, and not by limitation, the sample can be concentrated for volatile compounds by using diethyl ether and/or Solvent Assisted Flavor Evaporation (SAFE) distillation. See, e.g., Engel, European Food Res. and Tech., 1999, 209(3-4): p. 237-241, which is incorporated by reference herein in its entirety.

In certain embodiments, following methanolic extraction, the sample can include, but is not limited to, alcohols, amines, amino acids, peptides, phosphopeptides, glycopeptides, diketopiperazines, pyrazines, furanones, sulfur containing compounds, sulfonic acids, phosphates, sugar phosphates, sugars, glycosides, saccharides, oligosaccharides, sugar degradation products, sterols, free fatty acids, mono glycerides, di glycerides, fatty acid oxidation products, vitamins, nutrients, Maillard reaction precursors, Maillard reaction intermediates, Maillard reaction products, nucleosides, nucleotides, purines (bases), pyrimidines, nucleotide diphosphates, nucleotide triphosphates, phenolic compounds and vitamins.

In certain embodiments, the sample can be further processed after extraction. For example, the sample can be filtered using molecular weight cut off filters or can be subjected to a chromatography step. Non-limiting examples of chromatography include ion exchange chromatography, such as anion exchange chromatography and cation exchange chromatography, size exclusion chromatography, hydrophobic interaction chromatography (HIC), hydrophobic interaction liquid chromatography (HILIC), reversed phase and normal phase chromatography (including high performance liquid chromatography (HPLC) and ultra high performance liquid chromatography (UPLC)) and solid phase extraction (SPE). Such processing techniques can be used to remove compounds from the sample (e.g., salts, high molecular weight compounds, free fats, etc.) and/or can be used to fractionate the sample into different chemical classes prior to analysis using the disclosed methods. Alternatively, in certain embodiments, sample preparation includes a single extraction step, e.g., a single water/methanol step, and no further processing is required prior to analysis in the mass spectrometer.

5. Data Analysis

The accurate mass data obtained from the mass spectra can be analyzed using any technique known in the art. In certain embodiments, the accurate mass data obtained can be compared to one or more mass or formula databases of known or predicted compounds. For example, and not by way of limitation, the accurate mass of known or predicted compounds can be present within a database, as discussed above. In certain embodiments, the database can contain the accurate masses and/or chemical formulas of compounds that are present in food products or generated during the processing of the food product, e.g., during sterilization. By way of example, and not limitation, such databases include the Human Metabolome Database (HMDB) and the Kyoto Encyclopedia of Genes and Genome (KEGG). In certain embodiments, the database can include the accurate masses and/or chemical formulas of flavor compounds, taste active compounds, amino acids, peptides, saccharides, sugars, flavor precursor compounds, Maillard precursor compounds, Maillard reaction intermediates (known or theoretical), Maillard reaction products, fatty acids, phenolic compounds and the like. By comparing the accurate mass data obtained from the one or more analyzed samples to the accurate mass or chemical formula of known or predicted compounds, the identity of the compounds present within the samples (and, therefore, the complex mixture) can be determined and further analyzed to determine whether such compounds change in levels and/or are consumed or generated by chemical reactions that occur during the production of the complex mixture. In certain embodiments, the accurate mass data obtained from the one or more analyzed samples can be used to determine the way in which the complex mixture was generated. For example, the accurate mass data can be used to identify raw materials used in the process of generating the complex mixture. By way of non-limiting example, the complex mixture can be a food product, and the accurate mass data can be used to determine the raw materials used to generate the food product, e.g., compounds used in a Maillard reaction and emulsifiers.

Figure 8:
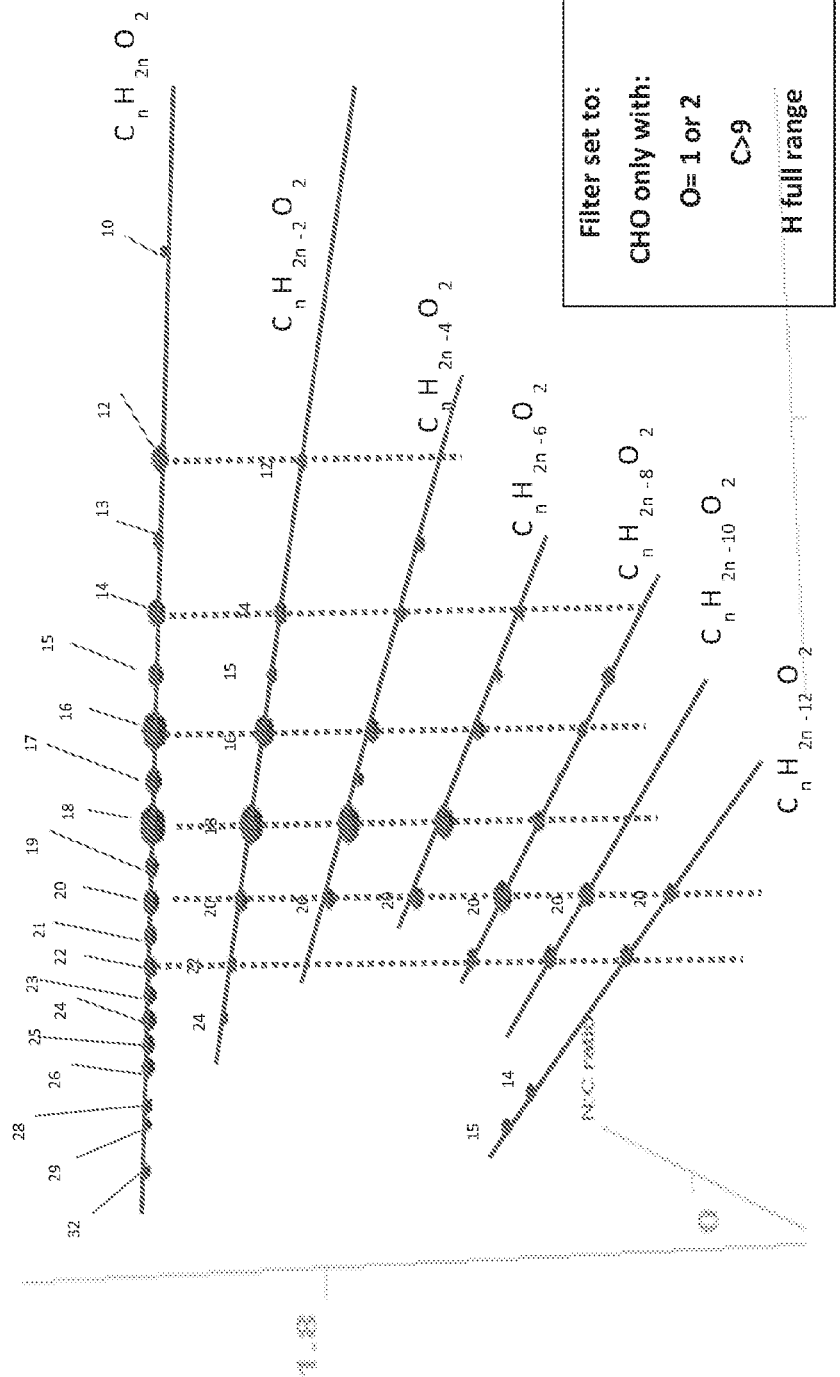
FIG. 8. Van Krevelen representations of fatty acids in a sample of commercially available wet pet food produced in the lab scale reactor. Data obtained from ultra high resolution mass spectrometry using a FT-ICR-MS. The size of the "bubbles" indicates the ion intensity (related to the amount in the sample).
Figure 9:
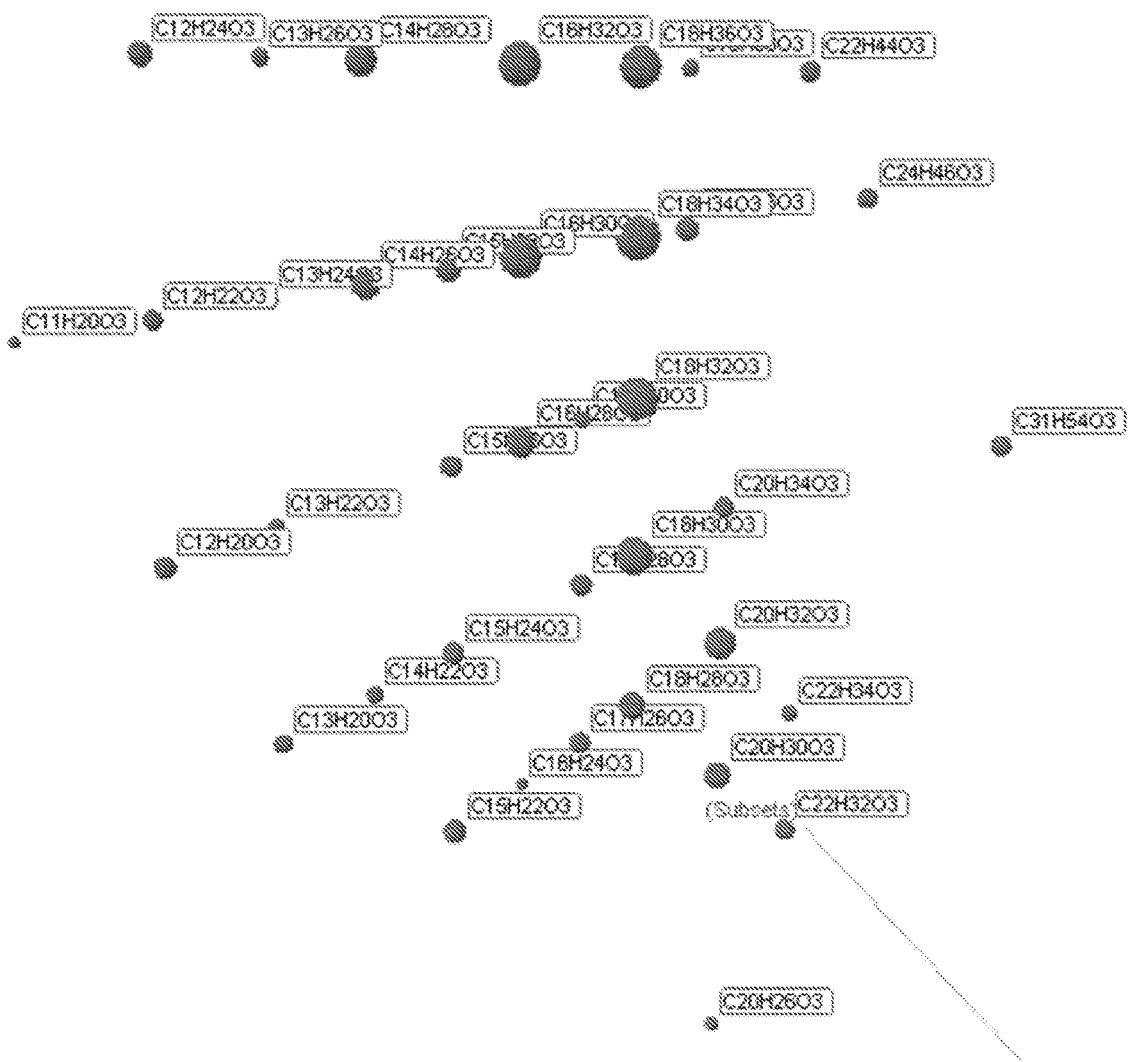
FIG. 9. Van Krevelen diagram showing compounds that contain C>12, H (not limited) and O=3. The compounds visualized include hydroxyl analogs of some fatty acids.
Figure 10:
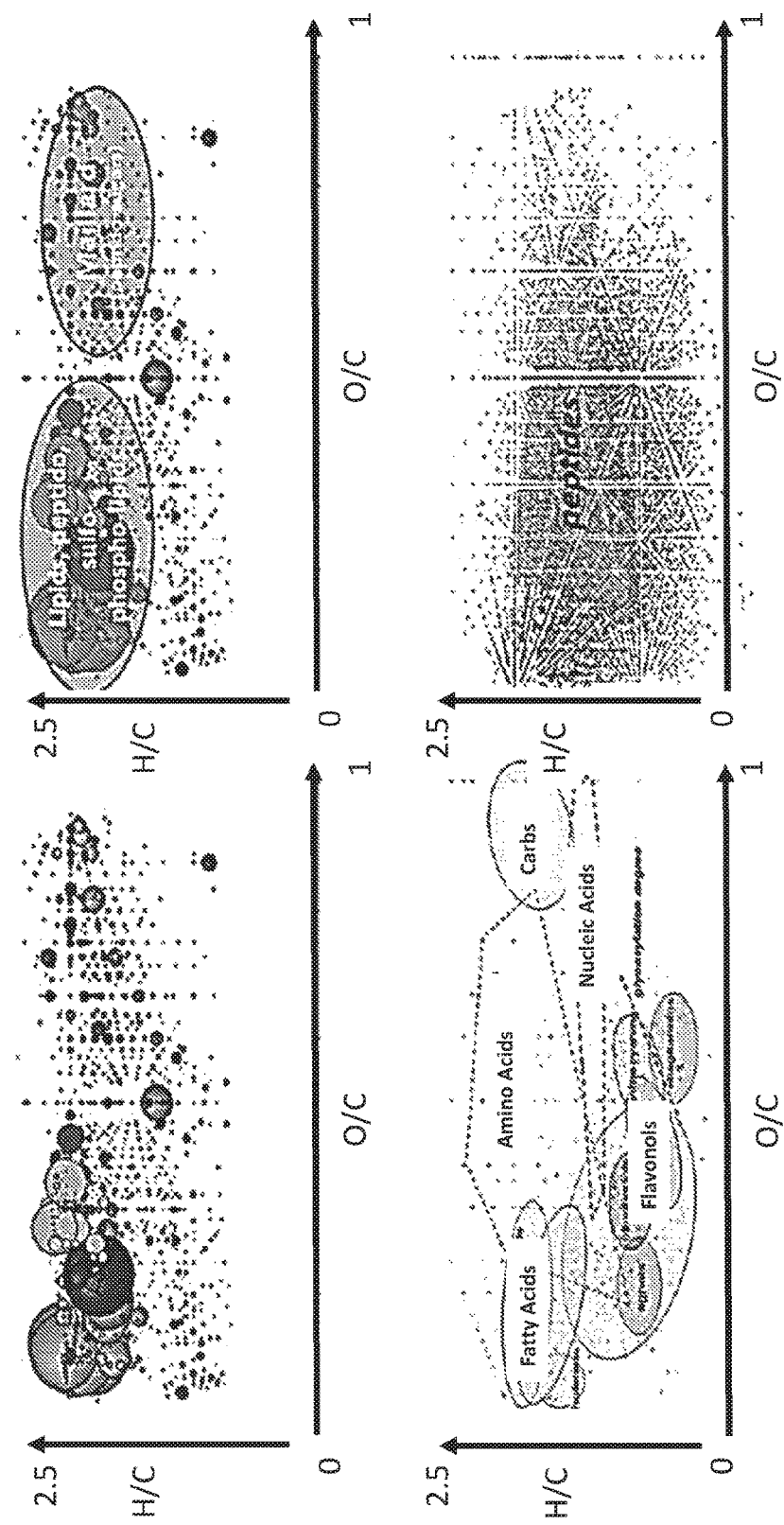
FIG. 10. Van Krevelen diagrams which visualize the chemical fingerprint of commercially available pet food extracts determined using FT-ICR-MS. The top van Krevelen diagrams are visualizations of the FT-ICR-MS spectra of wet cat food (average of all samples). The bottom 2 van Krevelen diagrams show where chemicals of different classes fall within the same van Krevelen space (based on theory). In van Krevelen diagrams, the size of the "bubbles" generally relates to relative ion intensity. Position in the plot is dictated by hydrogen:carbon (H:C) and oxygen:carbon (O:C) ratios. Other elemental ratios of interest can also be plotted (calculated from the elemental composition). The color of the bubble is dictated by elemental composition (which elements other than C, H and O are present in the compound).
Figure 11:
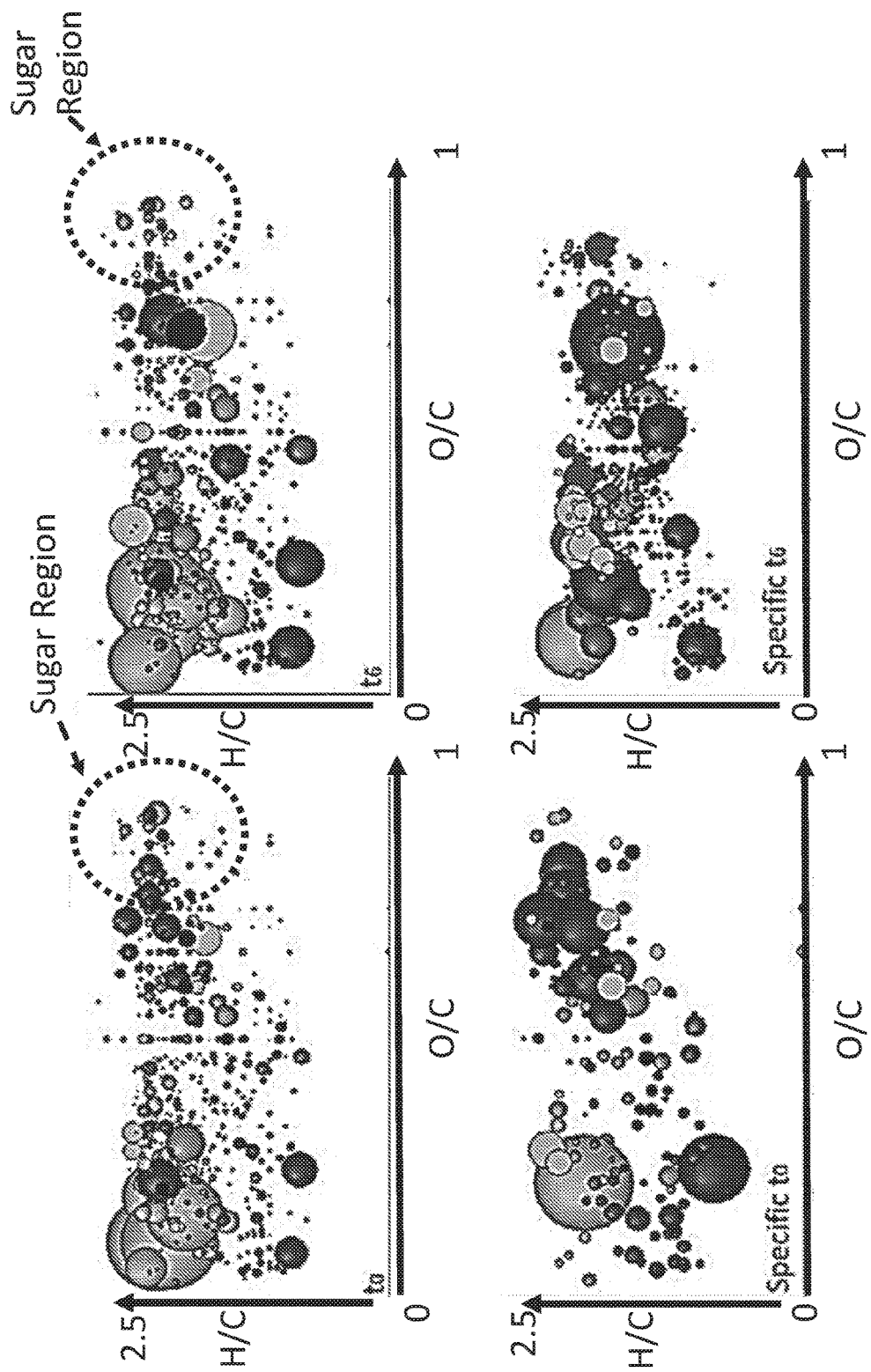
FIG. 11. Van Krevelen diagrams showing the changes to the chemical profile of a wet pet food product due to the cooking process. The diagram labeled "$t_0$" presents a chemical profile of homogenized raw materials before sterilization. The diagram labeled "$t_6$" presents a chemical profile after sterilization. The diagram labeled "Specific $t_0$" presents components which are destroyed by chemical reaction during early phases of heating. The diagram labeled "Specific $t_6$" presents components produced late in the cooking thermal process by reaction of components of the pet food matrix.

In certain embodiments, the accurate mass data and/or the chemical formulas (i.e., predicted compounds) obtained from such mass spectra can be visualized using van Krevelen two-dimensional (2D) and three-dimensional (3D) diagrams. For example, and not by way of limitation, visualization of mass spectra data by van Krevelen diagrams can be used to identify compounds that change in levels and/or for identifying chemical reactions that occur during production of a complex mixture. In certain embodiments, the van Krevelen diagrams can plot the hydrogen:carbon (H:C;

hydrogen index), the oxygen:carbon (O:C; oxygen index) and/or nitrogen:carbon (N:C; nitrogen index) atomic ratios of the compounds identified within the complex mixture (see, for example, FIGS. 8 and 9, which present 2D van Krevelen diagrams of data filtered to show specific chemical classes, and FIGS. 10 and 11, which present 2D van Krevelen diagrams indicating the elemental composition of the compounds). In certain embodiments, the van Krevelen diagrams can plot the molecular formula, ion intensity value, sample ID (e.g., when comparing multiple samples), carbon number, oxygen number, the number of any other element including, but not limited to, oxygen, sulfur, nitrogen and phosphorous and/or mass to charge ratio (m/z). In certain embodiments, the accurate mass data can be visualized using van Krevelen diagrams that only include compounds having a particular elemental composition and/or a particular carbon:oxygen, nitrogen:carbon, carbon:hydrogen and/or oxygen:hydrogen ratio. Such manipulation of the accurate mass data allows the analysis of a particular subset of compounds and/or a particular class of compounds (see FIGS. 8 and 9). For example, and not by way of limitation, compounds that have at least one sulfur can be removed from the diagram. In certain embodiments, the use of such diagrams allows the visualization of potential chemical relationships between the identified compounds. For example, and not by way of limitation, series of homologous compounds (e.g., the fatty acid families; see FIG. 8) can also be identified using van Krevelen diagrams.

In certain embodiments, the data obtained from the ultra high resolution mass spectrometry can be evaluated using multivariate analysis techniques. Non-limiting examples of such techniques include principal component analysis (PCA), partial least squares analysis (PLS), or analysis of variance (ANOVA) with a multiple correlation correction (for example, but not limited to, Bonferroni's or Tukey's honestly significant difference (HSD)). In certain embodiments, the use of multivariate analysis techniques allows the identification of compounds that statistically differ in levels between samples of the complex mixture. For example, and not by way of limitation, compounds that change significantly in amount during a thermal process (i.e., those involved in during thermally catalyzed chemical reactions, e.g., as reactants, or those that are formed during the chemical reaction) can be identified and further analyzed and/or monitored. Alternatively or additionally, compounds which are present at different levels in different samples (e.g., from products from different regions, factories, recipes, manufacturers and/or produced with different raw materials, etc.) can be identified.

In certain embodiments, the presence of reaction intermediates and/or products can be determined by identifying compounds that differ by a specific mass. For example, and not by way of limitation, the type of reaction(s) taking place can be assessed by identifying all the compounds that differ by a specific mass difference. For example, such mass differences can include, but are not limited to, the addition of a water molecule ($H_2O$, which has a mass of about 18 Daltons (Da) and, in its most abundant isotopomer, a characteristic exact mass of 18.010565) for a hydration reaction, the phosphorylation of a compound, e.g., a sugar, by the addition of $HPO_3$ (which has a mass of about 80 Da and, in its most abundant isotopomer, a characteristic exact mass of 79.966333), the loss of $CO_2$ (which has a mass of about 44 Da and, in its most abundant isotopomer, a characteristic exact mass of 43.989830) for a decarboxylation reaction, and the addition of an oxygen atom (which has a mass of about 16 Da and, in its most abundant isotope, a characteristic exact mass of 15.994915), the loss of a sugar and/or an amino acid for a Maillard reaction or loss of two hydrogens ($H_2$; which has a mass of about 2 Da and, in its most abundant isotopomer, a characteristic exact mass of 2.015650) for oxidation. In certain embodiments, an oxidation reaction can be identified by the addition of one or more oxygens to a compound. In certain embodiments, an elimination reaction can be identified by the loss of a eliminable compound, moiety and/or a chemical group from a compound. For example, and not by way of limitation, the loss of an amino acid from a compound, can be indicative of an elimination reaction, e.g., such as an elimination reaction that occurs during a Maillard reaction. In certain embodiments, an addition reaction can include the addition of a compound, moiety and/or a chemical group to a compound. For example, and not by way of limitation, the addition of an amino acid to a compound, e.g., a sugar, can be indicative of an addition reaction, e.g., such as an addition reaction that occurs during a Maillard reaction.

Alternatively or additionally, the presence of reactants, reaction intermediates and/or products can be identified based on predicted chemical formulas and searching the mass spectrum data set for the calculated exact mass value(s) of the reactant(s), reaction intermediate(s) and/or product(s). In certain embodiments, specific chemical reactions that result in target key compounds can be monitored using the mass spectrum data. Non-limiting examples of key compounds include methyl furanthiol, Amadori compounds, Maillard reaction intermediates, pyrazines, and furanones. In certain embodiments, the presence of flavor precursors including sugars and amino acids, e.g., reactants of Maillard reactions, can be determined by searching for the accurate or exact masses of those precursors in the mass spectrum of the sample.

In certain embodiments, the identification of such chemical reactions can be performed by using an algorithm. In certain embodiments, for compounds that may be produced by a condensation reaction, the algorithm can identify any compound (e.g., Z) in the mass spectrum data sets which is equal to the mass of two different compounds (e.g., X and Y) minus water using, for example, the following formula: ($Z=X+Y-H_2O$). In certain embodiments, for compounds that are produced by a hydrolysis reaction, e.g., peptides, the algorithm can identify any compound (e.g., X) which could be added to the mass of a second compound (e.g., Y) minus water to equal the mass of a third larger compound (e.g., Z) using, for example, the following formula: $X+Y-H_2O=Z$. In certain embodiments, for elimination reactions, the algorithm can identify compounds that have a mass that is equal to the mass of a compound minus an eliminable compound such as, but not limited to an amino acid, water or $CO_2$. In certain embodiments, for addition reactions, the algorithm can identify compounds that have a mass that is equal to the mass of two different compounds. In certain embodiments, for phosphorylation reactions, the algorithm can identify compounds that have a mass that is equal to the mass of a compound plus a phosphate group. In certain embodiments, by combining the above data analysis and processing steps, it is possible to deduce which chemical reactions are occurring in a thermal process. For example, if a compound is involved in a chemical reaction the intensity of the ion corresponding to that compound would change significantly (up and/or down and/or fluctuate) over time as it is formed from the reaction of precursor compounds and/or react with one or more other reactive compounds to form one or more products.

6. Non-limiting Embodiments

The present disclosure provides methods for analyzing the chemical composition of a complex mixture during a production process, e.g., a thermal process, using ultra high resolution mass spectrometry. In certain embodiments, the method can comprise preparing a complex mixture, e.g., in a lab-scale reactor, by a production process, e.g., a sterilization process. In certain embodiments, the method can include obtaining two or more samples of the complex mixture during the production process and/or after completion of the production process, e.g., about 7 or more samples. In certain embodiments, the method can further comprise preparing the two or more samples for ultra high resolution mass spectrometry, e.g., by an extraction technique, and performing ultra high resolution mass spectrometry on the two or more samples to obtain a mass spectrum for each of the samples. Non-limiting examples of preparation techniques are described above. In certain embodiments, the samples are ionized, e.g., by electrospray ionization, prior to performing ultra high resolution mass spectrometry on the samples.

In certain embodiments, the method further includes identifying one or more compounds from the mass spectra of the two or more samples. In certain embodiments, the compounds can be identified by the comparison of the mass spectra of the samples to the mass spectra of known or predicted compounds, e.g., through the use of a spectral database. In certain embodiments, the spectral database comprises mass spectra information for compounds found in food products and/or compounds that are reactants, reaction intermediates or products of Maillard reactions. In certain embodiments, the method can further include comparing the levels of each identified compound between the two or more samples to identify compounds that decrease and/or increase in level between the samples.

In certain embodiments, compounds that significantly increase and/or decrease in levels, e.g., exhibit greater than about a 2-fold, greater than about a 3-fold, greater than about a 4-fold or greater than about a 5-fold change in intensity between the samples, can be further analyzed. In certain embodiments, the compounds that significantly change in intensity can be further analyzed to identify compounds that differ by a specific mass difference (as discussed above) to determine if a chemical reaction occurs during the production process. Alternatively or additionally, the method can include predicting a chemical formula and mass for a reactant, intermediate and/or product of a chemical reaction and identifying such compounds within the mass spectra data sets from the two or more samples to determine whether the chemical reaction occurs during the production process.

In certain embodiments, the levels of the compounds that correspond to reactants, intermediates and/or products of a chemical reaction can be monitored during a production process, e.g., by multiple in-process sampling, to monitor the efficiency and/or prevalence of the chemical reaction. In certain embodiments, such information can be used to change the production process, as described above, to result in a reduction and/or increase in one or more of the identified compounds. In certain embodiments, the production process is modified by altering the raw materials used to produce the complex mixture. In certain embodiments, the occurrence of Maillard reactions during the production of a complex mixture, e.g., pet food product, can be monitored using the disclosed methods.

EXAMPLES

The presently disclosed subject matter will be better understood by reference to the following Examples, which are provided as exemplary of the invention and should not be construed as limiting the scope of the invention in any way.

Example 1: Use of a Lab Scale Manufacturing Process to Analyze Pet Food Compositions During Production To determine whether a lab-scale process can mimic a factory-scale process for use in the disclosed methods, the composition of pet food products produced in a lab-scale process was compared to the composition of pet food products produced in a factory-scale process. Wet pet food products used in this Example were produced in a 600 gram lab-scale reactor. The wet pet food products produced within the lab-scale reactor were made from the same raw materials on the same day as the wet pet food products produced in the factory-scaled processes. The time and temperature profiles for the lab-scale reactor and the factory-scale process during the sterilization of the wet pet food products were analyzed (FIG. 1). As shown in FIG. 1, the time and temperature of profiles for the factory-scale and the lab-scale sterilization processes were similar. In addition, the $f_0$ values, which are used as a measure to ensure microbiological safety is achieved by sterilization, for the lab-scale and factory-scale processes were very similar and were within the normal variation allowed in the factory-scale process. Therefore, the lab-scale reactor was able to be operated at the same sterilization conditions as the factory-scale process.

Figure 2:
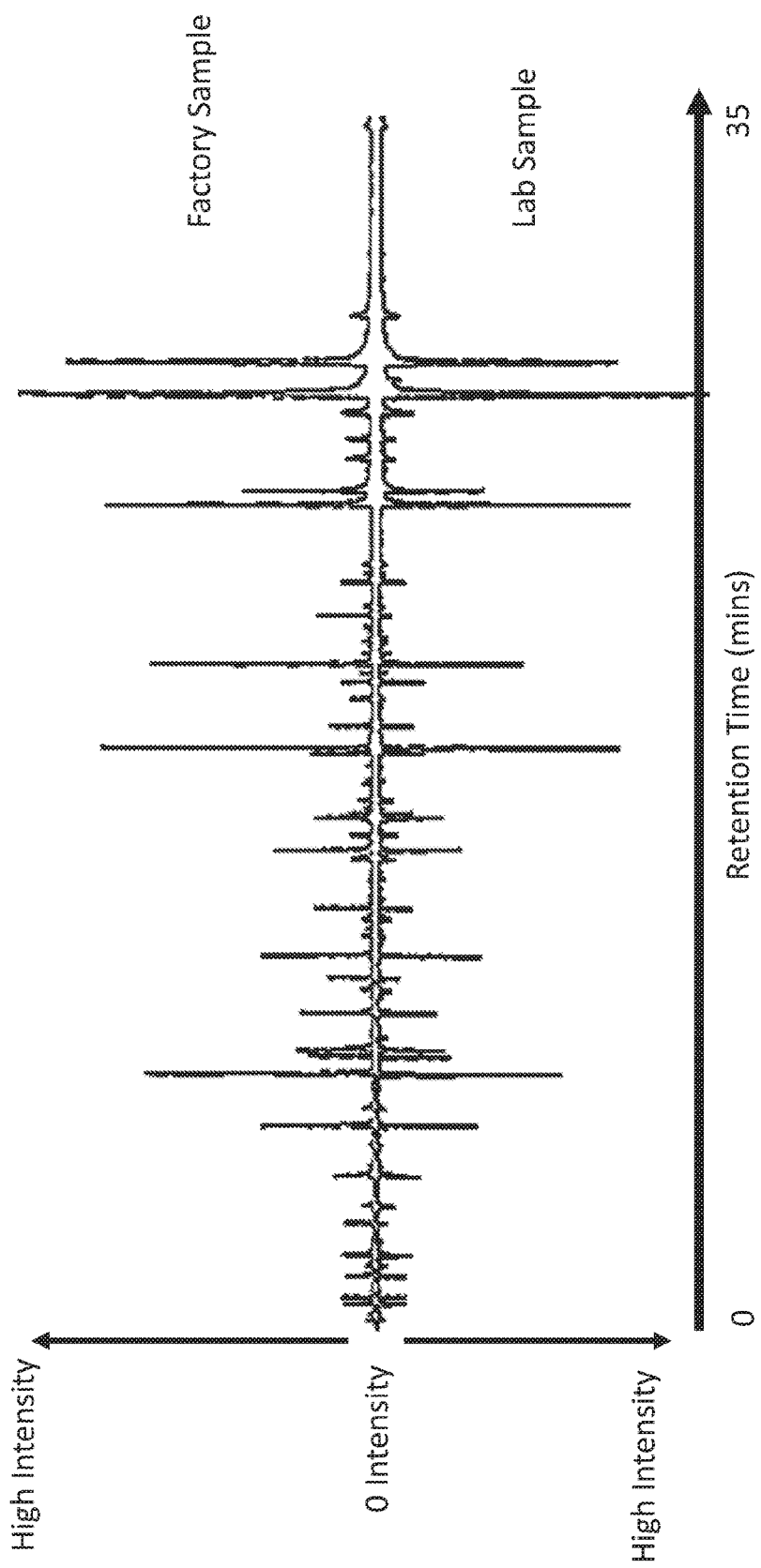
FIG. 2. Comparison of a lab-scale produced wet pet food product and a factory-scale produced wet pet food product. Chromatogram obtained from GC-MS analysis of a sample of the wet pet food produced in the factory is depicted in the top panel and a chromatogram obtained from GC-MS analysis of a sample of the wet pet food produced in the lab-scale reactor is depicted in the bottom panel.

The wet pet food products produced in the lab-scale reactor and the factory-scale process were analyzed by headspace solid phase microextraction gas chromatography-mass spectrometry (HS-SPME-GC-MS) to determine the similarity in their volatile aroma chemical compositions. Volatile aroma compounds were analyzed because they are produced in low amounts during pet food production (in nanograms or micrograms/gram) and are considered to be a sensitive measurement of similarity. As shown in FIG. 2, the wet pet food product produced by the lab-scale process (bottom panel) exhibited the same aroma profile as the wet food produced within the factory (top panel). This analysis shows that at the end of the thermal process, the flavor profile of the product from the lab scale reactor is the same as the flavor profile of the factory produced product.

Figure 3:
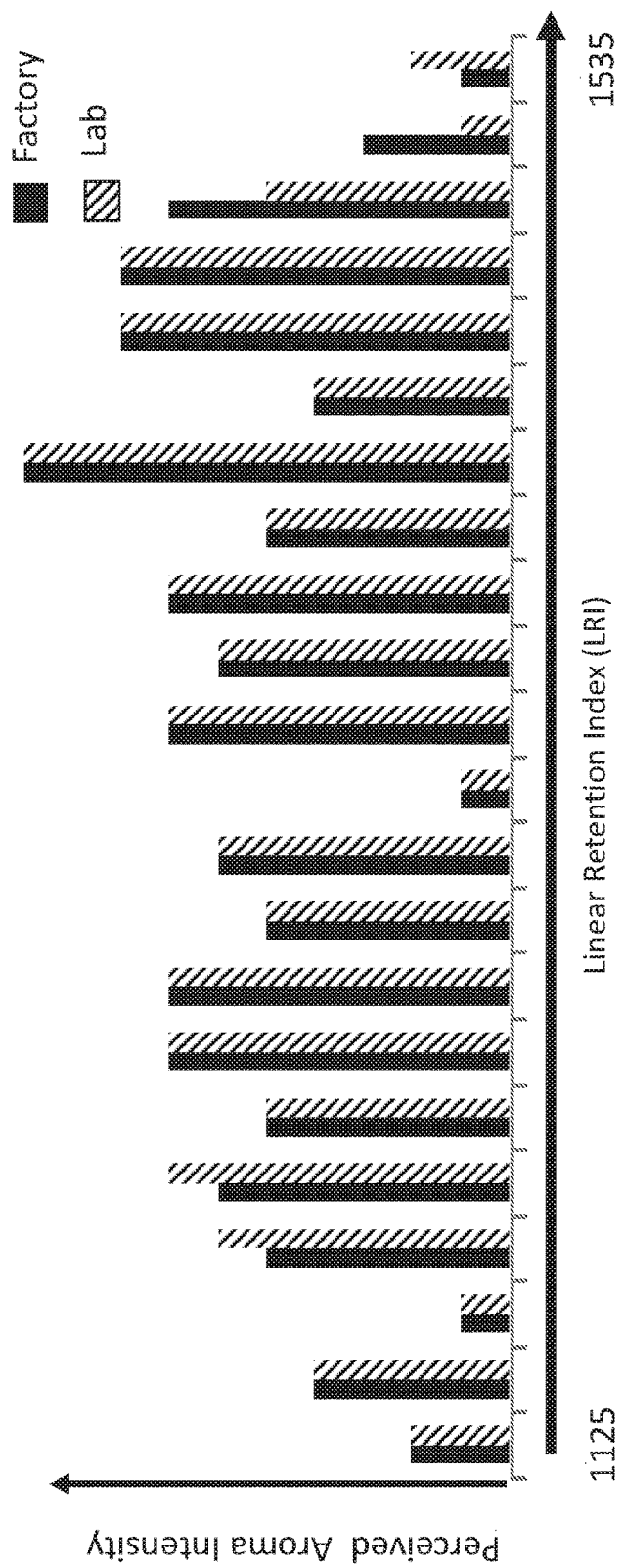
FIG. 3. Comparison of a lab-scale produced wet pet food product and a factory-scale produced wet pet food product by Gas Chromatography-Olfactometry.

The pet food samples of the lab-scale and the factory-scale processes were also analyzed by Gas Chromatography-Olfactometry (GC-O). Peaks from the gas chromatograph were sniffed by human assessors and aroma extract dilution analysis (AEDA) was performed to quantify the odor strength of each peak in each sample. As shown in FIG. 3, the histogram shows a comparison of the factory-scale (first bar) and lab-scale (2nd bar) chromatograms. Most peaks have similar values (FIG. 3). Statistical analysis showed that only 7 out of 42 peaks were statistically different. However, small changes in odor do not always translate into sensory differences; therefore, the two pet food products were further analyzed using a sensory-based analysis.

For evaluation by a human sensory panel, the homogenized samples of the sterilization lab-scale runs Lab1 and Lab2 were combined. 15 g of homogenized sample (combined lab or factory (MEL)) was placed in taped and individual coded closed containers. The samples were evaluated using a triangle test, where 26 validated panelists were presented with one set of three coded samples, two of which were the same. The set of samples were presented in each of the six possible orders (ABB, BAB, BBA, AAB, ABA or BAA) across the assessment panel. FIZZ software was used for the design of each test, allocating each panelist randomly to a presentation order. The test was carried out in the sensory panel room in individual booths using red light to eliminate visual sample differences. Each panelist was asked to sniff the samples and select the one which was different. Panelists were allowed to retry the three samples following the same presentation order. Results were analyzed with the FIZZ software using a probability test (p=1/3) for a binomial distribution with a α-risk of 5%. As shown in Table 1, panelists were unable to differentiate the two samples on the basis of smell.

TABLE 1

Results of the smell triangle test from the lab-scale and the factory-scale sterilized pet food products

| Test | Products | Answers Taken | Answers Right | p-value* |
|---|---|---|---|---|
| Triangle test (smell) | CIJ from Lab and Factory | 26 | 9 | 0.518 |

*α = 0.05

Figure 4A:
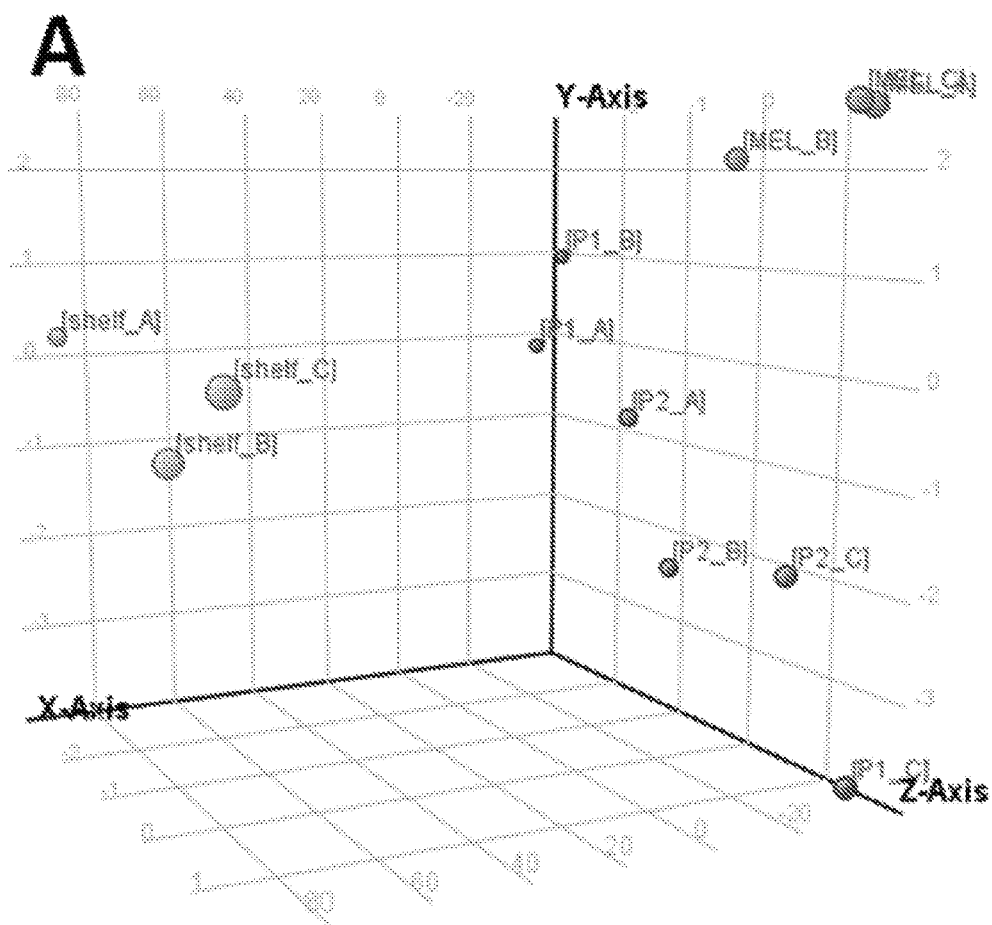
FIG. 4A. The 3D principal component analysis (PCA) plot of Quadrupole Time of flight-mass (Q-ToF)-spectrometry negative ion scan data collected on the different samples ([MEL]; [P1] and [P2]—Lab1 and Lab2; [Shelf]—ST).
Figure 4B:
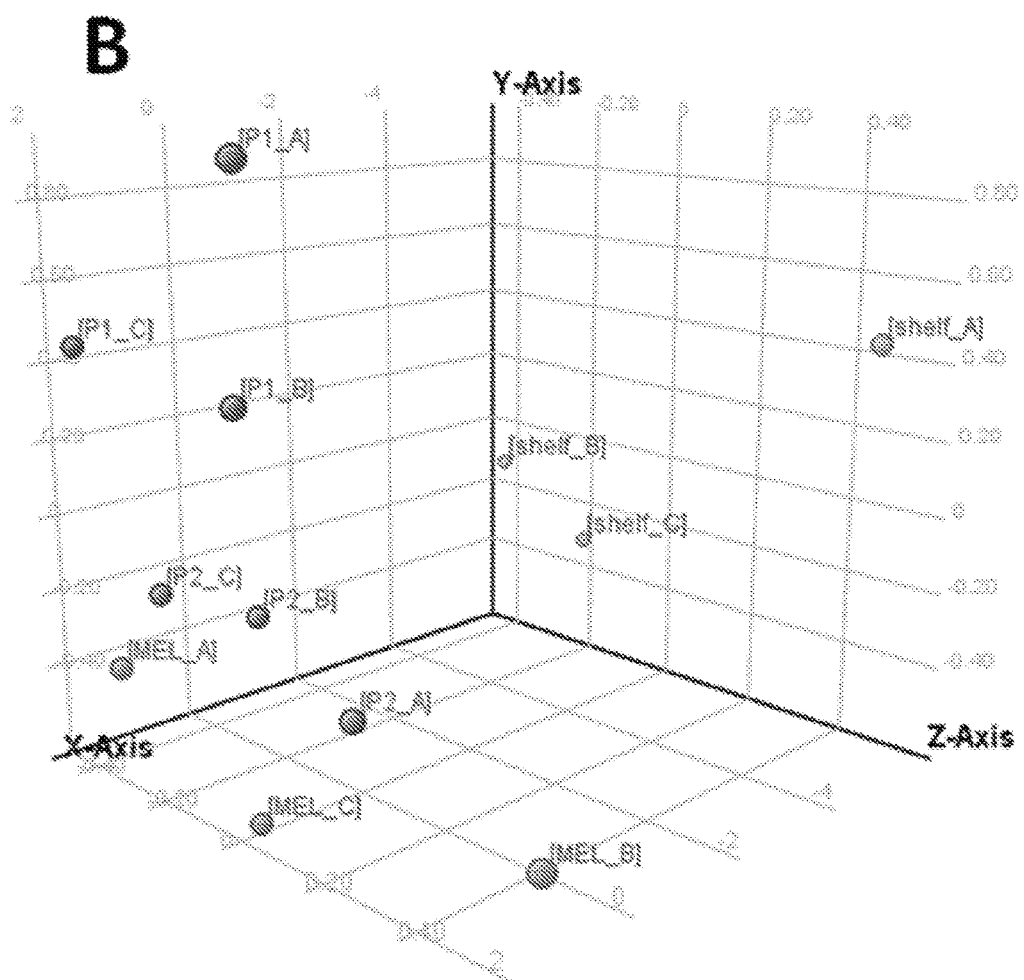
FIG. 4B. The 3D PCA plot of positive ion scan data of the Q-ToF spectrometry.

To compare the lab-scale and the factory-scale products regarding their non-volatile profiles, untargeted analysis using Liquid Chromatography Quadrupole Time-of-flight Mass spectrometry (LC-QToF-MS) was performed. To extract a broad range of compounds, a methanol/water (50/50, v/v) extraction step was performed to prepare the sample. The extracts were then analyzed on a RP-18 column in positive and negative ionization and the obtained data was processed to identify statistical differences between the samples. To understand the occurring batch-to-batch variability within the factory process and to determine the similarities between the lab-scale and the factory-scale products, an additional equivalent sample produced on a different production date in the factory was analyzed. FIG. 4 displays the 3D principal component analysis (PCA) plot of the negative (A) and positive (B) data set after statistical interrogation. In both the positive and negative ionization data, little to no variation between Lab 1, Lab2 and the corresponding sample from the factory (MEL) were observed. Within each sample group, the samples were spread out on the Y- and Z-axis, but there is a clear separation on the X-axis of the stored samples. As shown in FIG. 4, more than 90% of the variability in the data set was explained by the discrimination of the stored samples from all other samples (NEG: 92.3% PC1, 3.2% PC2, 3.0% PC3; POS: 96.4% PC1, 1.8% PC2, 0.9% PC3). Furthermore, the discrimination of the shelf (ST; i.e., stored) sample was driven by only a few variables (17 in the positive data and 11 in the negative data). Without being bound to a particular theory, these data suggest that either the batch to batch variation or the age of the product has a greater effect on the chemical profile of the samples than the difference between processing in the lab-scale system versus the factory-scale sterilization processes.

Figure 5:
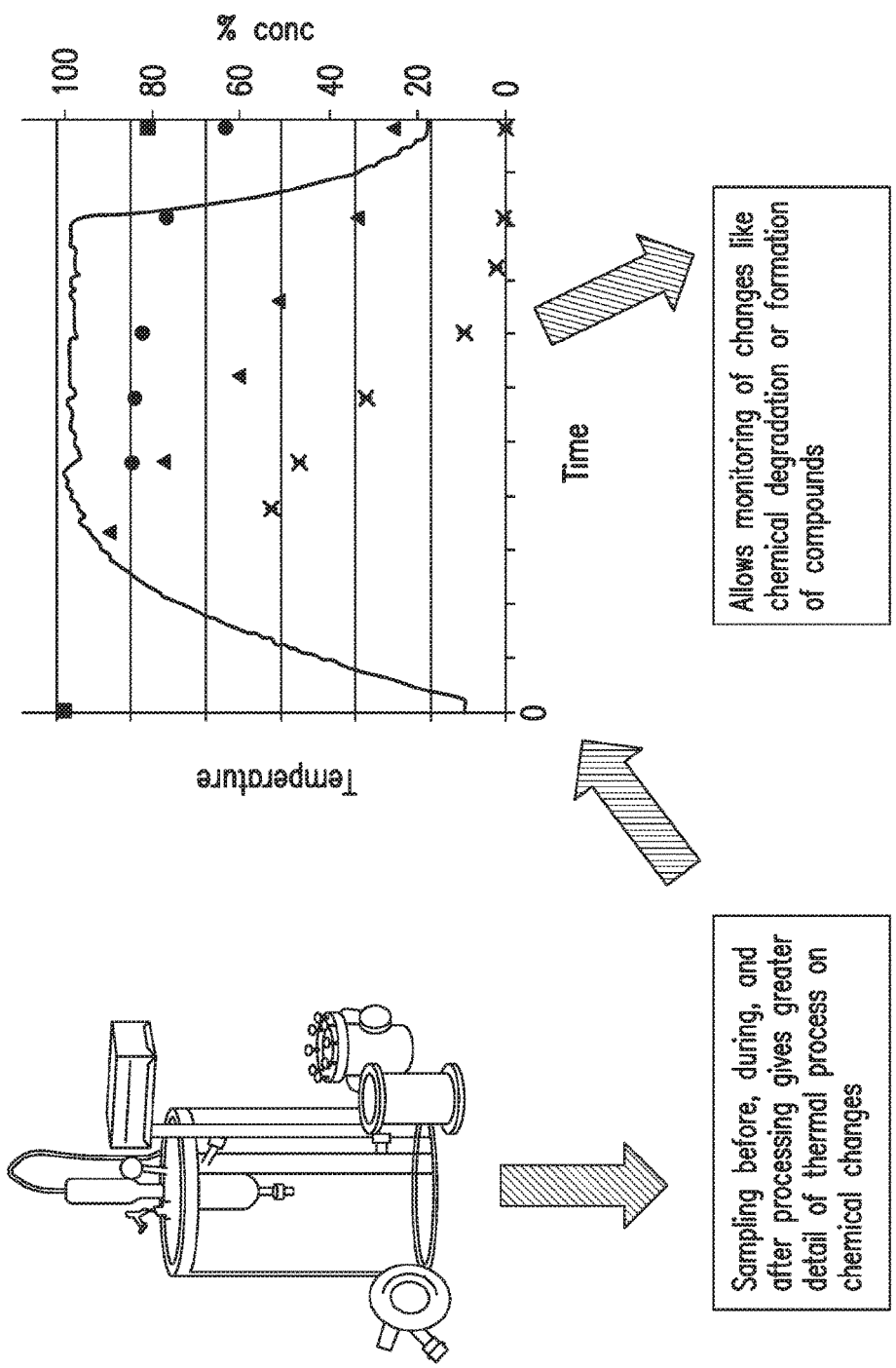
FIG. 5. The internal temperature of a lab scale sterilizer and the change in level of nutrients and vitamins (symbols) added to a pet food product produced during sterilization.

To further determine whether lab-scale manufacturing of pet food products can be used to analyze the chemical reactions that occur during pet food production, pet food chunks were processed in different matrices, and the degradation of a well-known odor compound was analyzed during sterilization of the pet food product. Samples of the pet food product during lab-scale production were obtained before, during and after sterilization to understand the effect thermal processing has on the stability of the odorant in the pet food product. As shown in FIG. 5, the amount of odorant in the pet food was measured over time and temperature. As shown in FIG. 5, some matrices (circles, i.e., gravy) showed limited degradation, while others (stars, i.e., different buffers) were completely degraded at the end of sterilization.

These results provide support that the lab-scale and factory-scale processes both result in wet pet food products having similar compositions and that any differences were minimal, and that lab-scale production of pet food can be used to analyze the composition and monitor the chemical reactions that occur during pet food production.

Example 2: Ultra High Resolution Mass Spectrometry of Pet Food Products

The resolution of Fourier transform ion cyclotron resonance mass spectrometer (FT-ICR-MS) measurements is such that even a complex sample such as a pet food extract can be directly analyzed and chemically fingerprinted. Food products are extremely complex, and as with other types of untargeted analysis, ultra high resolution mass spectrometry is able to consider a far greater proportion of the chemical in a sample than conventional targeted analysis (which may only look at 10% or less of the chemical species present). Because each measured mass has an associated intensity, the chemical fingerprint of samples can be evaluated statistically, revealing information about the inter-sample relationships.

To determine whether ultra high resolution mass spectrometry (uHRMS) can be used to analyze the chemical composition of pet food products, samples of the wet pet food product produced within the lab-scale reactor were analyzed using FT-ICR-MS using a methanol/water (50/50, v/v) extraction technique. uHRMS spectra were acquired in negative ion mode on samples infused directly into the mass spectrometer using nanoESI. 500 scans were accumulated in the m/z 90-1000 range. Once acquired, the spectra were calibrated (to ensure the accuracy of the mass measurement), filtered to remove signals with a signal to noise ratio (S/N)<6 to remove noise and the spectrum of each sample was aligned to within a 1.0 ppm mass error to ensure that the same compounds are treated as the same in every sample in which they are present across the sample set. For example, in a recent experiment 6692 unique mass signals were detected. After application of a signal to noise filter (S/N≥6), 2659 mass signals were retained. After formula prediction, 1687 of the remaining mass signals were assigned to CHONSP elemental composition. Molecular formulas for the measured masses were predicted using an algorithm. Once the formulas were predicted, further annotation (if required or desired) was possible using either a molecular formula or accurate mass database.

Figure 6:
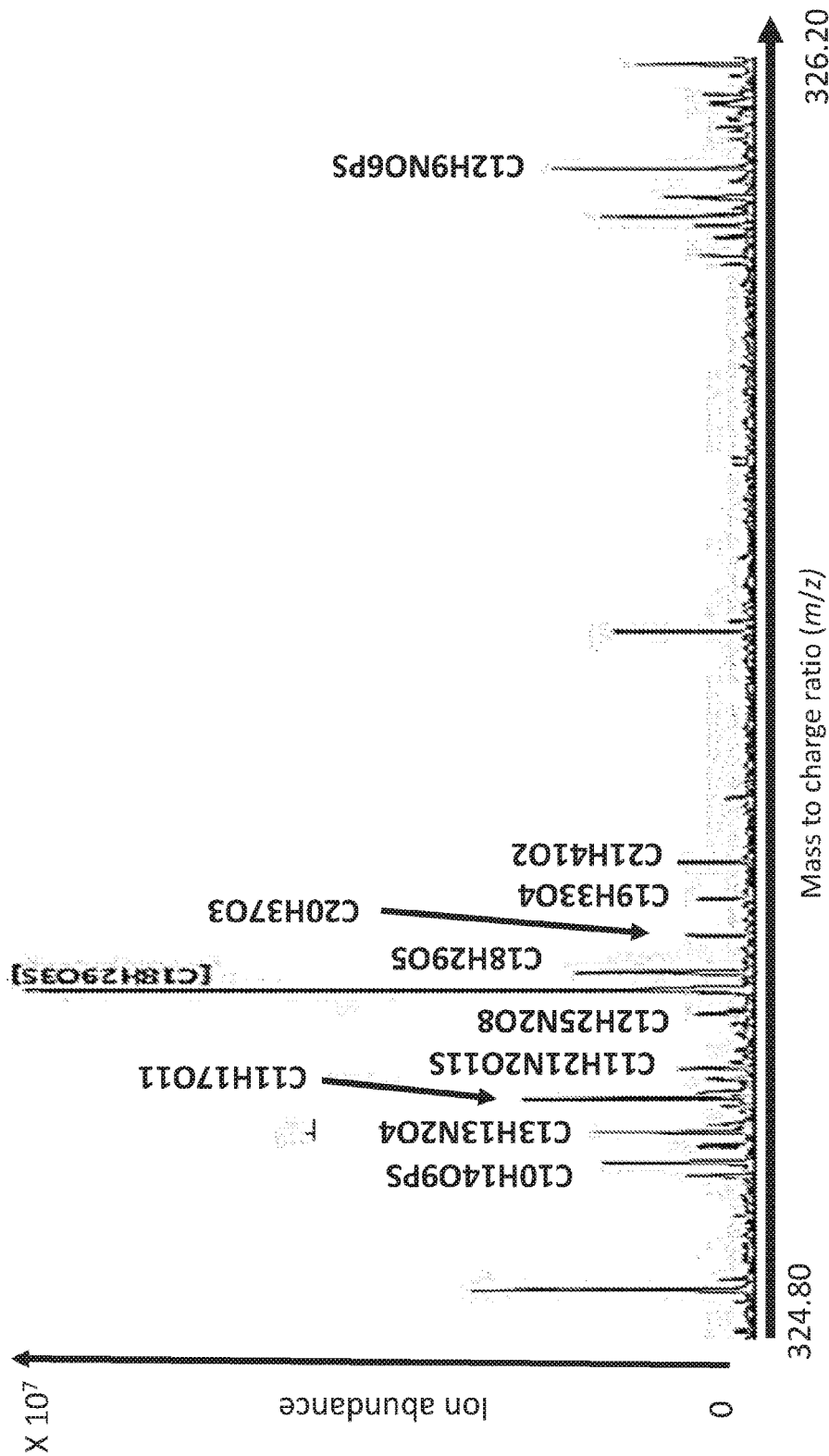
FIG. 6. Expansion (m/z 325-326) of the Fourier transform ion cyclotron resonance (FT-ICR) mass spectrum acquired during analysis of a methanolic aqueous extract of a commercially available wet cat food diet. Approximately 20 ions are resolved in the displayed region of the spectrum which spans approximately one atomic mass unit. Calculated molecular formulas are shown for some of the more abundant ions. Even on a high resolution Time of flight-mass spectrometry (ToF-MS) system, many of the ions that were detected in the FT-ICR mass spectrum would not be resolved and may be measured as the average of a distribution of a mass ions (isobaric), rather than as a collection of different species (each having slightly different m/z values, e.g., molecular masses).

As shown in FIG. 6, expansion of the m/z 325-326 range of the FT-ICR mass spectrum (lower panel) was acquired during analysis of a methanolic/aqueous extracted sample of a commercially available wet cat food product. Approximately 20 ions were resolved in the displayed region of the spectrum, which spans approximately one atomic mass unit. Calculated molecular formulas are shown for some of the more abundant ions (FIG. 6). Even on a high resolution Time-of-flight mass spectrometry (ToF-MS) system, many of the ions detected in the displayed FT-ICR-MS mass spectrum would not be resolved and would have appeared as a distribution of a single mass ion, rather than as a collection of different species. Therefore, these data show that uHRMS can be used to analyze a complex mixture such as a pet food product with sufficient resolution to allow the identification of compounds that are isobaric.

As noted above, van Krevelen diagrams are one way of visualizing the FT-ICR-MS data of complex samples and comparing visually the chemical fingerprints of different samples or the differences between samples. Using van Krevelen diagrams (plots of the H:C, O:C and N:C ratios) the compounds can be visualized in a different way compared to conventional chromatographic data. In addition, filter settings allow the removal of chemical species from the van Krevelen diagrams that are not of interest to simplify analysis. For example, the filter settings allow the identification of classes of compounds of interest such as saturated fatty acids (e.g., $C_nH_{2n}O_2$), monounsaturated fatty acids (e.g., $C_nH_{2n-2}O_2$; see FIG. 8), nucleotides (e.g., $N_4O_8P$), simple sugars (e.g., $C_nH_{2n}O_n$), Maillard intermediates, neutral peptides (e.g., $N_nO_{n+1}$; see FIG. 16), nutrients, and undesirable compounds. In van Krevelen diagrams, the size of the "bubbles" generally relates to relative ion intensity, and the color of the bubble can be dictated by elemental composition (which elements other than C, H and O are present in the compound).

Figure 7:
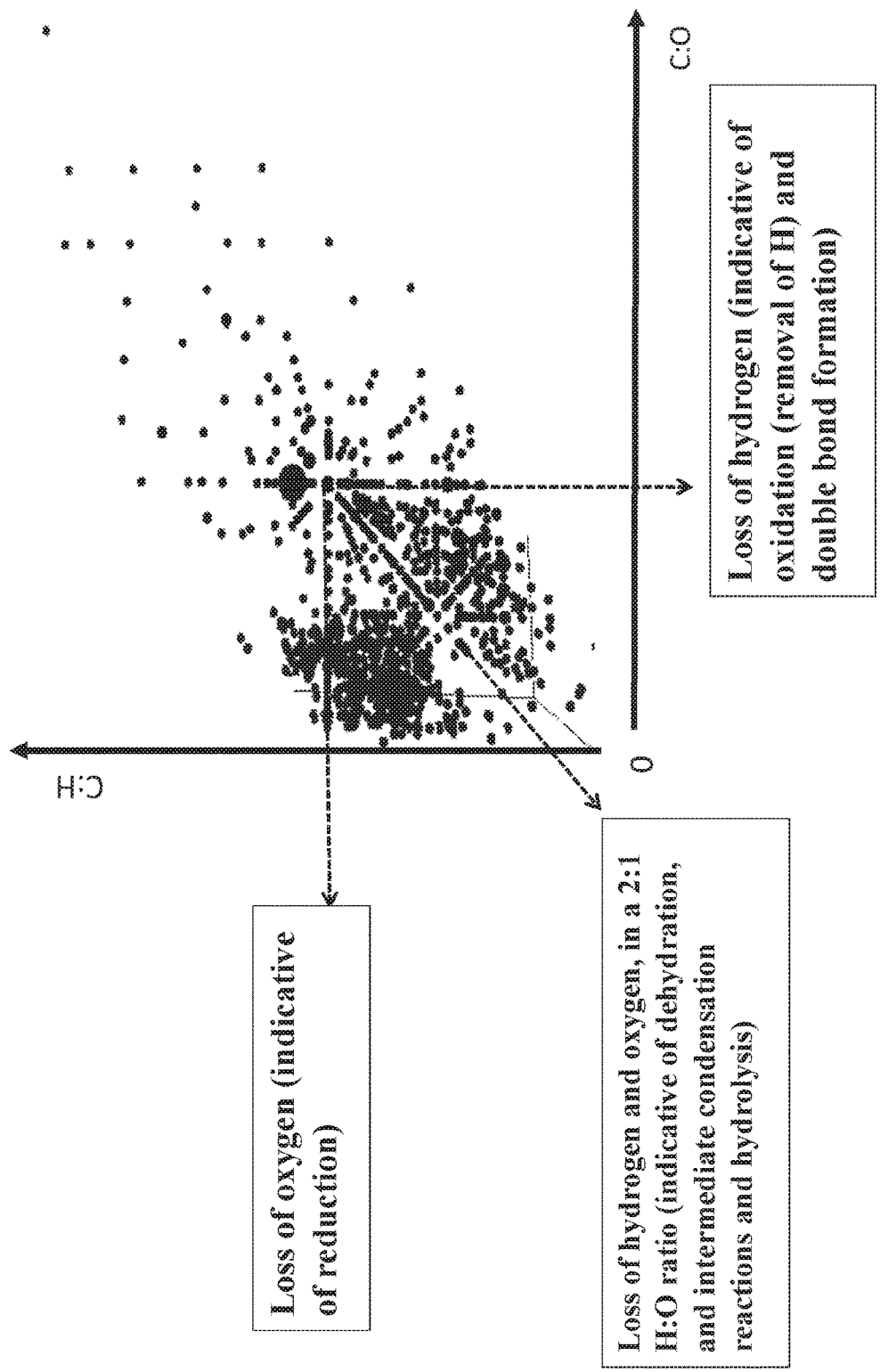
FIG. 7. Van Krevelen diagram showing compounds present within a sample of a wet pet food product produced in the lab scale reactor. Each "bubble" represents a compound visualized on the O:C and H:C axes based on the elemental composition of the compound. Size of each "bubble" is proportional to ion intensity.

FIG. 7 shows van Krevelen diagrams of mass spectra data obtained using FT-ICR-MS of an extract of a wet pet food. Each "bubble" (or spot) represents a compound visualized on the O:C and H:C axes, and the size of each "bubble" is proportional to ion intensity. As depicted in FIG. 7, the horizontal line shows compounds that have the same H:C ratio but differ in their O:C ratio. For example, moving from right to left of the diagram, the compounds contain less oxygen, which is indicative of a reduction series. The vertical line shows compounds that have the same O:C ratio but differ by their H:C ratio, and moving from top to bottom of the diagram, the compounds contain less hydrogen and, therefore, represent an oxidative series. As shown in FIG. 7, the diagonal line highlights that such a line with a slope that has a hydrogen to oxygen ratio of 2:1 represents the loss of water (dehydration or elimination; when moving towards the origin on the diagram) or gain of water (hydration); when moving away from the origin on the diagram). Other trends can also be visualized by plotting O:C, H:C and N:C ratios or by color coding molecules with specific atomic compositions, e.g., the presence of a sulfur or phosphorus atom.

FIG. 8 shows van Krevelen representations of fatty acid data obtained using FT-ICR-MS of a wet pet food sample. To generate the van Krevelen diagram shown in FIG. 8, compounds which contain chemical elements other than C, H, O have been filtered out and compounds with O≠2 have also been filtered out to reveal the free fatty acids detected in the pet food samples. As shown in FIG. 8, the different fatty acid saturation series are labeled, e.g., saturated fatty acids ($C_nP_{2n}O_2$) and fatty acids having one unsaturation ($C_nP_{2n-2}O_2$), two unsaturations ($C_nP_{2n-4}O_2$), three unsaturations ($C_nP_{2n-6}O_2$), four unsaturations ($C_nP_{2n-8}O_2$), five unsaturations ($C_nH_{2n-10}O_2$) and six unsaturations ($C_nH_{2n-12}O_2$). Within each series, different carbon chain lengths are resolved in the van Krevelen diagrams and the carbon numbers are labeled (FIG. 8). The size of the bubble corresponding to each compound is indicative of the relative ion intensity associated with the parent ion of that compound and as such allows inter-sample or cross series comparison of the relative amounts of each compound.

FIG. 9 shows a representation of the fatty acid derivatives present in a wet pet food sample as detected by FT-ICR-MS. To generate the van Krevelen diagram shown in FIG. 9, compounds which contain chemical elements other than C, H, O have been filtered out and compounds with O≠3 have also been filtered out to reveal the oxidized free fatty acid derivatives and furans detected within the samples. As shown in FIG. 9, the different fatty acid unsaturation series were labeled, e.g., saturated fatty acids and mono, double and triple unsaturations. Within each series, different carbon chain lengths were resolved in the van Krevelen diagrams and the carbon numbers were labeled (FIG. 9). The size of the spot corresponding to each compound is indicative of the relative ion intensity associated with the parent ion of that compound and as such allows inter-sample or cross-series comparison of the relative amounts of each compound.

As shown in FIG. 10, van Krevelen diagrams were generated to display the chemical profile of a wet cat food product, e.g., to display the various compounds and classes of compounds detected in a sample of a wet cat food product. The top two van Krevelen diagrams of FIG. 10 are visualizations of the FT-ICR-MS spectra of wet cat food methanolic extracts. The bottom two van Krevelen diagrams show where chemicals of different classes fall within the same van Krevelen space (based on theory). The color of bubble is dictated by the elements (elements other than C, H and O) that are present in the detected compound.

Example 3: Identification and Monitoring of Chemical Reactions Using Ultra High Resolution Mass Spectrometry of Pet Food Products Data interrogation of uHRMS data using chemical signatures can be performed to analyze the changes in concentration of specific types of compounds and the identification of chemical reactions that occur during pet food processing.

Data interrogation requires a suitable software platform to provide visualization, filtering of the chemical data using the mass differences described above and a database containing the molecular formulas, chemical names and accurate masses of the many flavor and precursor compounds already identified. Using an in-house resource, a data interrogation platform was generated that can look at the whole data set and identify chemical features such as homologous series (e.g., the fatty acids in FIG. 8); the phosphorylated versions of some base compounds, e.g., inositol phosphate(s); or the chemical inter-relationships between the compounds in the database. An algorithm was developed to search the FT-ICR-MS data for condensation products, by interrogating each compound and determining if any of the other compounds in the data/sample are related. For example, a condensation reaction involves adding together the two putative compounds and calculating their combined accurate mass value minus the accurate mass of water. When a match to 5 decimal places was found, the compounds were marked as inter-related.

By modifying the condensation algorithm, it was possible to find other products characterized by addition or subtraction of a known mass, e.g., dehydration products. The algorithms can carry out several billion calculations and find all compounds that are inter-related, according to the rules specified. Once several searches were carried out, the inter-related compounds can be visualized on a network diagram and "nodes" (points where pathways intersect) can be identified. For instance, in an early phase Maillard reaction, glycine and glucose can react to form an addition product, then undergo dehydration to form a dehydration product (see FIG. 20A). Therefore in a network diagram, nodes representing glycine and glucose will be connected to the node representing the addition product of glycine and glucose. Further, the nodes will correspond to masses, for example, the node representing the addition product will correspond to the sum of the masses of glycine and glucose. The addition product of glycine and glucose will in turn be connected to a node representing a dehydration product. The node representing the dehydration product will correspond to the sum of the masses of glycine and glucose, minus one water molecule. This provides information on chemical pathways as well as the ways in which pathways interlink during thermal processing of pet food.

Figure 19:
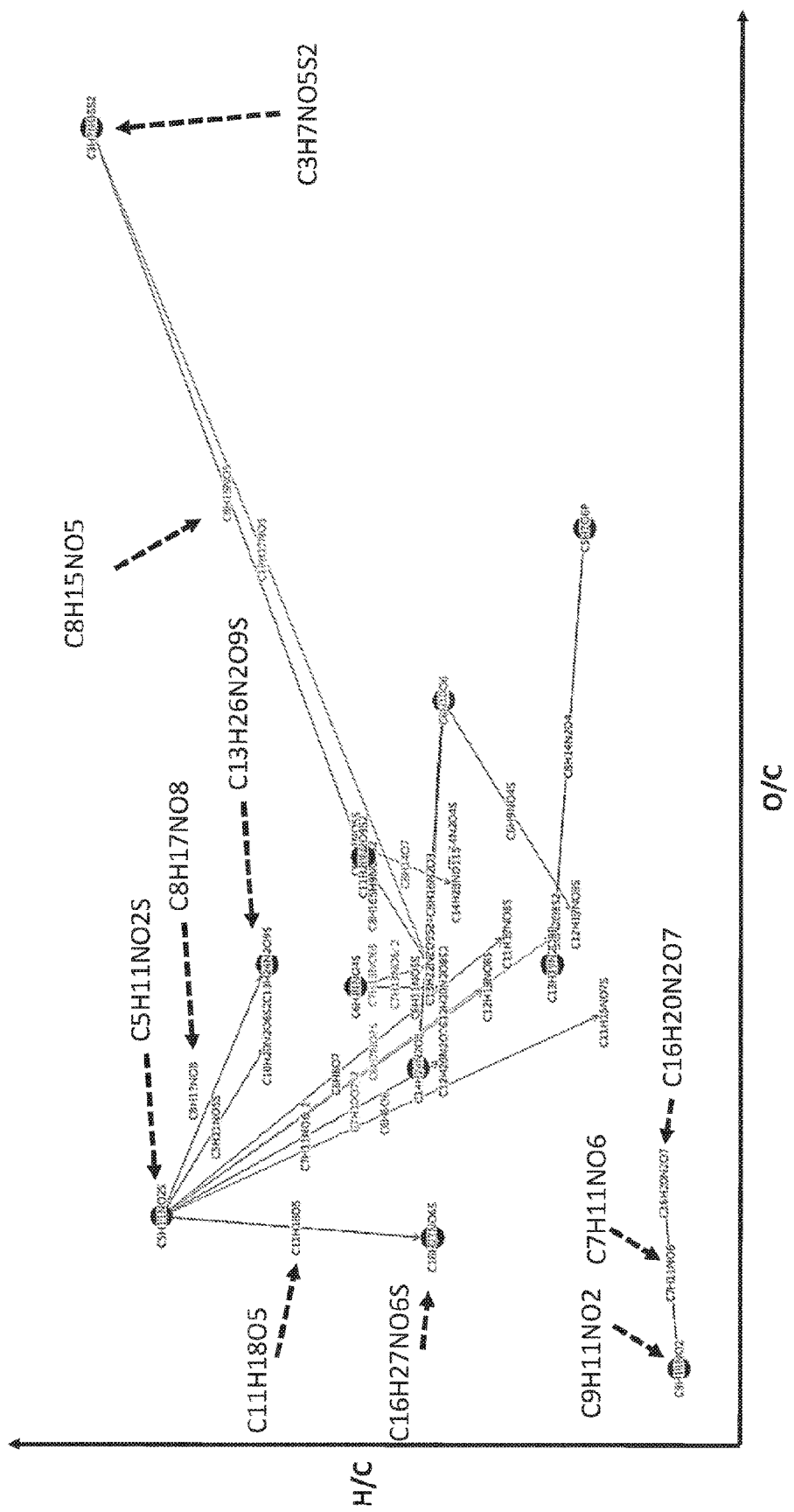
FIG. 19. A network diagram showing inter-compound relationships, where compounds are related by specific mass differences indicative of chemical reactions, e.g., condensation reactions, and directional arrows indicate the reactants and products of the chemical reactions.

FIG. 19 provides an example network diagram. Each node indicates a compound, and the nodes are arranged in space according to the oxygen to carbon (O/C) and hydrogen to carbon (H/C) ratios derived from their molecular formulas. The presence of these compounds was measured at time 0 and time 6 during the thermal processing (heating) of a complex mixture. For purposes of illustration, the data was filtered to show only those nodes that had a significant change in composition at the 95% confidence limit in this time frame. The connections between the nodes are directional, and indicate the chemical reactions that occurred during thermal processing. For example, FIG. 19 depicts only condensation reactions. For each reaction, the compound indicated by the start node reacted with another compound, which is indicated by the label on the connecting arrow. These two compounds released a molecule of water and formed the compound indicated by the end node. For example, $C_9H_{11}NO_2$ (bottom-left corner) reacted with $C_7H_{11}NO_6$ to form $C_{16}H_{20}N_2O_7$ and liberated one molecule of water ($H_2O$). Similarly, $C_5H_{11}NO_2S$ (top-left corner) reacted with $C_{11}H_{18}O_5$ to form $C_{16}H_{27}NO_6S$ and liberated one molecule of water. In this manner, network diagrams can be a useful tool for visualizing compounds that are related by chemical reactions.

From these interrogations, the types of chemistry taking place could be ascertained and the compounds associated with these changes could be identified. In addition, the changes in the level of compounds that were identified to be inter-related can be analyzed for statistical significance. If such compounds were determined to change significantly, e.g., change greater than about 5 fold, over time during the production of the pet food product, such compounds can be further analyzed to identify the particular reactions that they are consumed in or produced by and/or the chemical reactions can be altered to reduce or increase the level of the compound in the pet food product. Limiting the analysis to compounds that increase significantly over time can greatly reduce the amount of data that is to be analyzed. Thus, interpretation of the complex data obtained can be achieved in much more detail and to a deeper level of understanding than with conventional analytical techniques.

To obtain further information, experiments can be re-run with different starting levels of compounds and the effect on the pathways can be ascertained in terms of rate and extent by comparing the ion intensities. To simplify the data processing described in the paragraph above, an alternative was to use well known data analysis techniques like principal component analysis (PCA) or partial least squares analysis (PLS) to scan the whole data set and look for trends in the data, e.g., trends across the time points of an experiment or the key features differentiating different types of samples. PCA and PLS can also indicate which compounds are associated with the trends, thus reducing the number of compounds necessary to subject to data analysis.

For example, in addition to displaying the chemical profile of a complex mixture, two-dimensional and three-dimensional van Krevelen diagrams can be generated to display the changes that occur to the chemical profile of pet food due to cooking. As shown in FIG. 11, the chemical profile of homogenized raw materials before and after sterilization can be analyzed. In FIG. 11, the chemical profile of homogenized raw materials before sterilization is noted as $t_0$ whereas $t_6$ indicates the chemical profile after sterilization. The compounds that were destroyed or altered by chemical reaction during early phases of heating are indicated as "Specific $t_0$." Compounds that were produced later in the cooking thermal process by reactions of components in the pet food are indicated as "Specific $t_6$." Changes in the intensity or presence of particular ions/compounds can be observed between specific samples (FIG. 11). For example, between $t_0$ and specific $t_6$, there are less bubbles corresponding to carbon-hydrogen-oxygen (CHO)-containing compounds in the area that sugars appear in the $t_6$ van Krevelen plot, suggesting sugar is consumed by Maillard (FIG. 11).

Figure 12A:
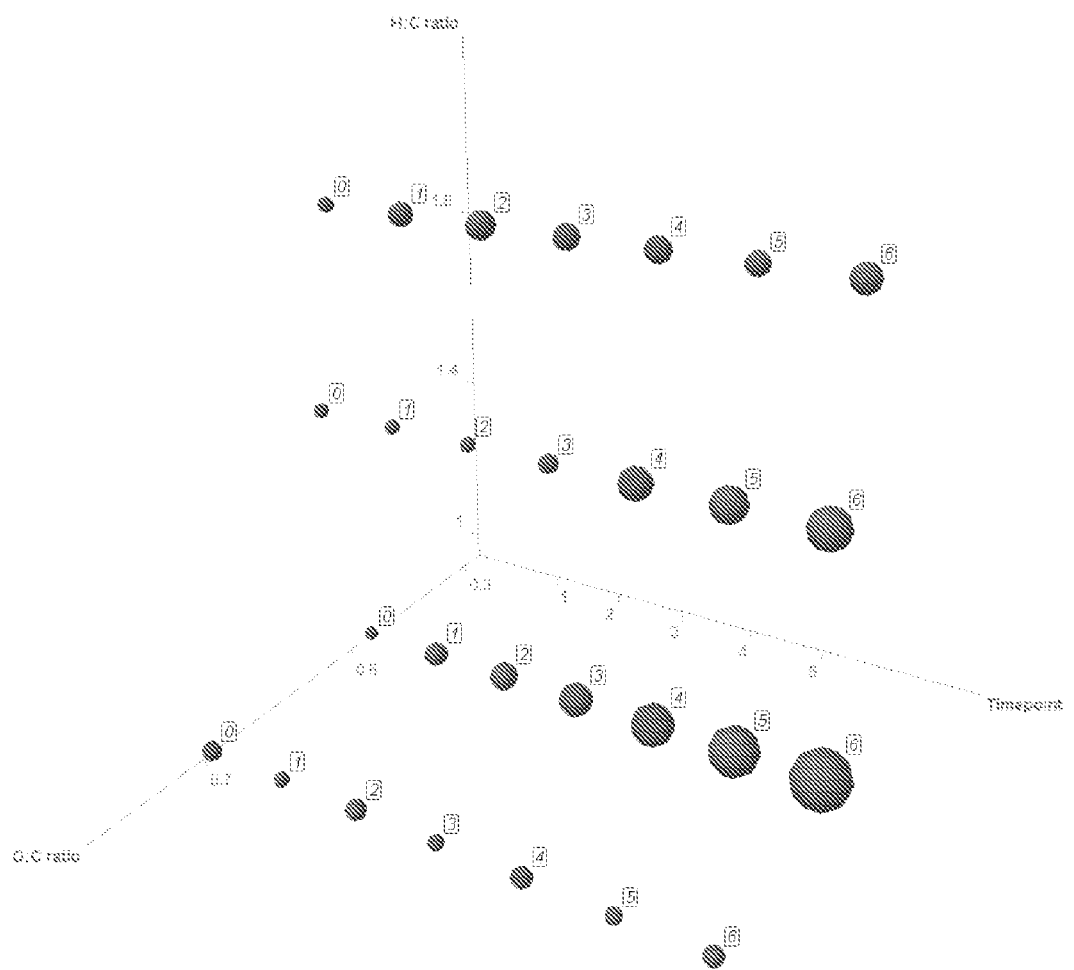
FIG. 12A. Van Krevelen diagram showing compounds that change in concentration during the production process of a pet food. 0 represents raw materials; 1-6 represent sequential stages during the thermal processing step.
Figure 12B:
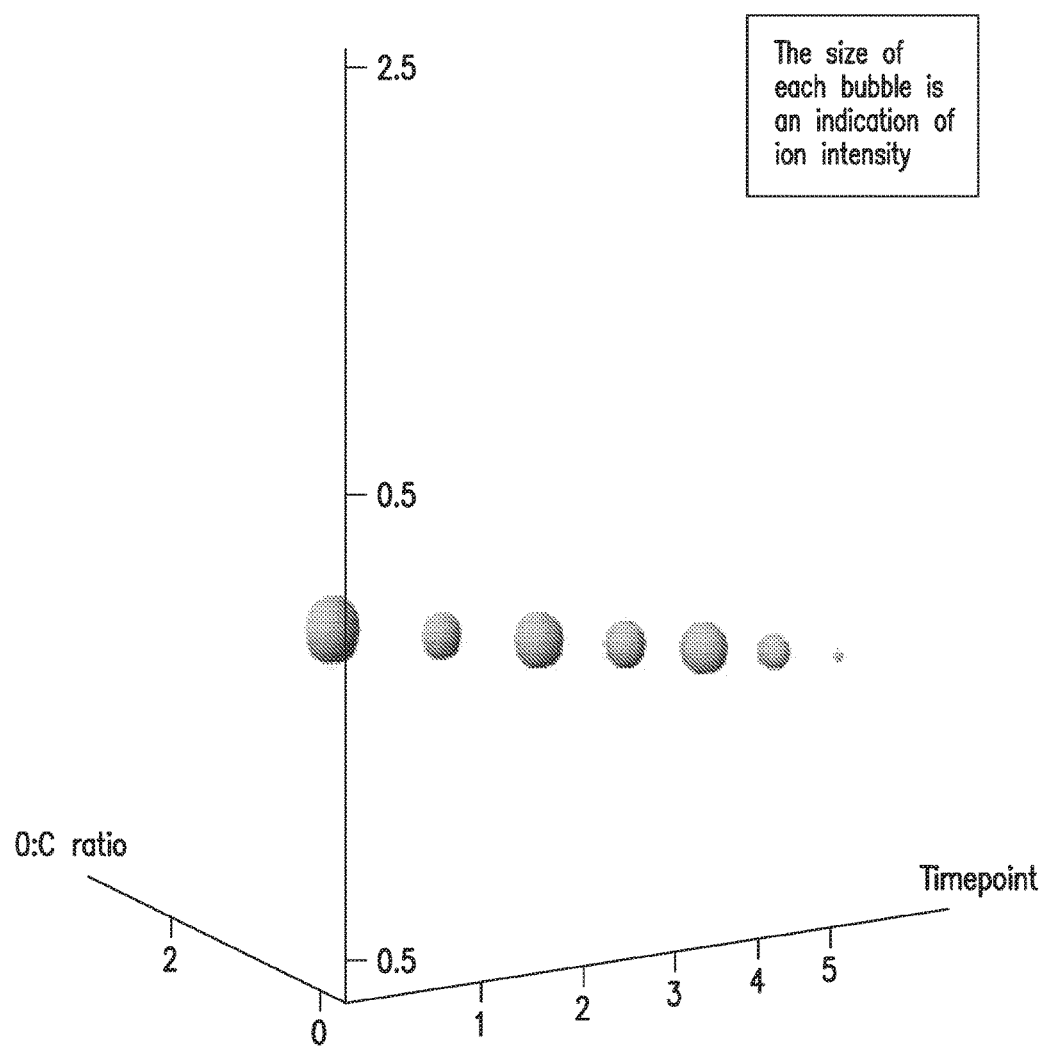
FIG. 12B. Ion intensity plot showing changes in phenylalanine during thermal processing of a pet food.

In addition to the visualization and chemical interpretation of the chemical profile before and after sterilization using van Krevelen diagrams, the flux of some organic matter can be monitored using van Krevelen diagrams to identify the reactions that occur during the cooking thermal process. For example, changes in the composition of the pet food product can be analyzed over time during thermal processing. As shown in FIG. 12A, multiple samples during the production of a pet food product can be obtained, analyzed and visualized using the disclosed methods. The visualization of the mass spectrum data of multiple samples using a van Krevelen diagram (time point 0 ($t_0$) is a sample of the unprocessed pet food and time point 6 ($t_6$) is a sample of the finished pet food product) led to identification of a series of compounds that all showed increased amounts (corresponding to the size of the spheres) at each time point (FIG. 14). Likewise, certain compounds (such as phenylalanine in FIG. 12B) showed decreased amounts after thermal processing. These data show that the disclosed methods can be used to identify the creation and degradation of compounds over time during the sterilization of a pet food.

Figure 13:
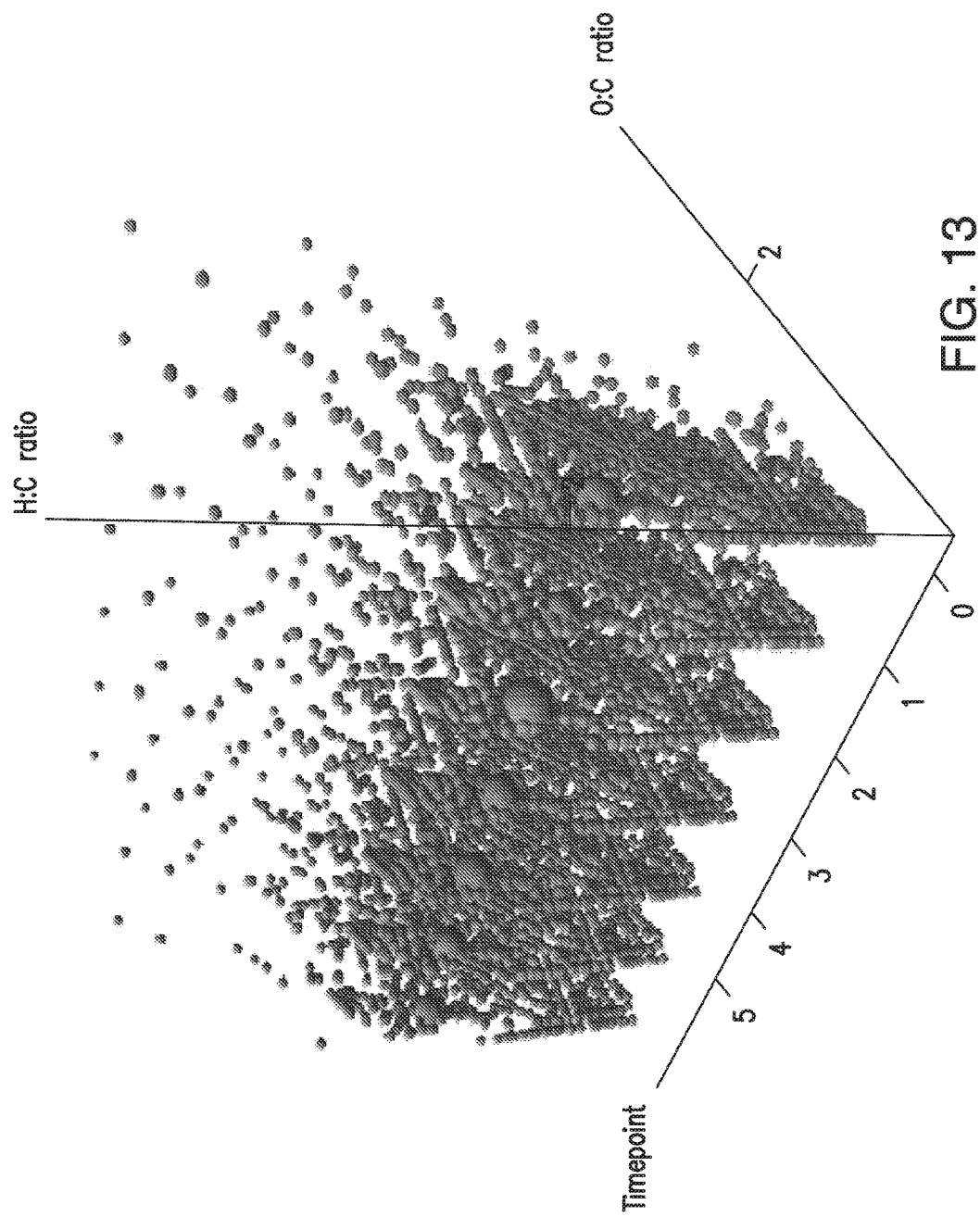
FIG. 13. Van Krevelen diagram showing compounds present within 7 samples of a wet pet food product produced in a lab scale reactor.
Figure 14A:
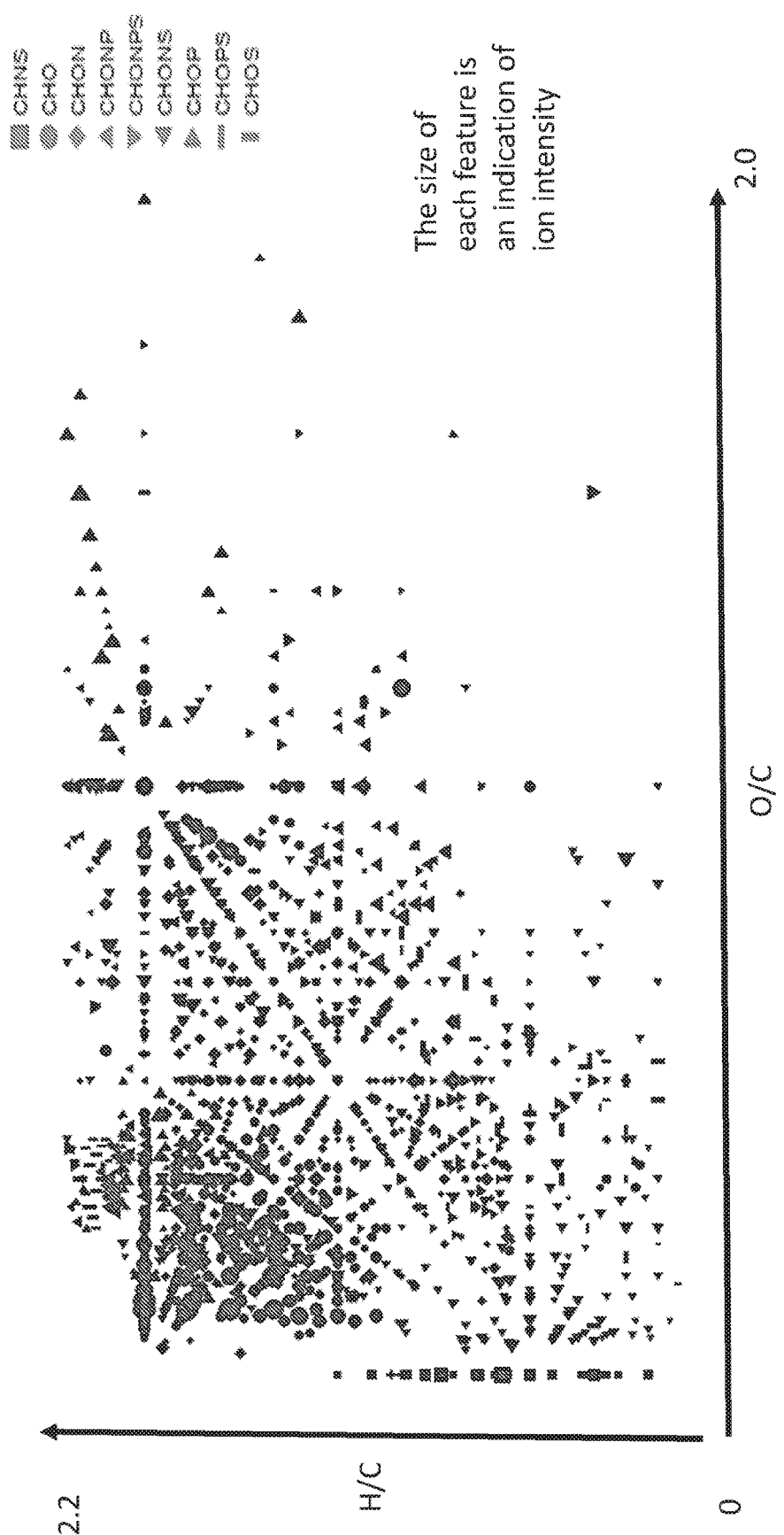
FIG. 14A. Van Krevelen diagram showing the chemical compositions of the pet food product prior to thermal processing ($t_0$).
Figure 14B:
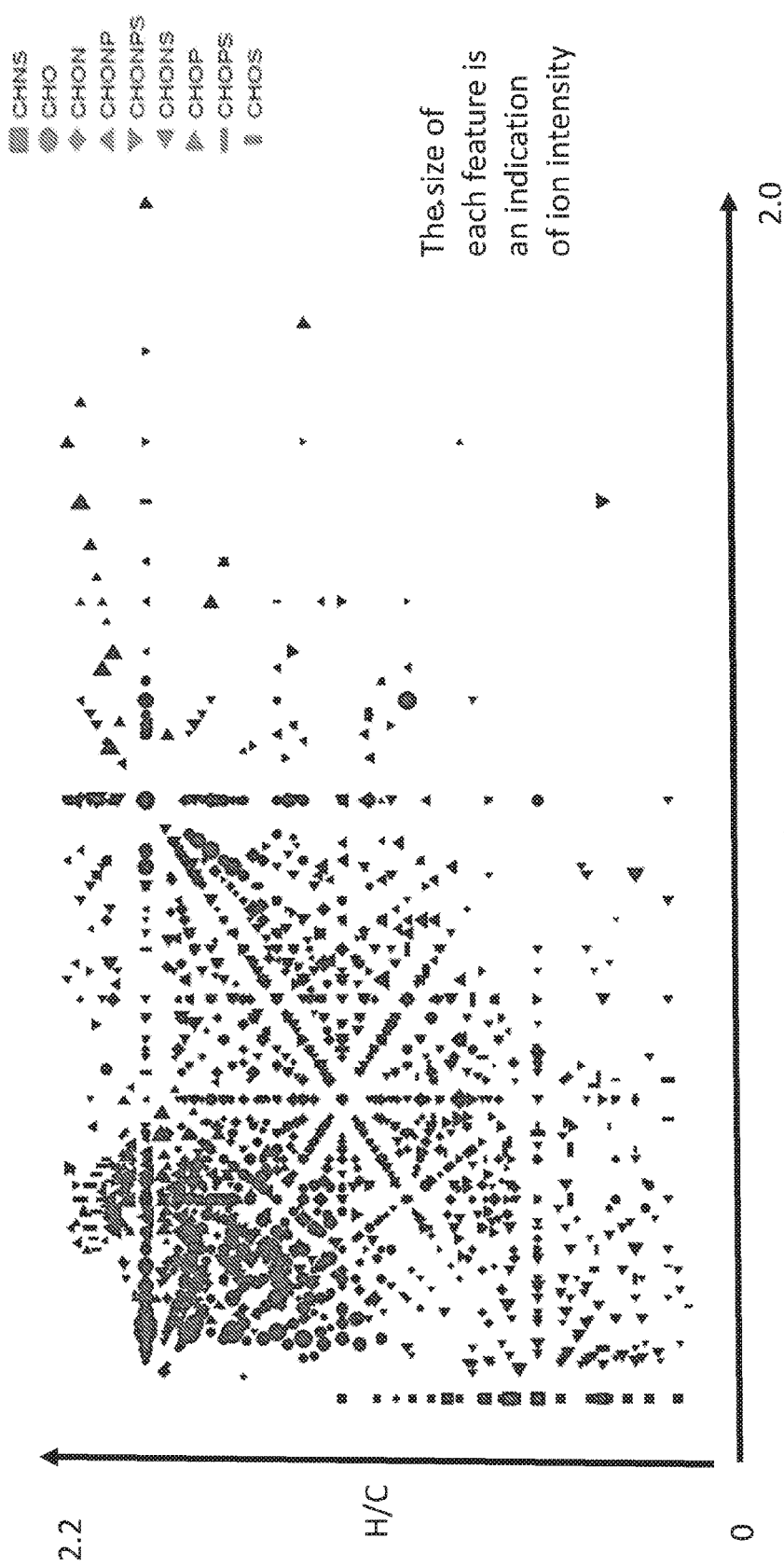
FIG. 14B. Van Krevelen diagram showing the chemical compositions of the pet food product after thermal processing ($t_6$).
Figure 14C:
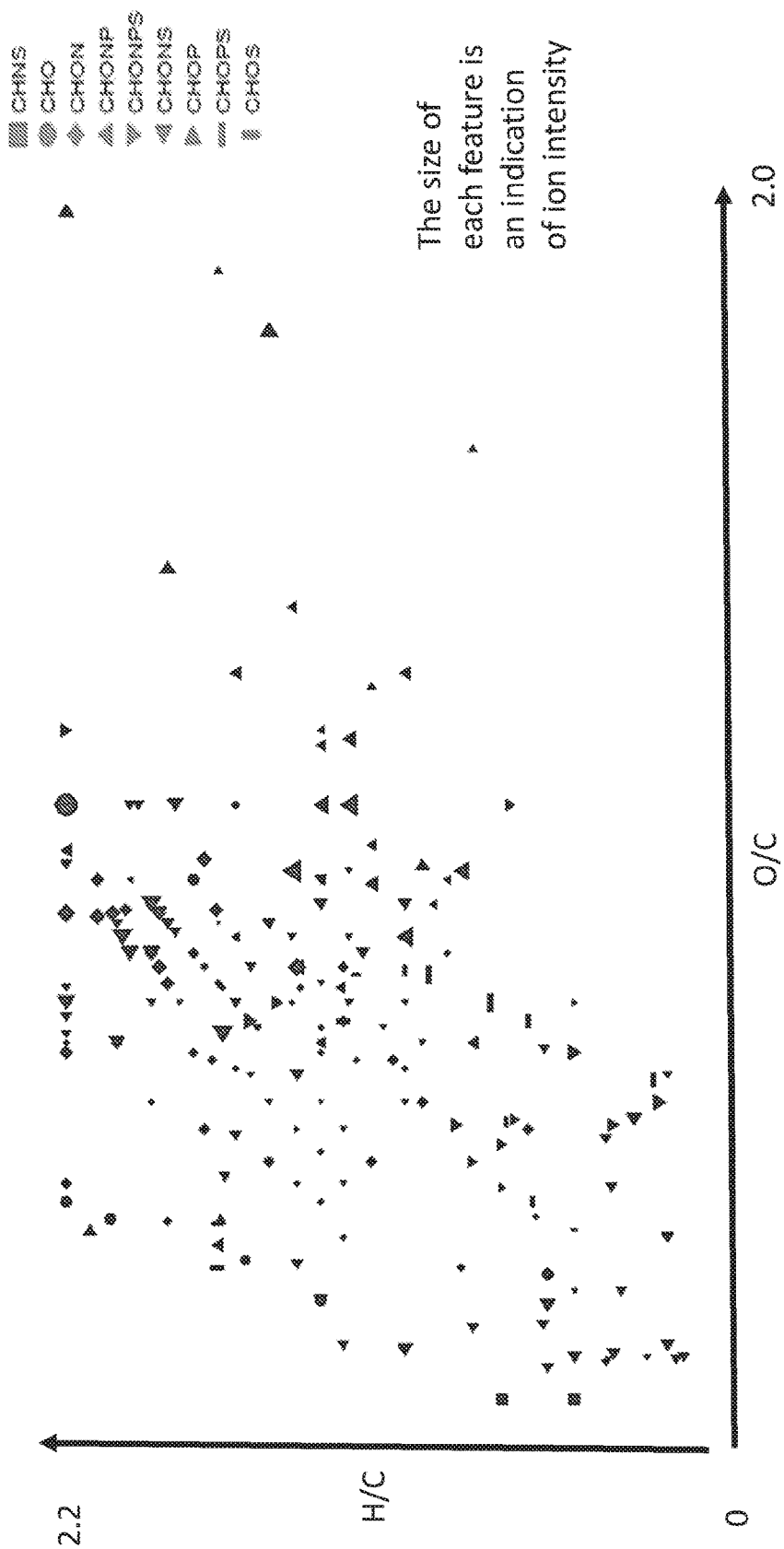
FIG. 14C. Van Krevelen diagram showing the levels of some chemical compounds in the pet food product prior to thermal processing ($t_0$).
Figure 14D:
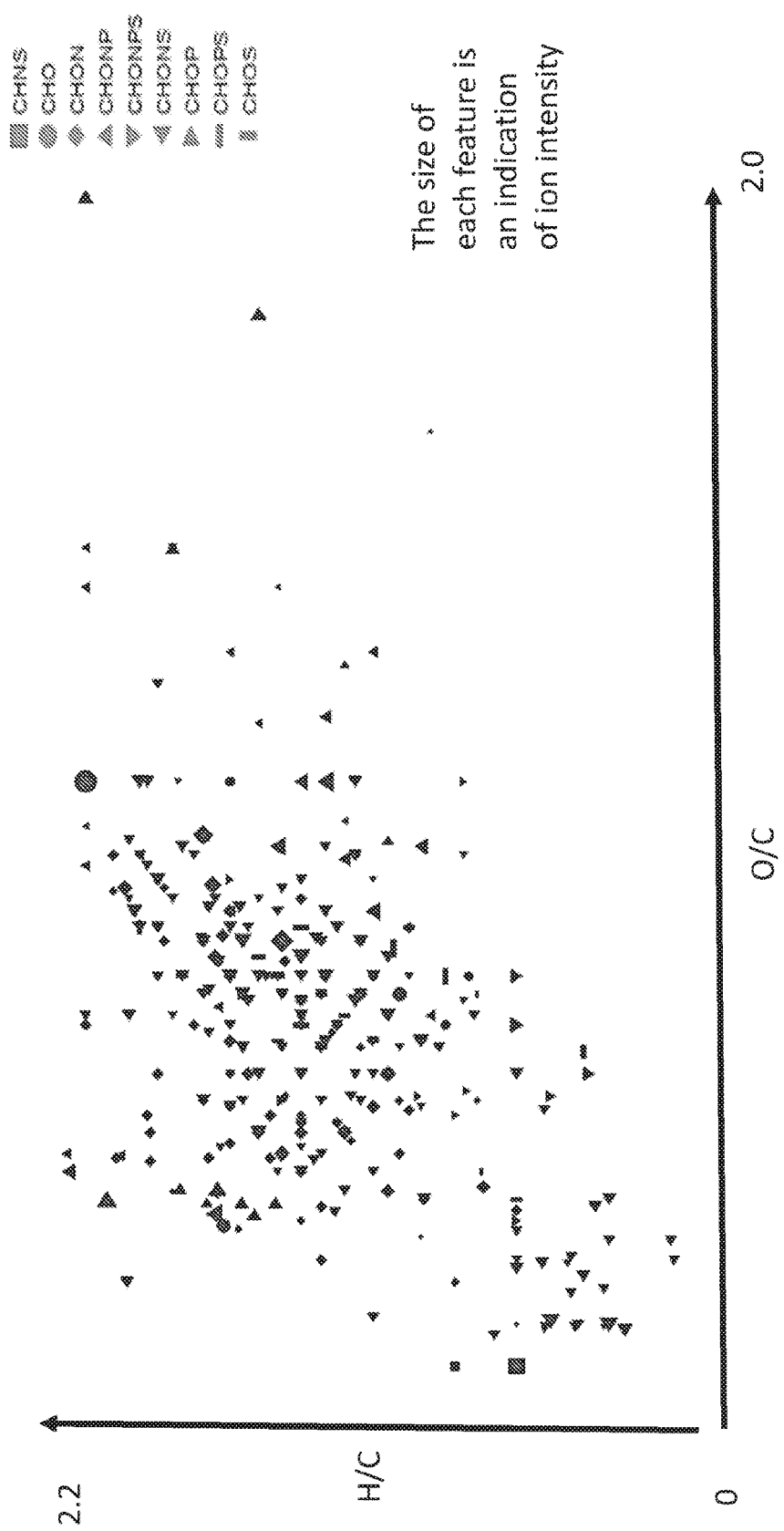
FIG. 14D. Van Krevelen diagram showing the levels of some chemical compounds in the pet food product after thermal processing ($t_6$).

FIG. 13 shows the composition of 7 samples obtained during the thermal processing of a pet food product in a lab-scale process. FIG. 14 shows the composition of the pet food at time point 0 ($t_0$) (FIG. 14A; before processing) and at time point 6 ($t_6$) (FIG. 14B; after processing). Visualization of the differences in composition at $t_0$ as compared to $t_6$ allowed the identification of compounds that increase, decrease, undergo degradation and/or be generated over time during the production process. FIG. 14C shows the compounds that were present at the highest concentrations in $t_0$ and FIG. 14D shows the compounds that were present at the highest concentrations in $t_6$. As shown in FIGS. 14C and 14D, the most prominent compound (as indicated by the largest bubble and solid arrows) was present at both time points $t_0$ and $t_6$; however, it decreased in ion intensity by approximately half between the two time points (e.g., between the two samples).

Figure 15A:
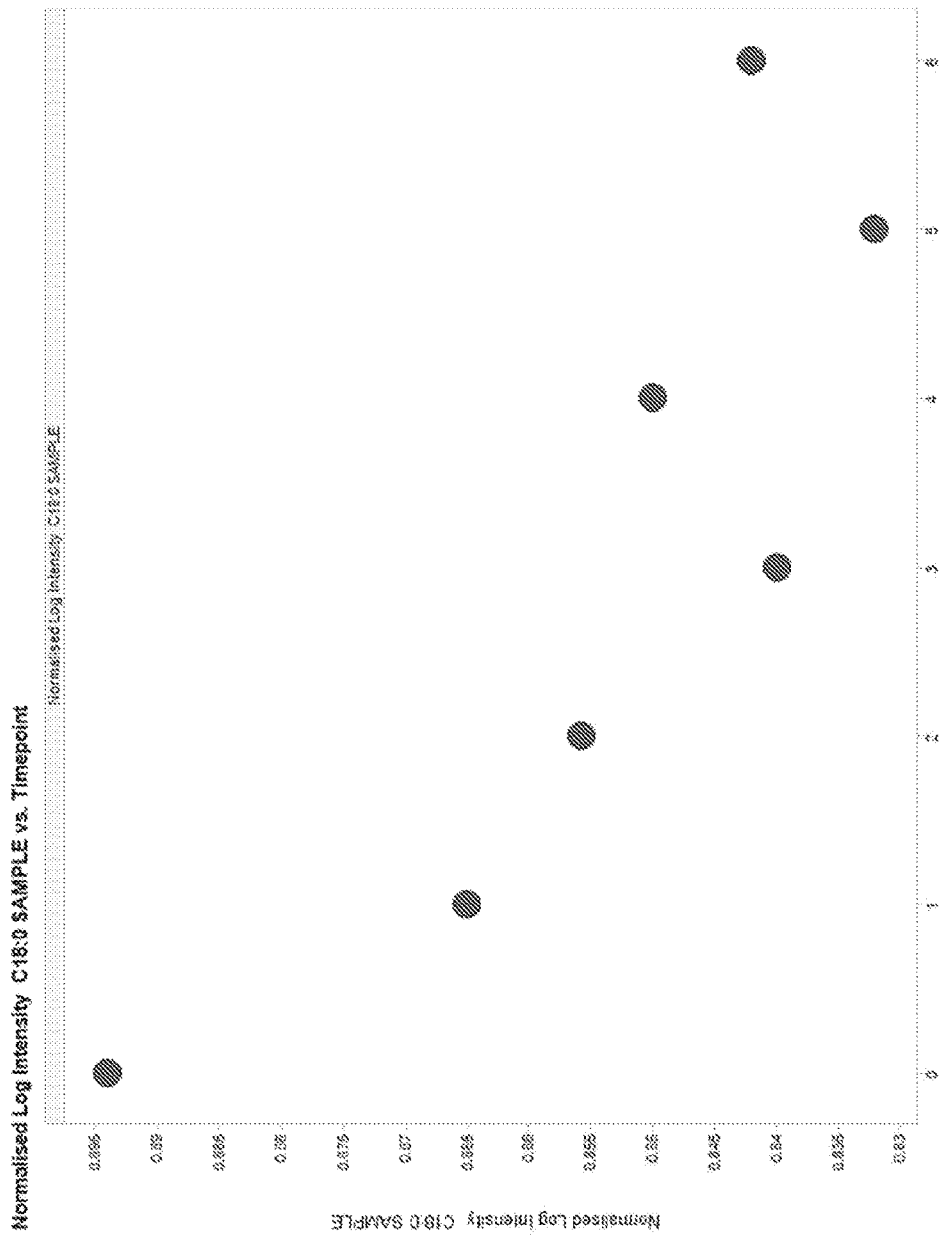
FIG. 15A. Ion intensity plot showing the levels of uridine monophosphate (UMP) during the production process of a pet food.
Figure 15B:
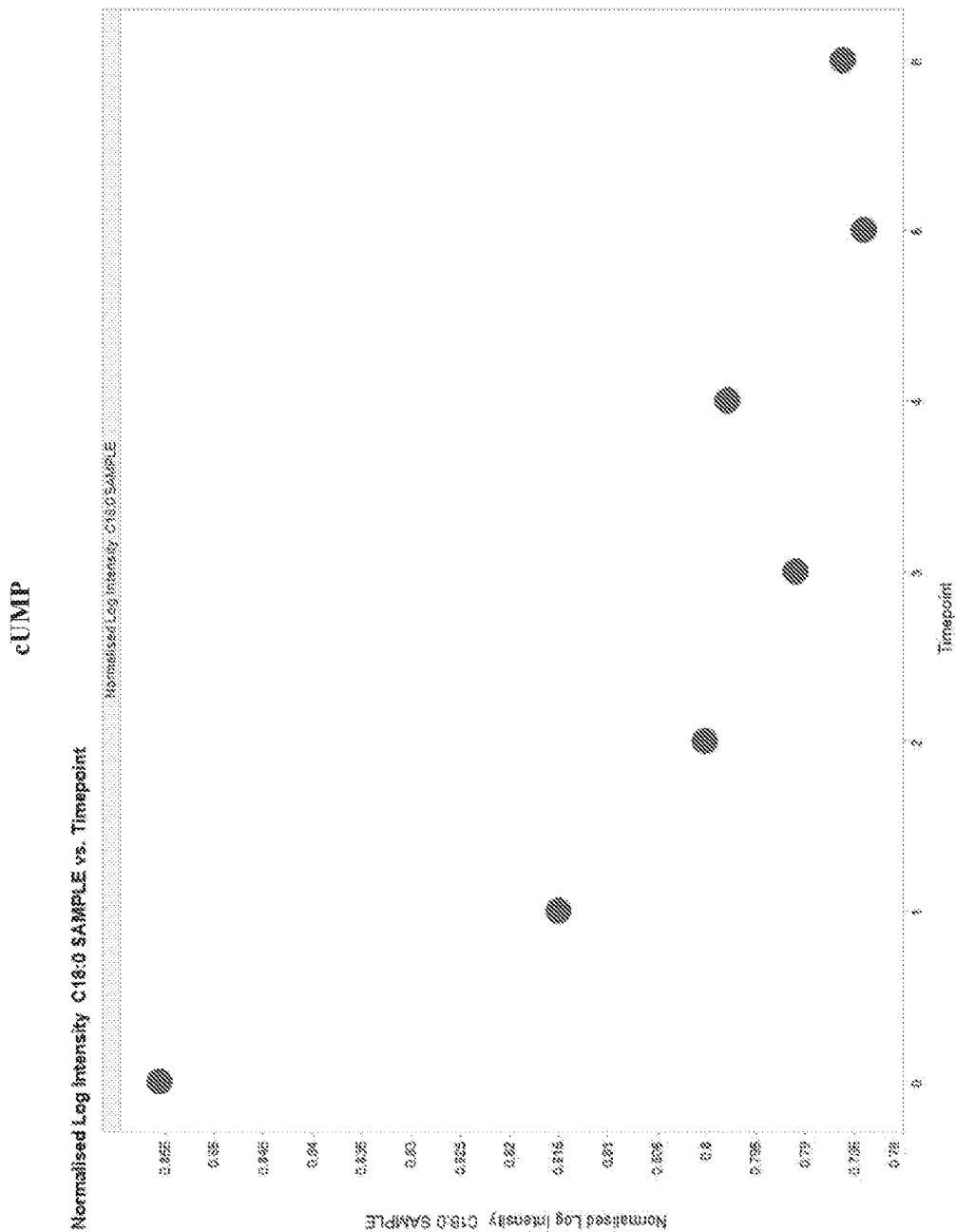
FIG. 15B. Ion intensity plot showing the levels of cyclic uridine monophosphate (cUMP) during the production process of a pet food.
Figure 15C:
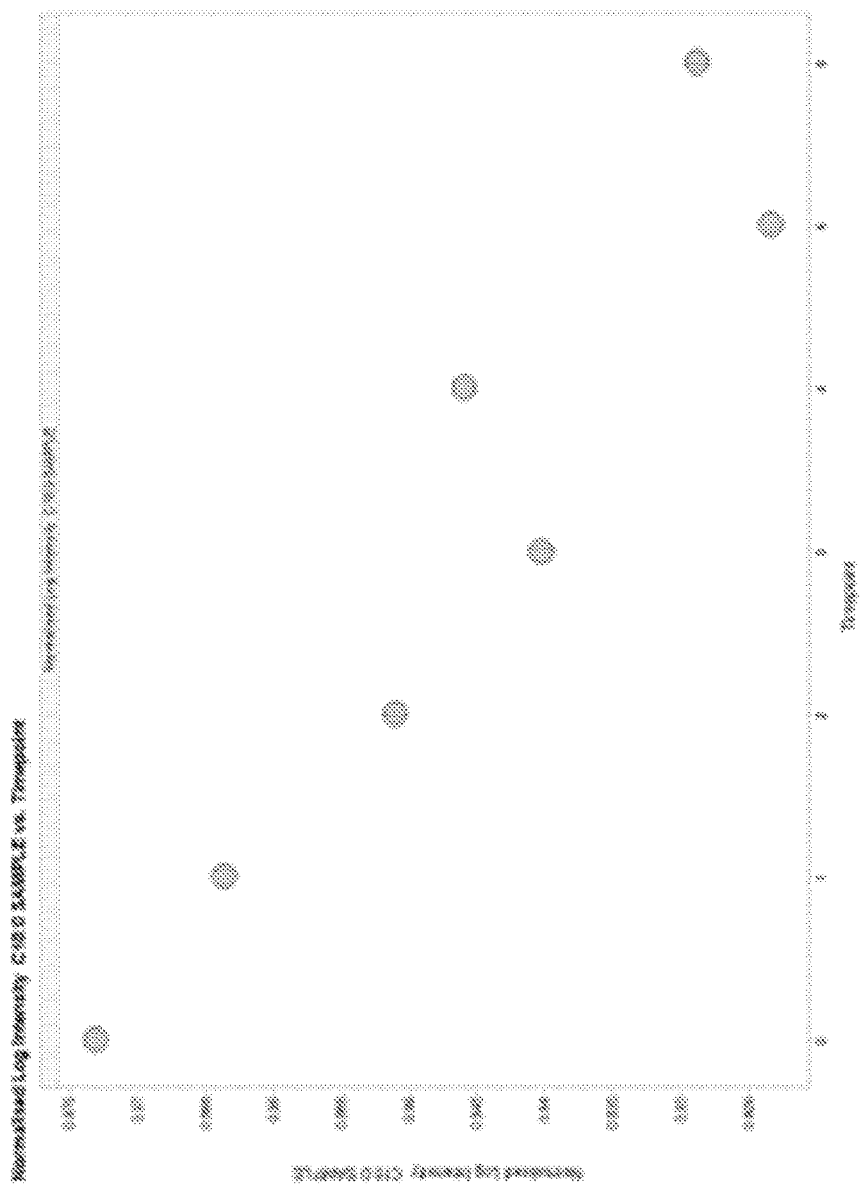
FIG. 15C. Ion intensity plot showing the levels of $C_6$ sugar phosphates during the production process of a pet food.
Figure 15D:
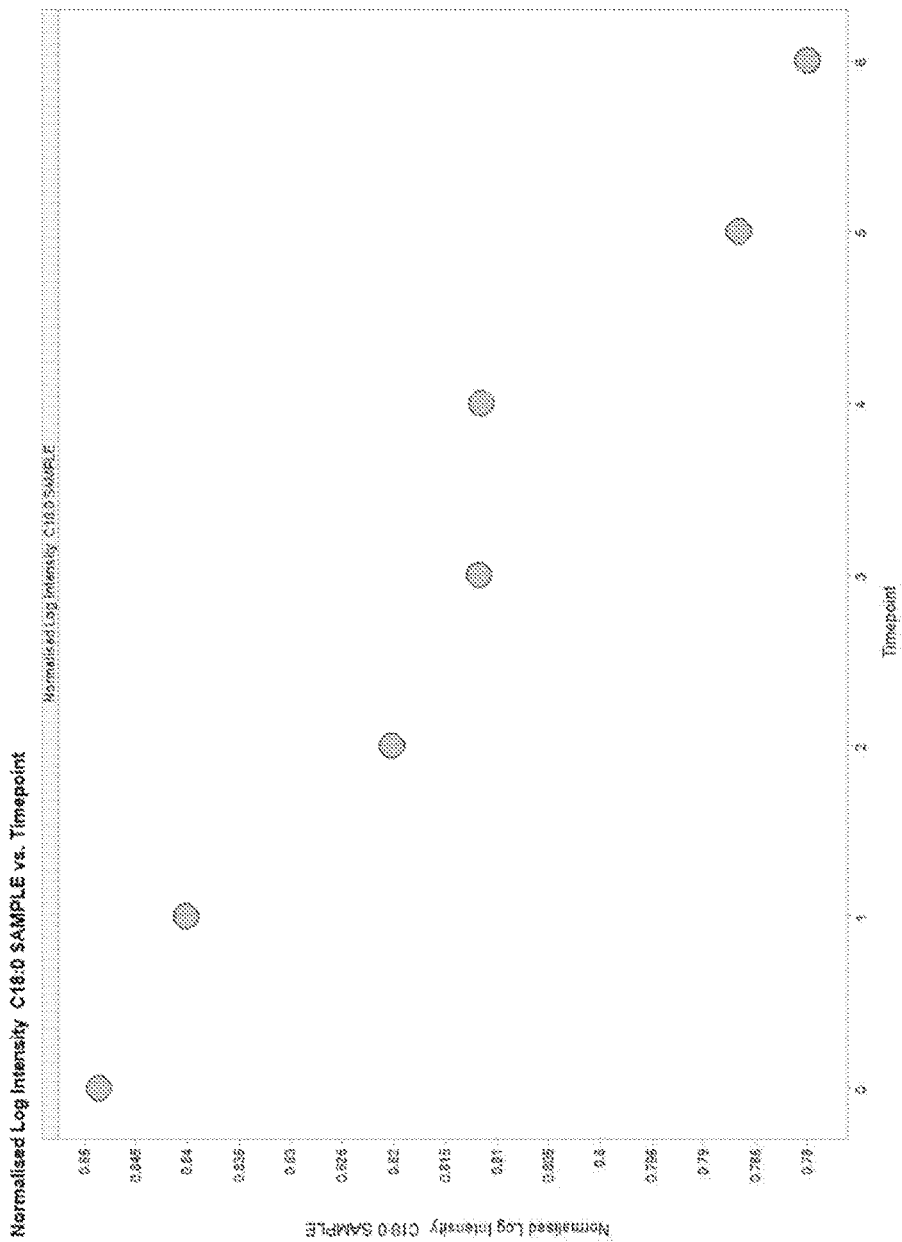
FIG. 15D. Ion intensity plot showing the levels of $C_5$ sugar phosphates during the production process of a pet food.
Figure 15E:
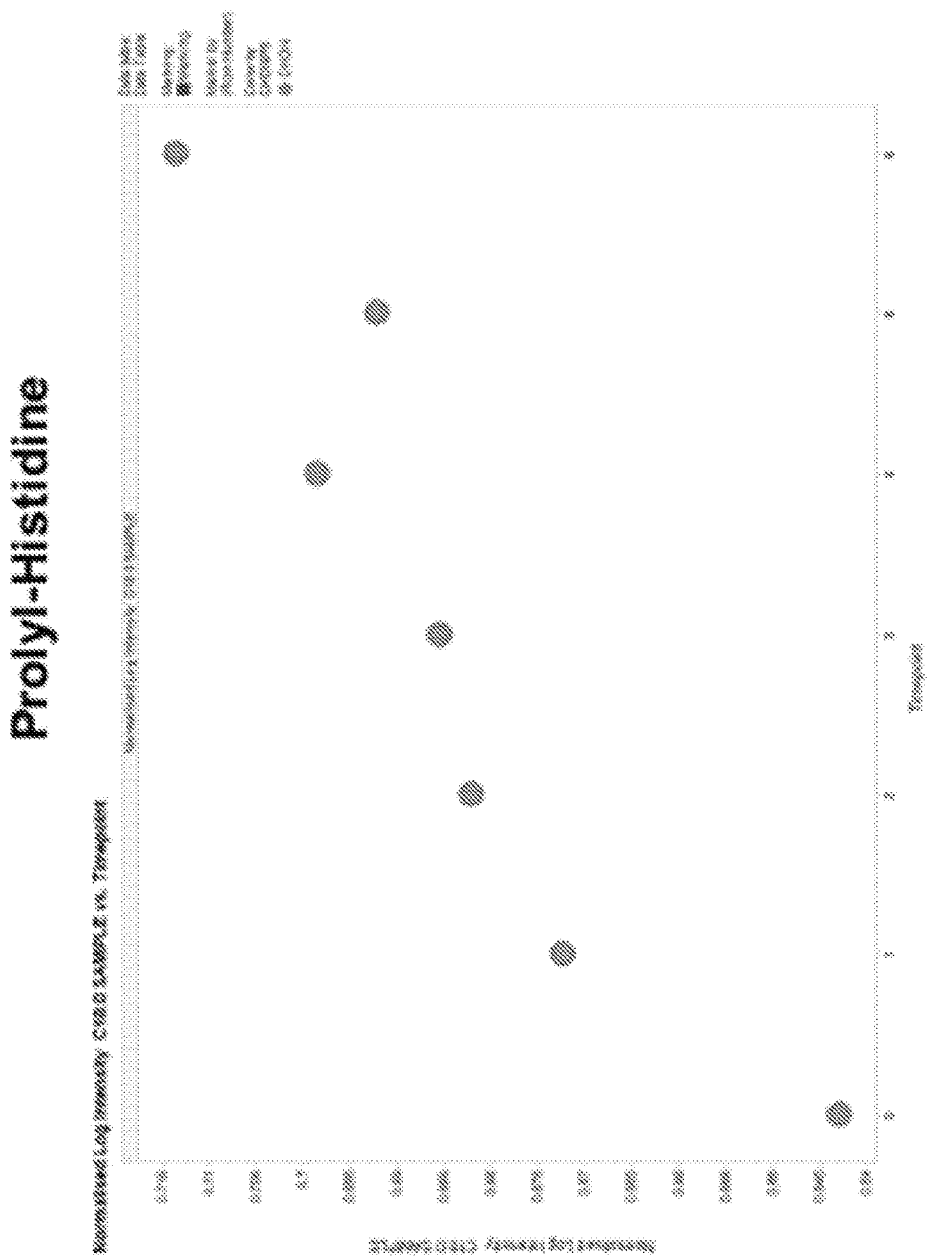
FIG. 15E. Ion intensity plot showing the levels of prolyl-histidine during the production process of a pet food.

As shown in FIG. 14D, further filtering of the data of FIG. 13, allowed the monitoring of specific compounds, such as uridine monophosphate (UMP), cyclic uridine monophosphate (cUMP), sugar phosphates and peptides over time (dashed arrows). As shown in FIG. 15, during production of the pet food product, as determined by the analysis of multiple time points, the levels of UMP (FIG. 15A) and cUMP (FIG. 15B) decreased over time. In addition, the levels of sugar phosphates, $C_6H_{13}O_9P$ (FIG. 15C) and $C_5H_{11}O_8P$ (FIG. 15D), were also determined to be consumed during the production of the pet food product. As shown in FIG. 15E, the level of the dipeptide prolyl-histidine increased over time, which suggests the occurrence of at least some protein hydrolysis during production of the pet food.

Figure 16:
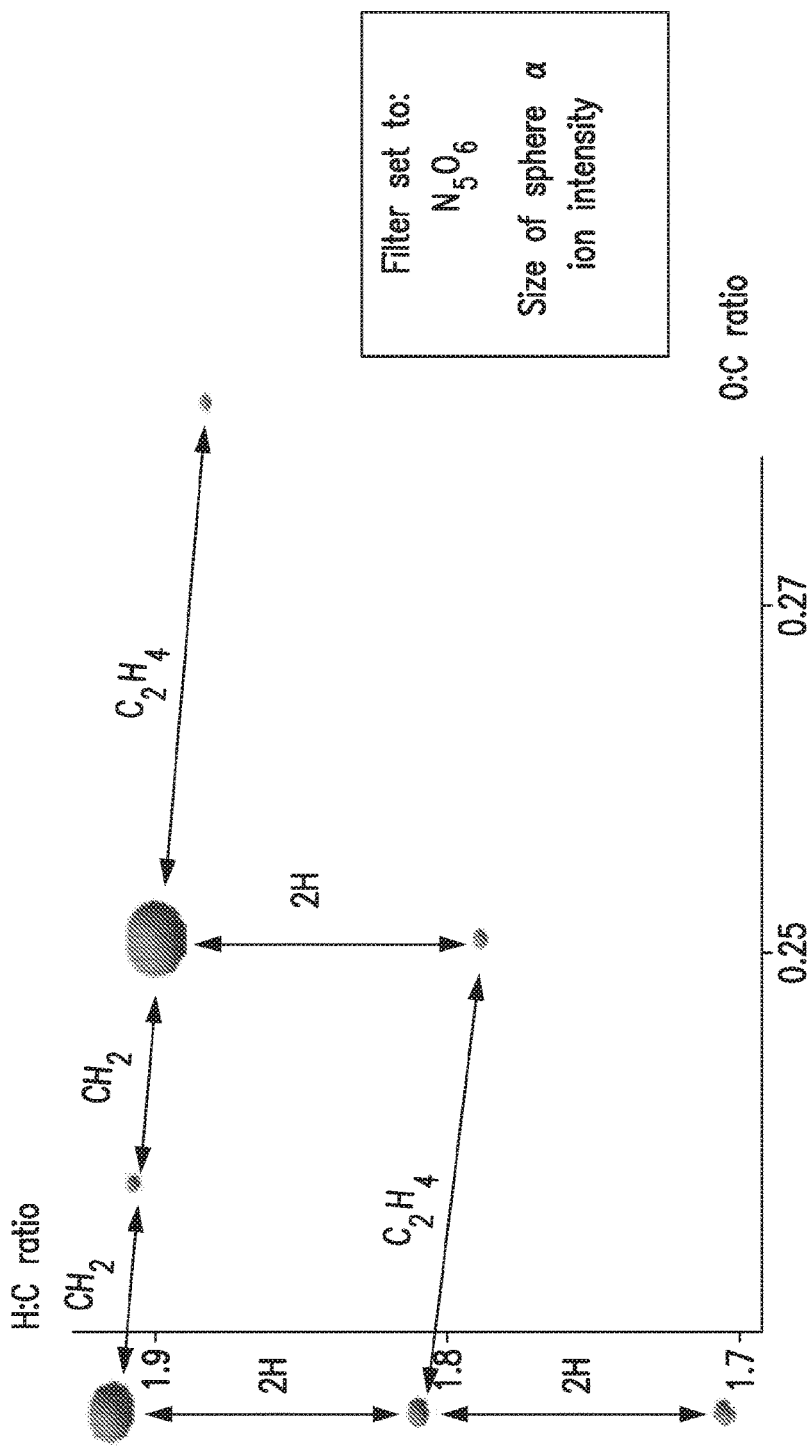
FIG. 16. Van Krevelen diagram produced by selecting a filter setting having a particular nitrogen to oxygen ratio to display neutral pentapeptides.
Figure 17A:
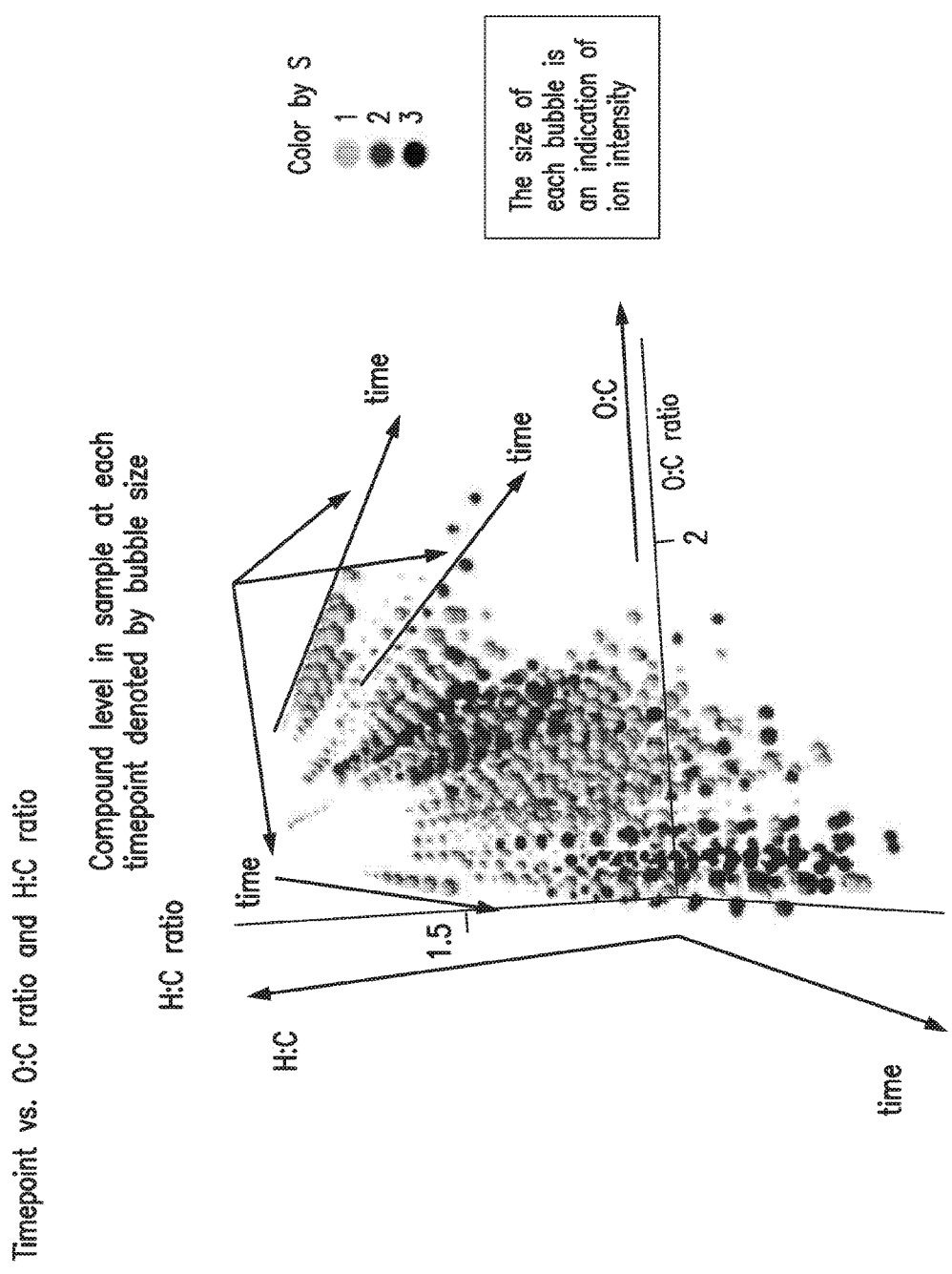
FIG. 17A. Van Krevelen diagram depicting the changes in the levels of sulfur compounds during the processing a pet food product. Sulfur compounds present within 7 samples obtained during the production process of a pet food product are shown.
Figure 17B:
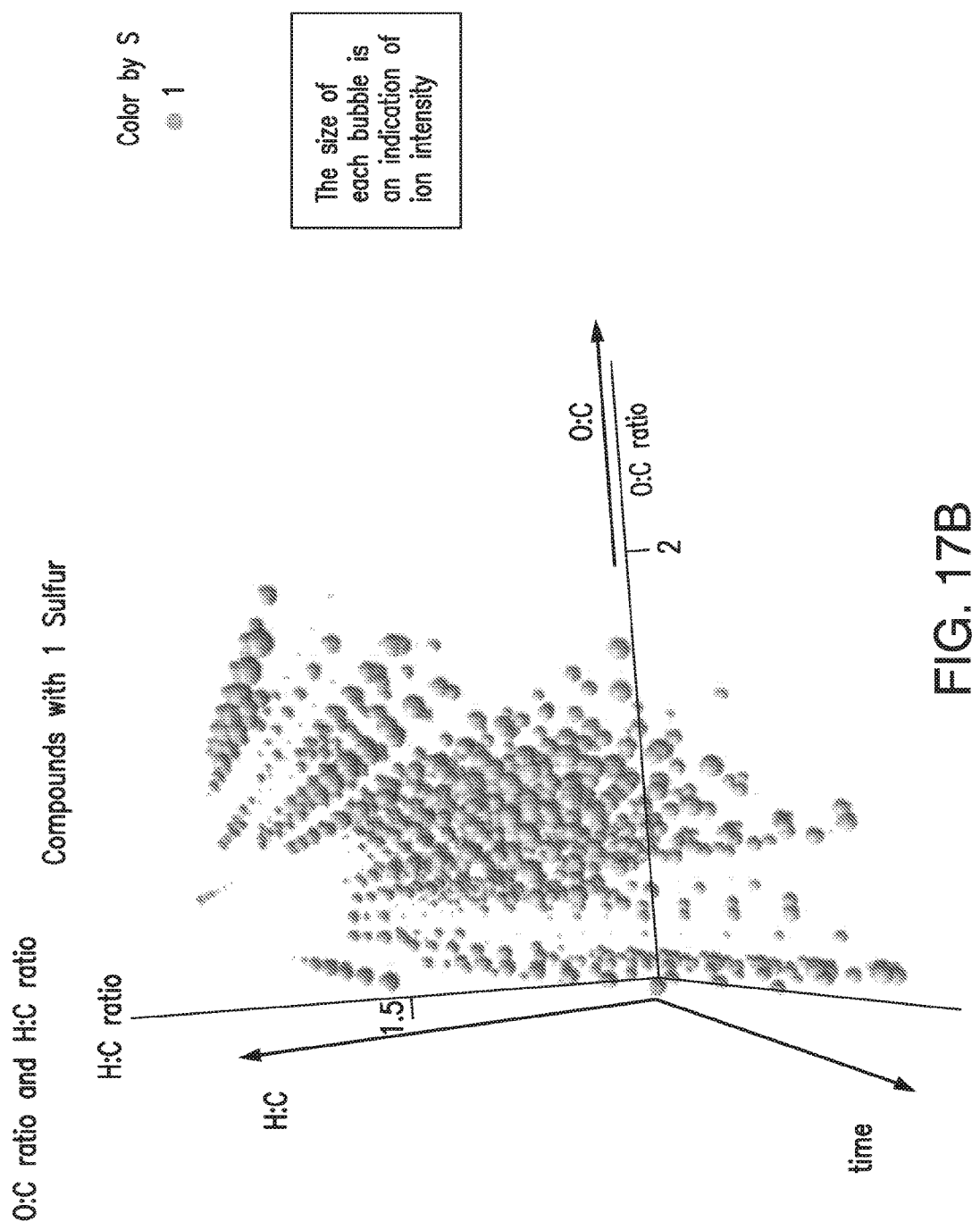
FIG. 17B. Van Krevelen diagram of the level of compounds containing 1 sulfur atom during the processing of a pet food product.
Figure 17C:
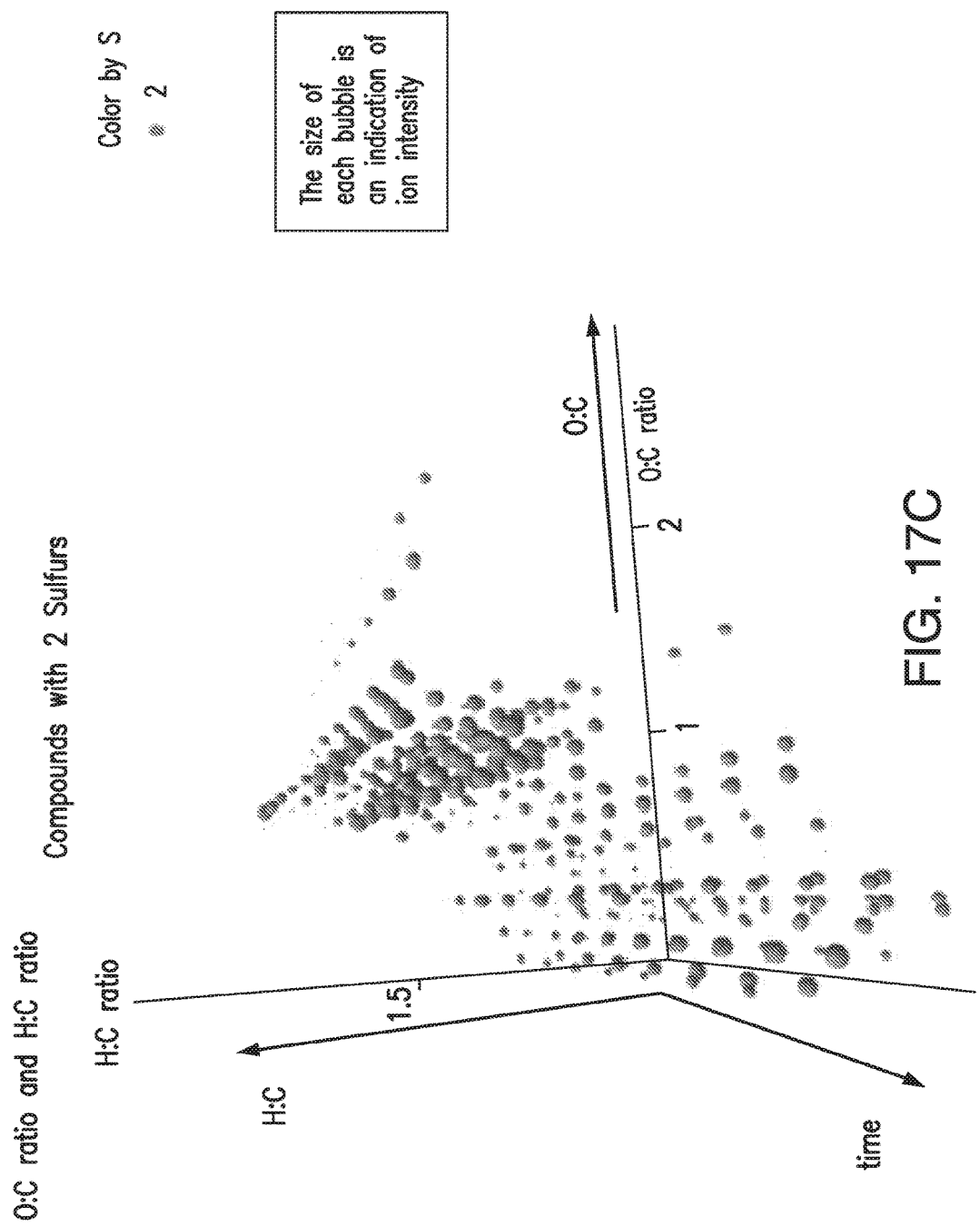
FIG. 17C. Van Krevelen diagram of the level of compounds containing 2 sulfur atoms during the processing of a pet food product.
Figure 17E:
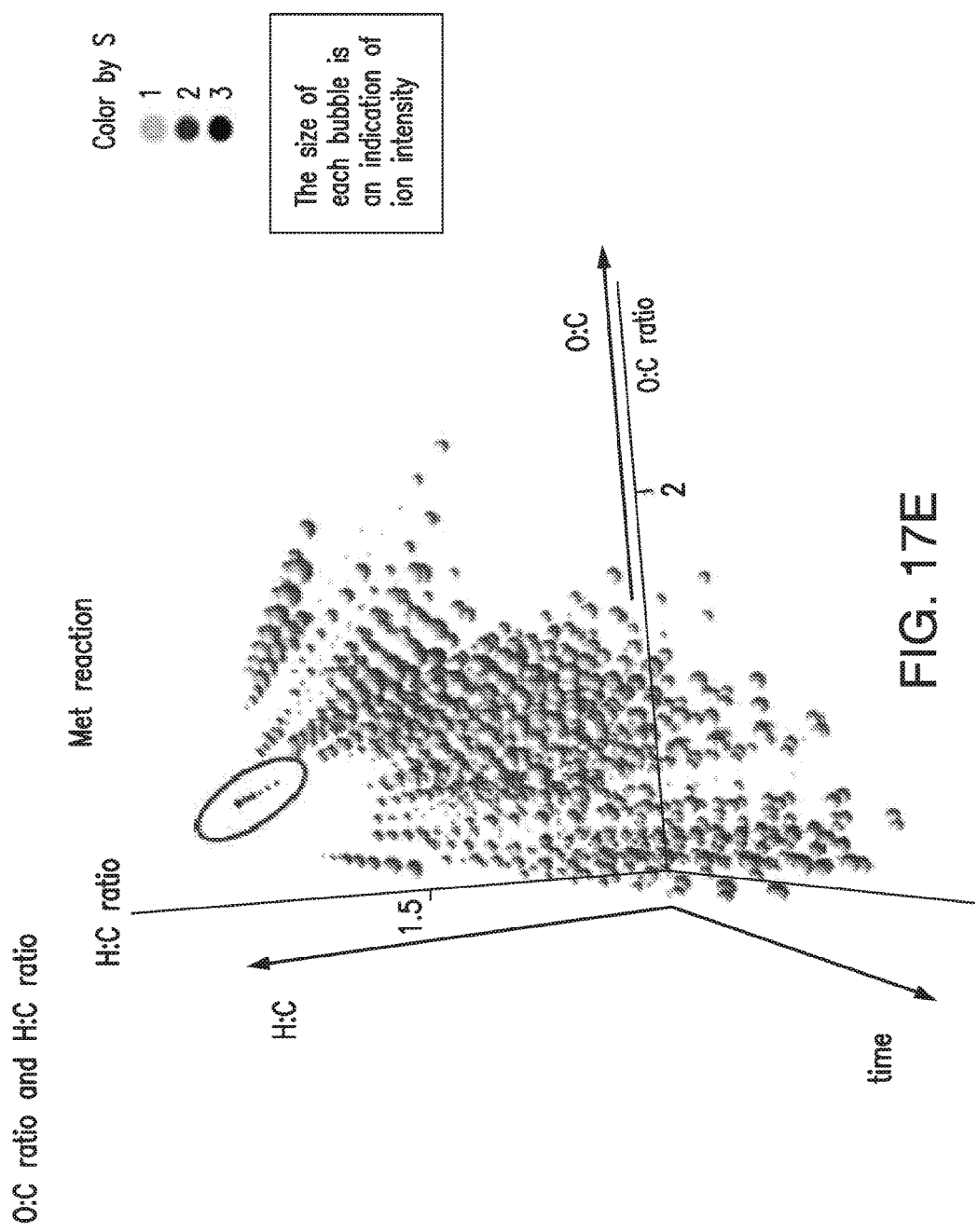
FIG. 17E. Van Krevelen diagram of the level of methionine during the processing of a pet food product. The region of the diagram corresponding to the decrease in the level of methionine is circled.
Figure 17F:
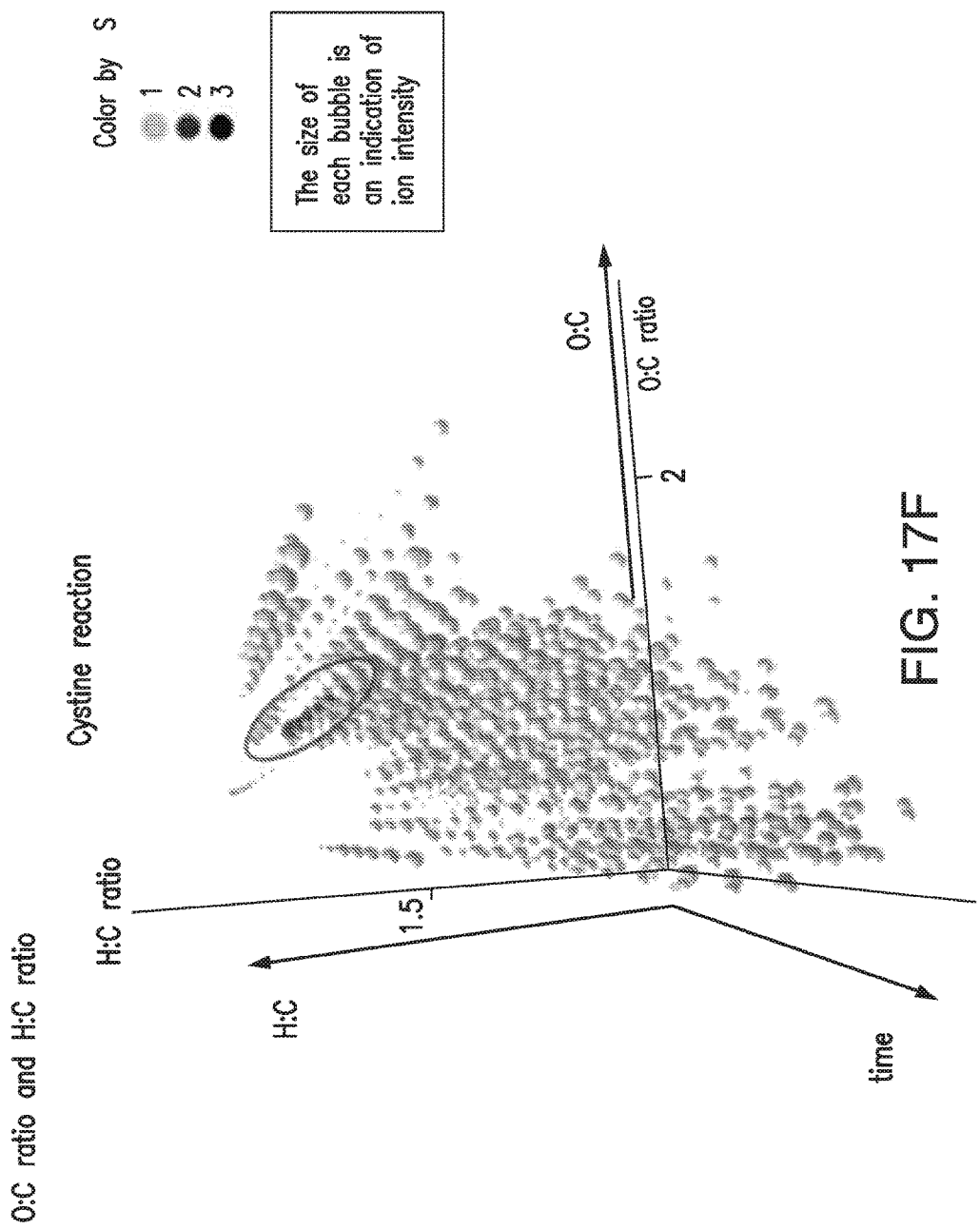
FIG. 17F. Van Krevelen diagram of the level of cystine during the processing of a pet food product. The region of the diagram corresponding to the decrease in the level of cystine is circled.

In addition, as described above, the filtering of uHRMS data sets can allow the identification and monitoring of specific classes of compounds. As shown in FIG. 16, filtering of the uHRMS data set for compounds containing $N_5O_6$ can result in the isolation of neutral pentapeptides, e.g., peptides containing no acidic or basic amino acids. In addition, as shown in FIG. 17, the evolution of sulfur-containing compounds can be analyzed during processing of a pet food product. FIG. 17A shows a comparison of the sulfur compounds in 7 samples obtained during the thermal processing of a wet pet food product, and further indicates the number of sulfur atoms in each of the identified compounds. FIGS. 17B-E further show the compounds that have a specific number of sulfur atoms. FIG. 17B shows the change in the level of the compounds that have only 1 sulfur atom during the production of the pet food. FIG. 17C shows the compounds that have only 2 sulfur atoms and FIG. 17D shows the compounds that have 3 sulfur atoms. The filtering of the data to only visualize compounds that include sulfur atoms allows the monitoring of the levels of amino acids that include one or more sulfur atoms over time and amino acids that are considered essential amino acids. For example, the amino acid methionine is an essential amino acid for dogs and cats and needs to be provided to the animal as part of their diet. Therefore, the presently disclosed methods can be used to analyze the levels of methionine during the production of a pet food to ensure that the final pet food product contains the correct levels of the essential amino acids. As shown in FIG. 17E, methionine ("Met"), which includes one sulfur atom, was determined to decrease over time during the production of the wet pet food. In FIG. 17E, the circled area shows the region of the van Krevelen diagram corresponding to the decrease in methionine. In addition, the amino acid cystine, which includes two sulfur atoms was also determined to decrease over time, suggesting that these amino acids were consumed, for example, in one or more Maillard reactions. In FIG. 17F, the circled area shows the region corresponding to the decrease in cystine.

Some additional chemical processes were investigated using the disclosed methods included the release of phosphate (and subsequent onward reaction) and the reaction of key nutrients such as taurine. The results obtained with taurine suggest that taurine is involved in condensation reactions. Data obtained from uHRMS followed by data interrogation can also be used to compare product compositions. Different final products can be analyzed by uHRMS and the data can be filtered to identify and analyze the differences in fatty acid levels within the multiple products. For example, in FIG. 18, a van Krevelen diagram displays data from 8 different commercially available pet food products to compare fatty acid levels. For example, C18:3 depicted in FIG. 18 refers to a fatty acid with 18 carbons in the backbone and 3 double bonds (unsaturations).

These data show that is possible to combine the use of FT-ICR-MS measurements with a lab-scale pet food sterilization process, which allows the pet food to be sampled and analyzed at different time points throughout sterilization. The high mass resolution and the excellent mass accuracy of FT-ICR-MS, allowed the changing chemical fingerprint of pet food to be evaluated statistically throughout the "cook" phase (i.e., thermal processing phase). Statistical changes in the chemical fingerprint of pet food were chemically interpreted using molecular formula predictions, by comparison to accurate mass databases and also by interpreting the exact mass differences between those chemical compounds which changed to determine the nature of chemical reactions that occur during thermal processing.

Figure 20A:
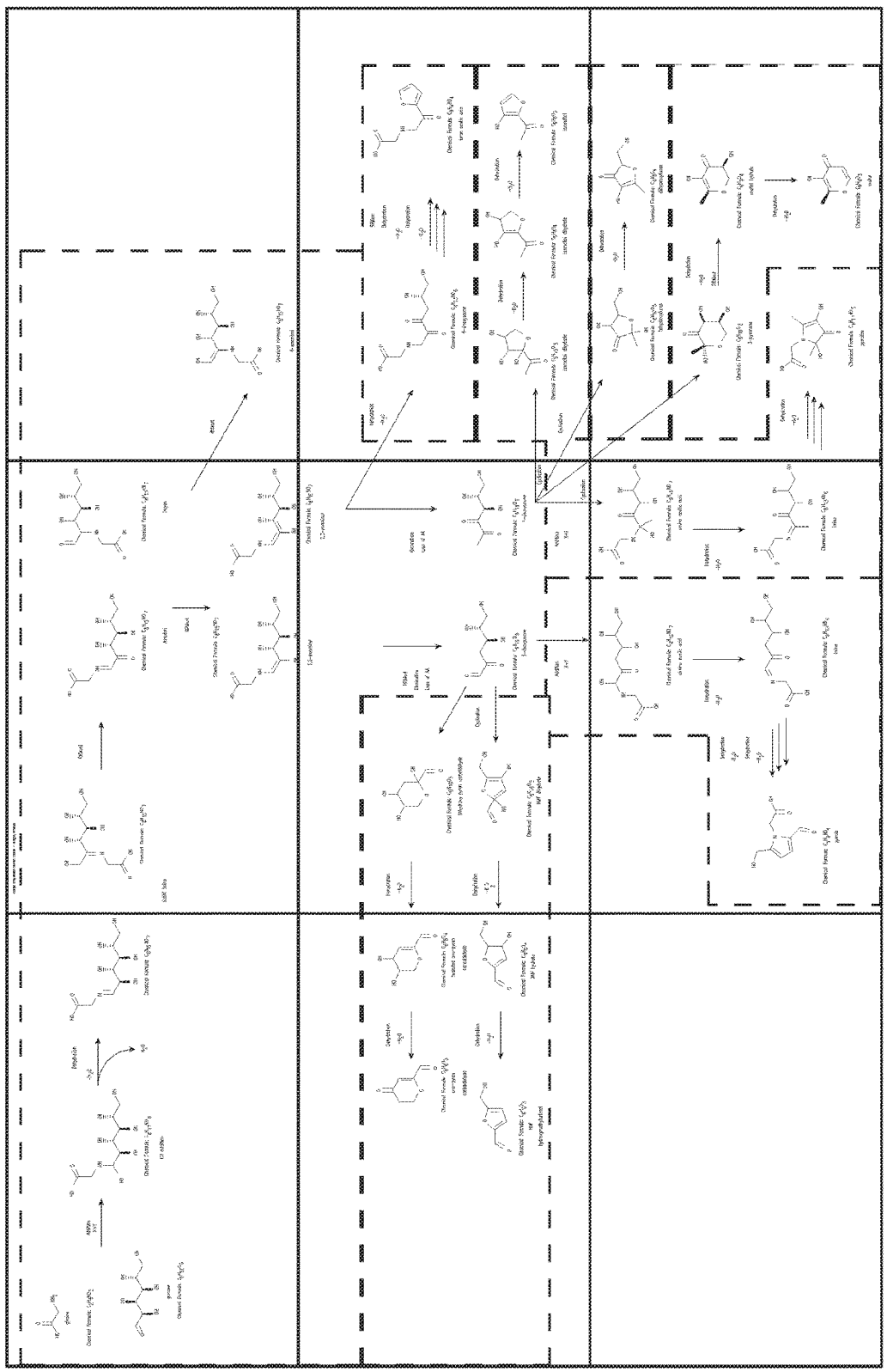
FIG. 20A. An example of a Maillard reaction.
Figure 20A:
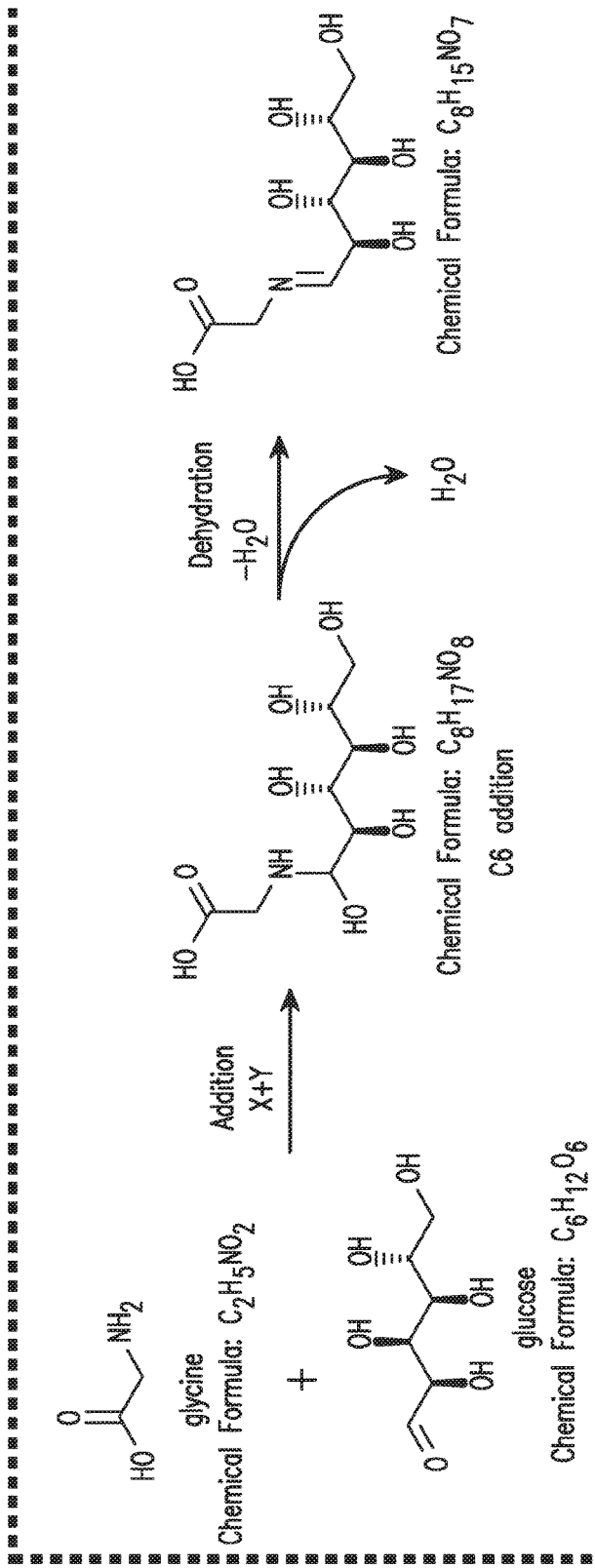
Figure 20A:
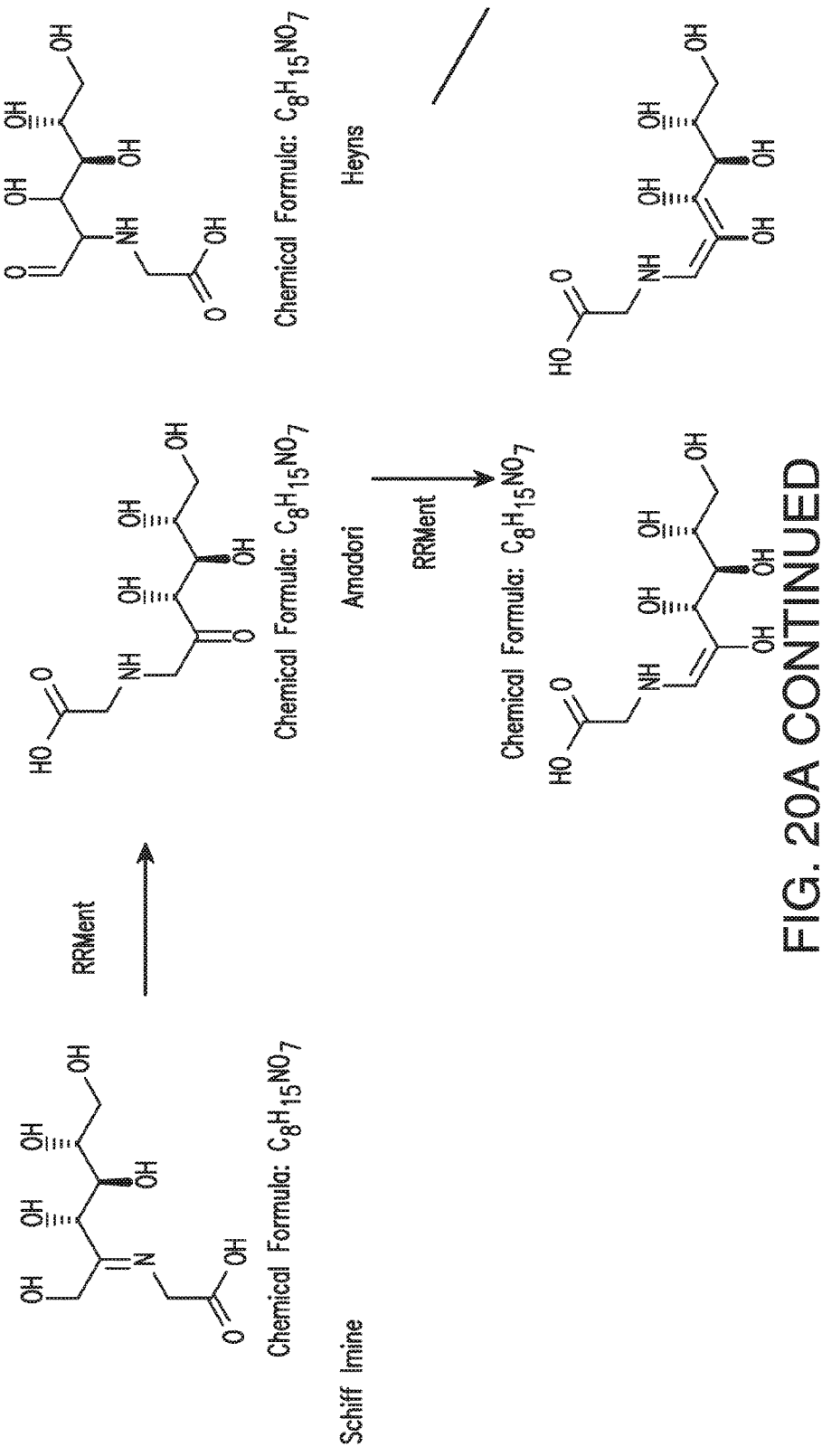
Figure 20A:
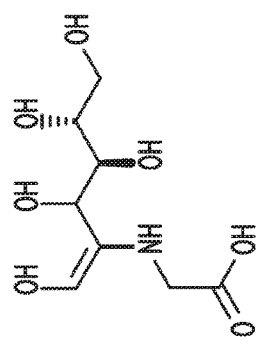
Figure 20A:
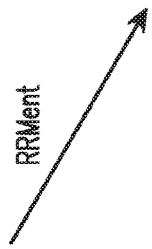
Figure 20A:
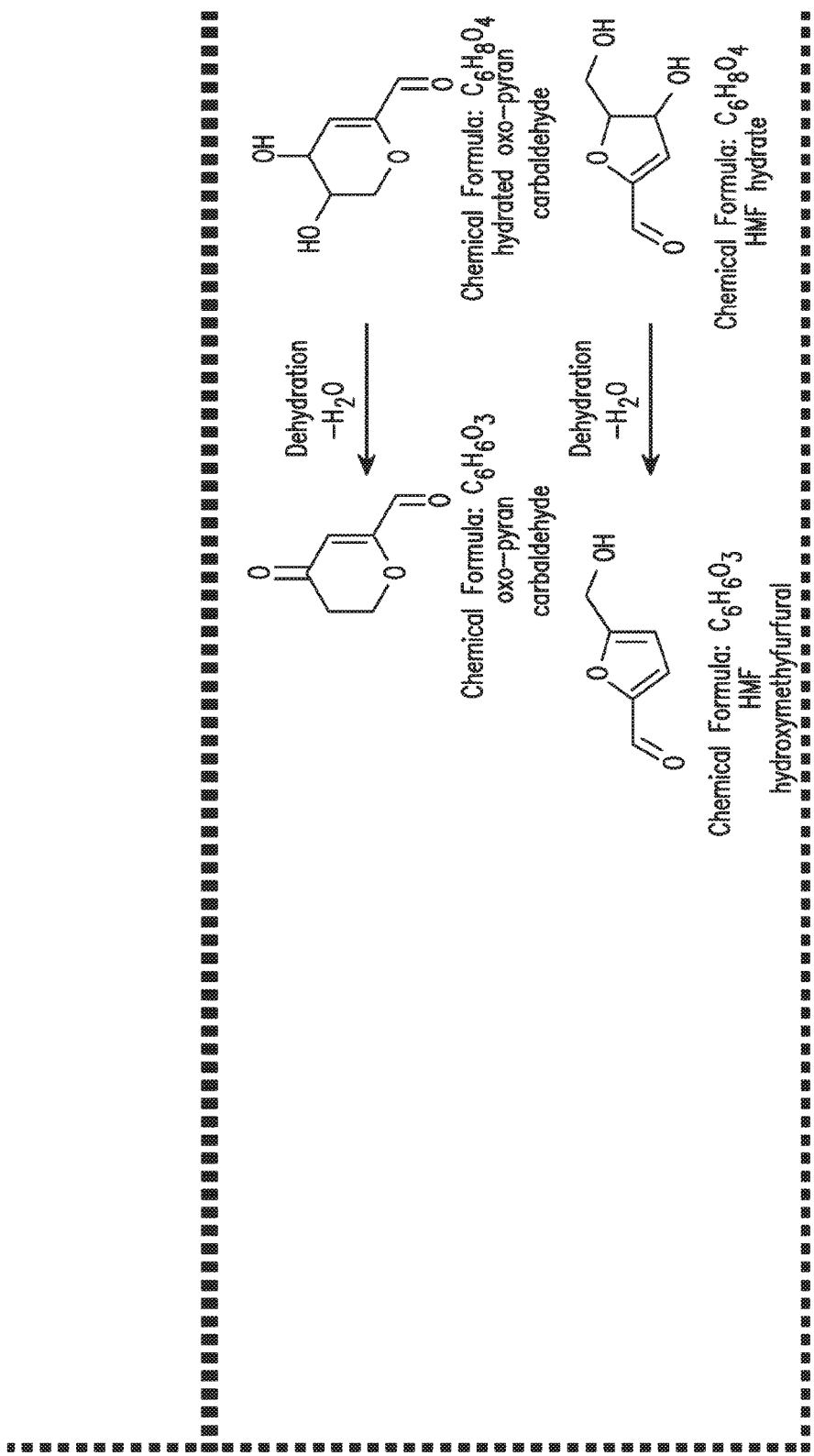
Figure 20A:
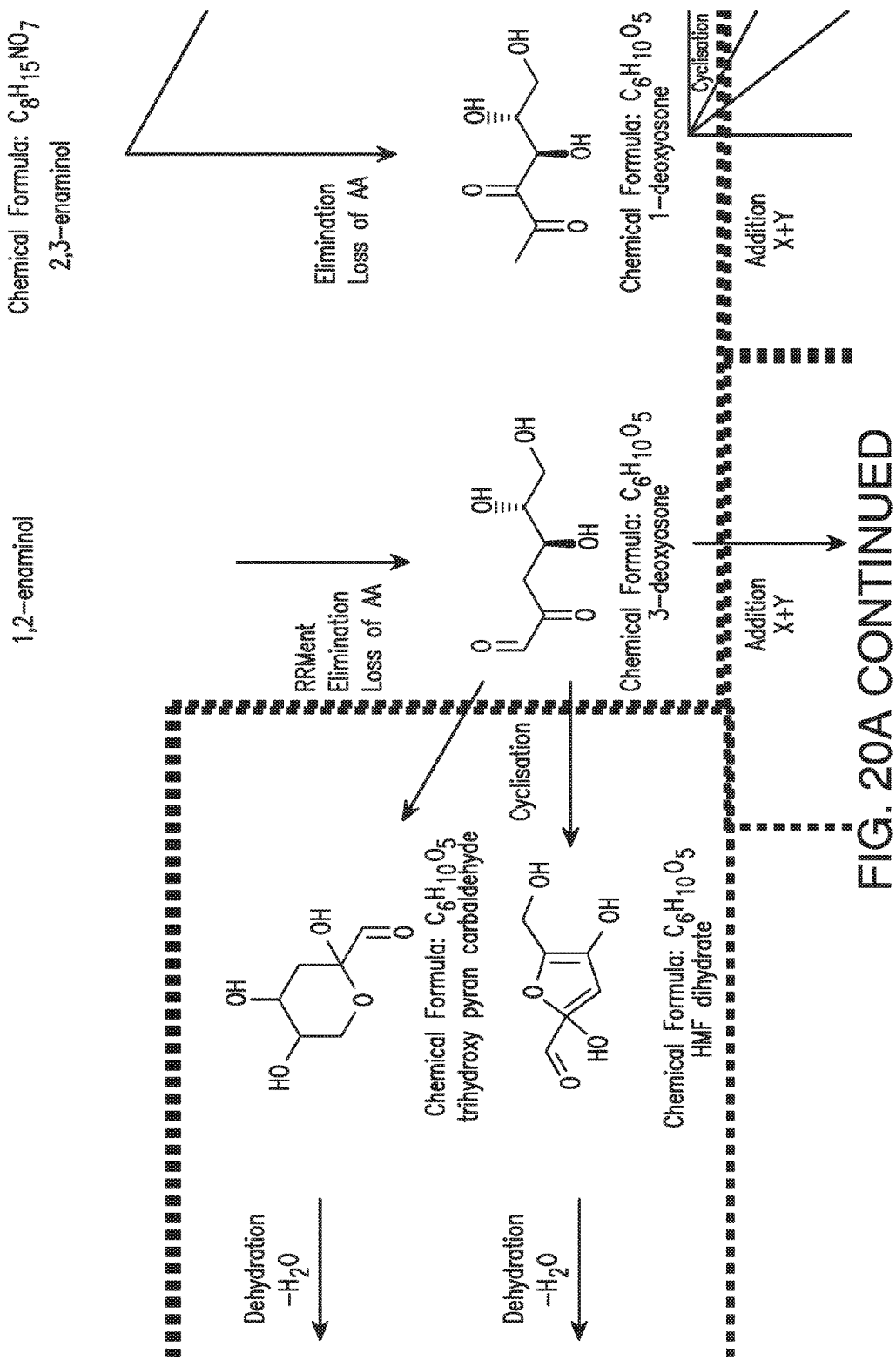
Figure 20A:
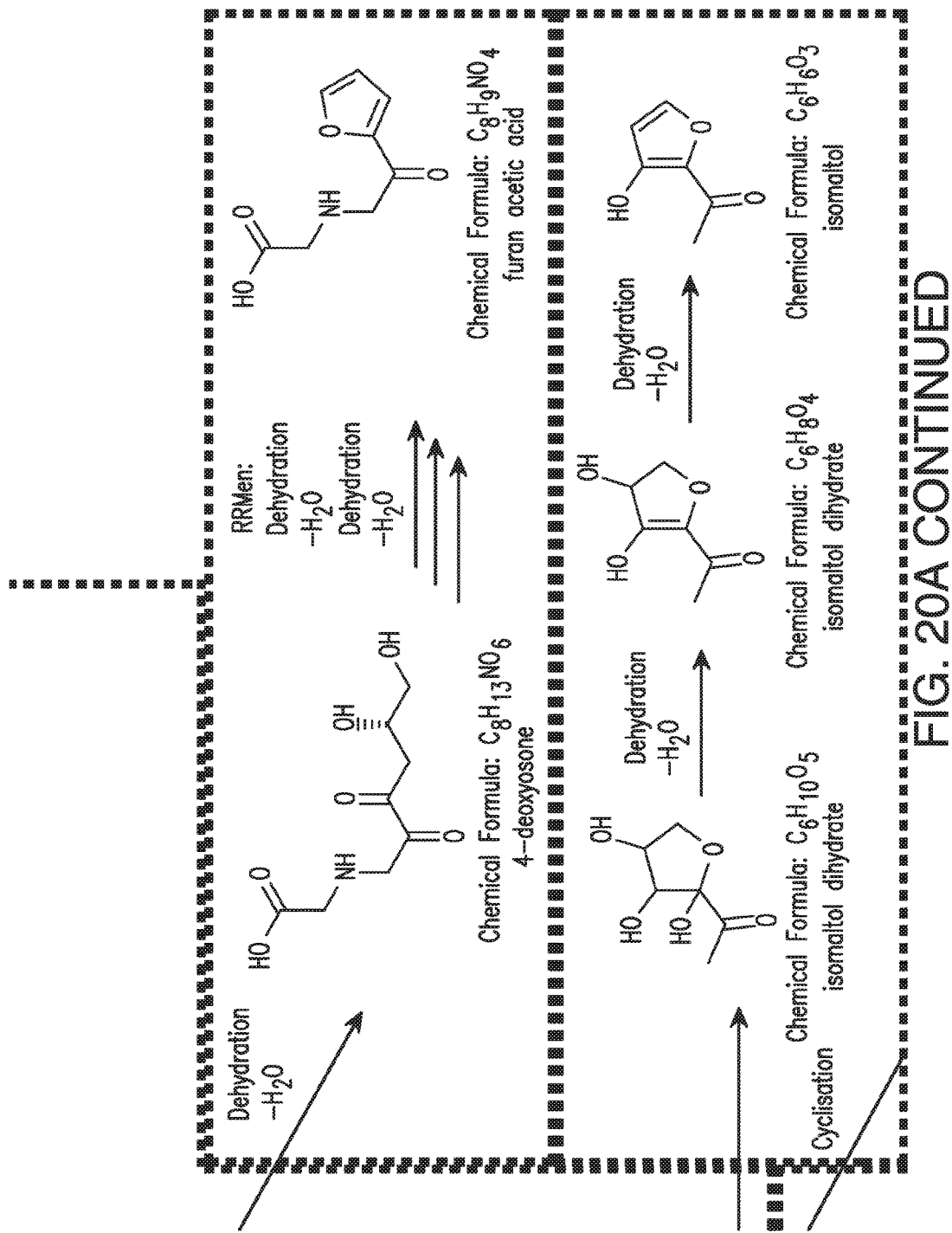
Figure 20A:
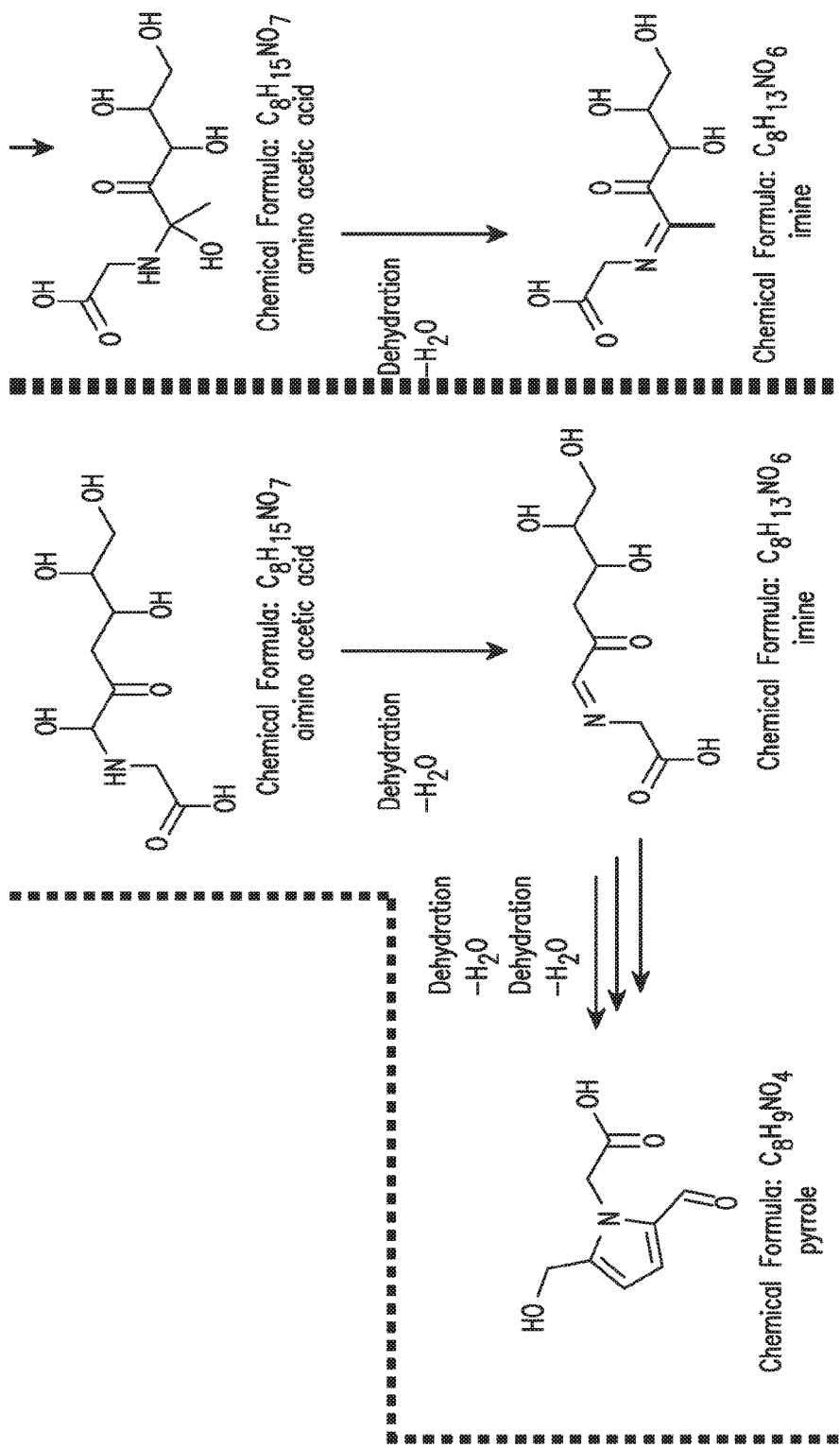
Figure 20A:
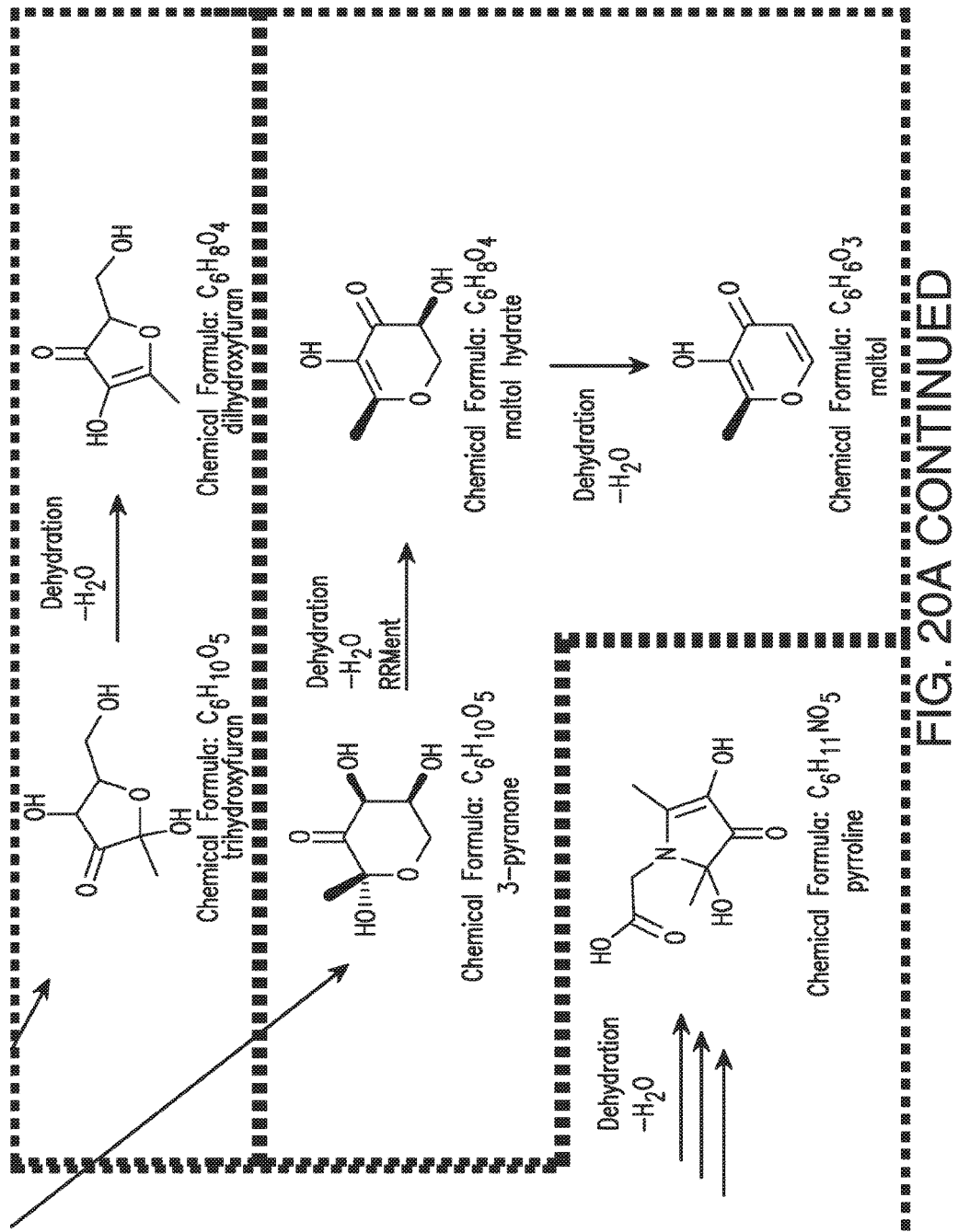

Example 4: Identification, Monitoring, and Modulating of Maillard Reactions Using Ultra High Resolution Mass Spectrometry of Pet Food Products Maillard reactions are chemical reactions between amino acids and reducing sugars that can result in flavor compounds and which contribute greatly to the flavor of food products. Maillard reactions are complex reactions which involve the generation of a number of intermediate compounds and products via a number of different types of reactions, e.g., condensation reactions, addition reactions and dehydration reactions. A non-limiting example of a Maillard reaction is provided in FIG. 20A. FIG. 20B depicts non-limiting examples of different types of chemical reactions that occur during the Maillard reaction, at different steps. For example, in the early phases of the Maillard reaction, the carbonyl group of a sugar can react with the amino group of an amino acid, to produce an N-substituted glycosylamine and water. The glycosylamine compound undergoes Amadori rearrangement to form a ketosamine. Ketosamines can react in a number of ways, for example, by dehydrating to produce water and reductones, or reacting to form diacetyl, acetol, pyruvaldehyde and other short-chain hydrolytic fission products, or reacting to form a Schiff's base. Onward reaction of many of these compounds can, in turn, form melanoidins.

Figure 21A:
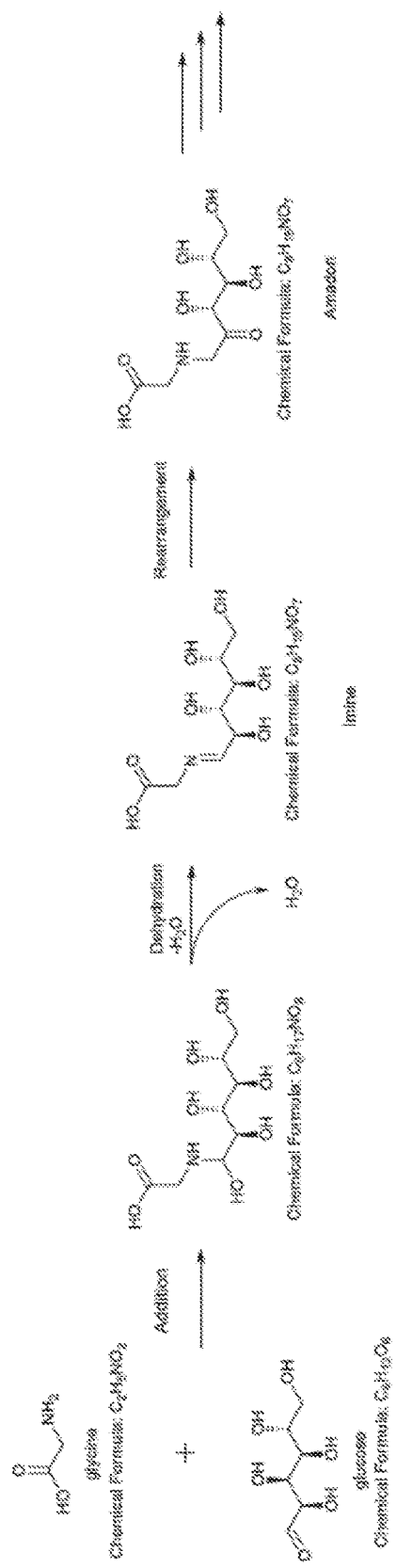
FIG. 21A. Non-limiting examples of the reactants and intermediates generated during the initial stages of a Maillard reaction.
Figure 21B:
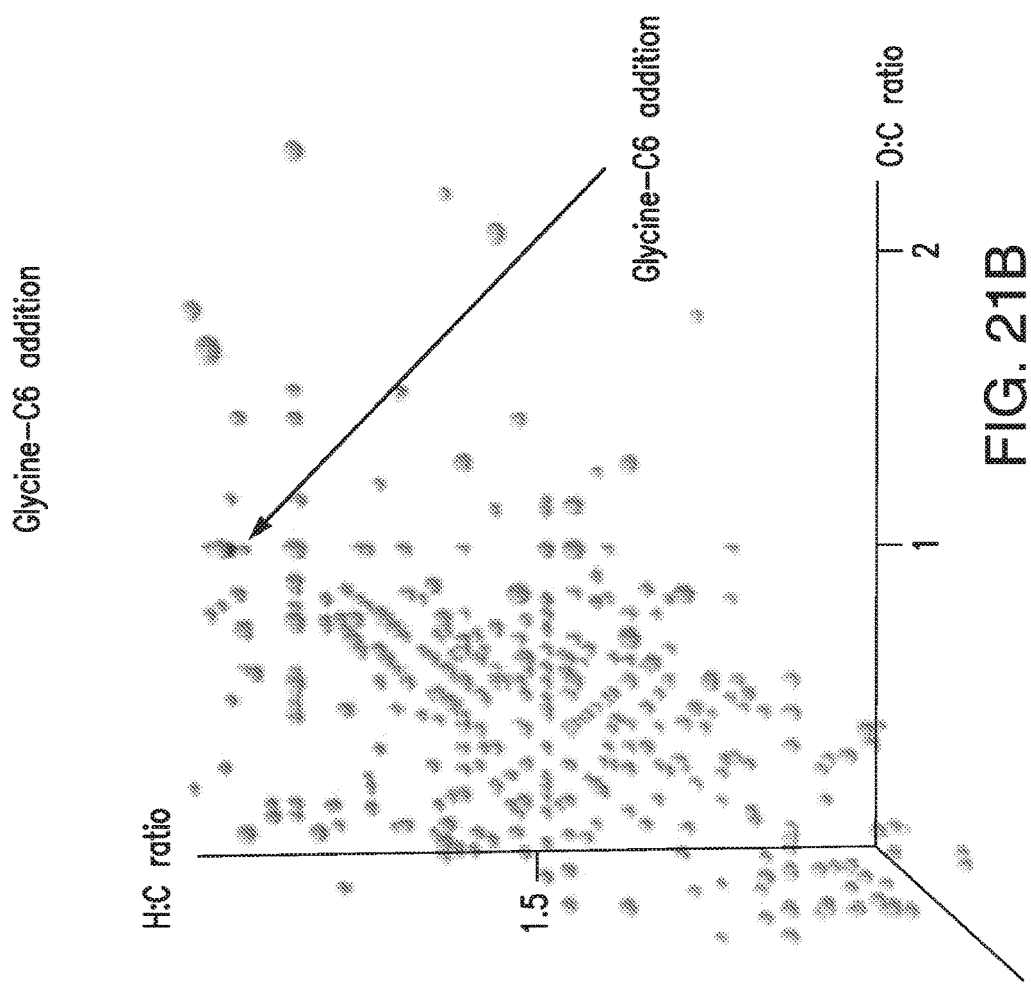
FIG. 21B. Van Krevelen diagram showing the presence of a glycine-$C_6$ sugar addition product during the production of a pet food.
Figure 21C:
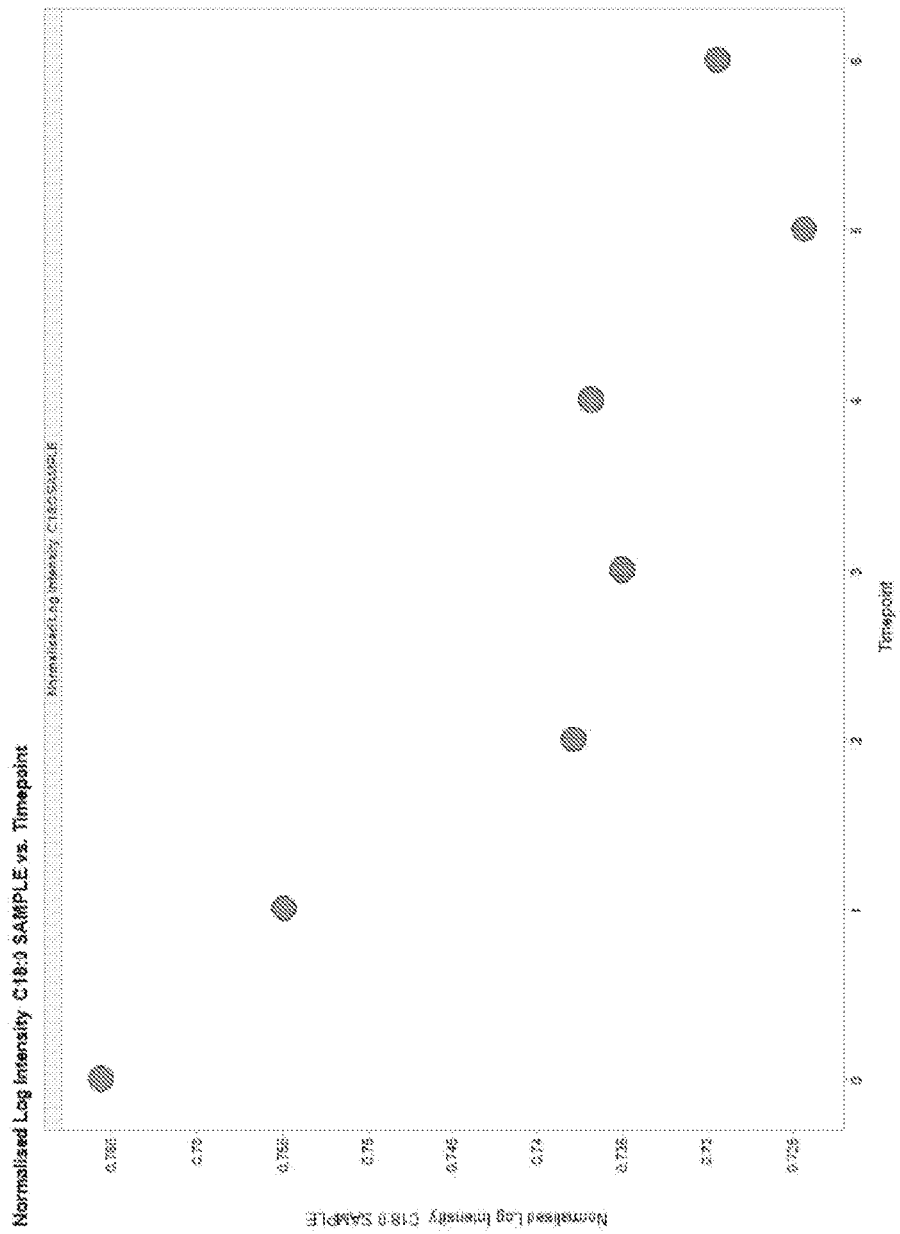
FIG. 21C. Ion intensity plot showing the changes in the level of glycine-$C_6$ sugar addition product over time during the production of a pet food.
Figure 21E:
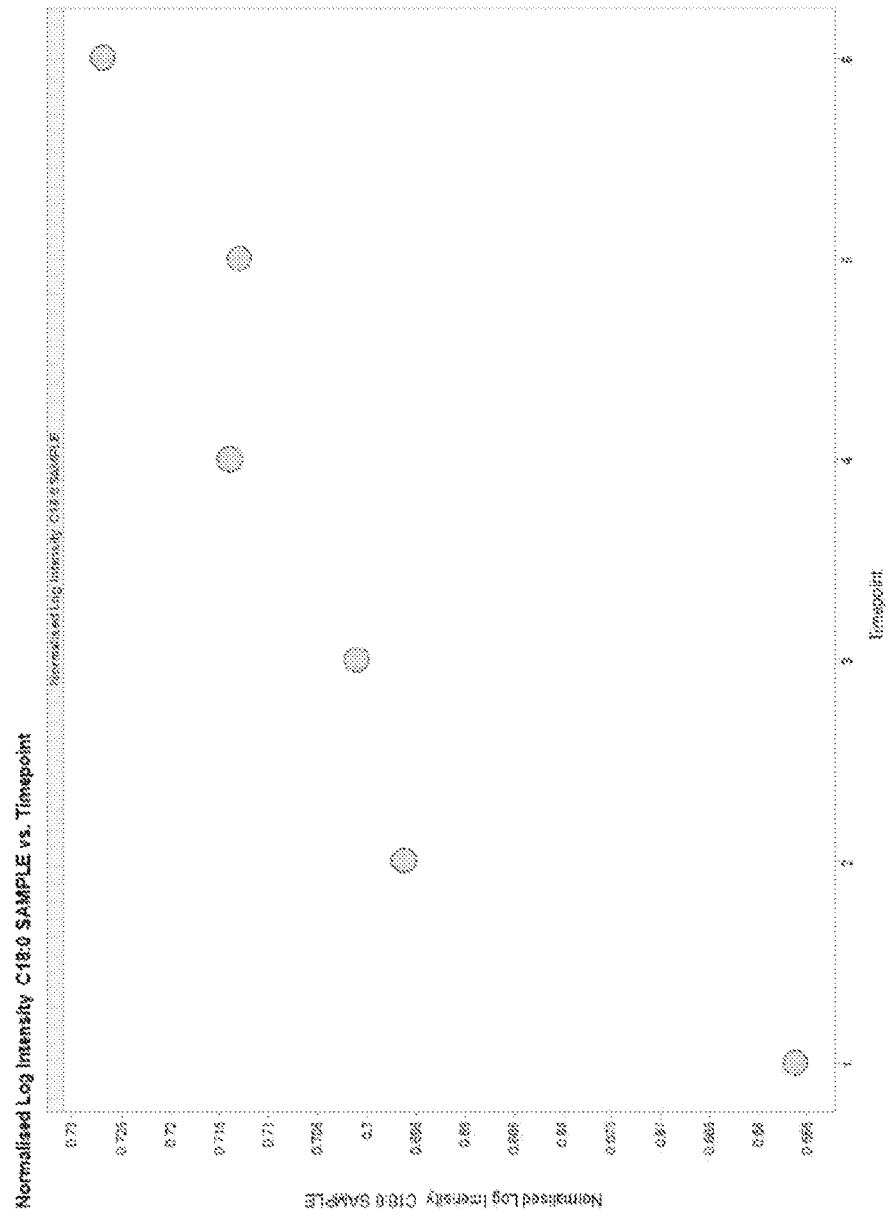
FIG. 21E. Ion intensity plot showing the changes in the level of glycine-$C_6$ Amadori product over time during the production of a pet food.
Figure 21F:
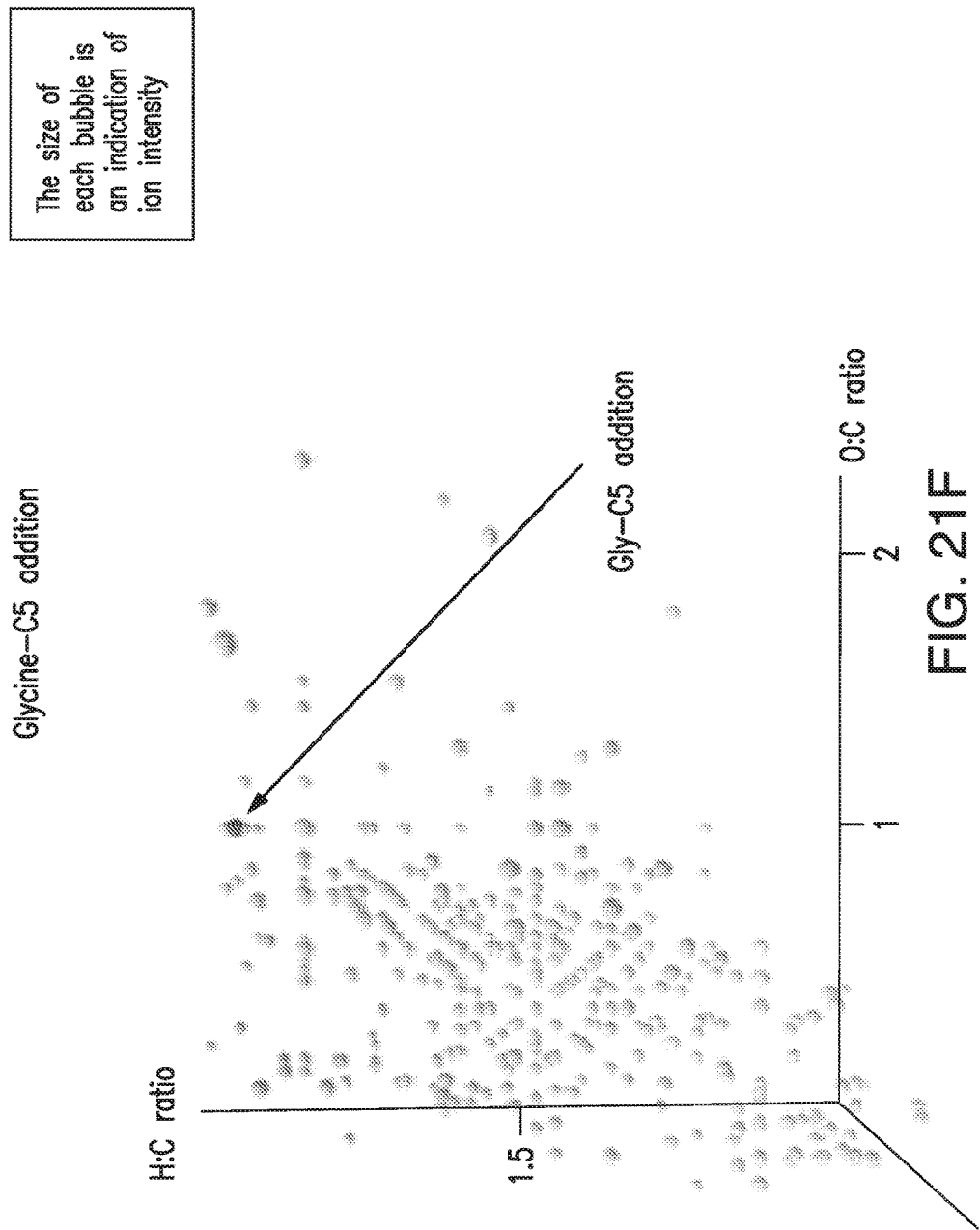
FIG. 21F. Van Krevelen diagram showing the presence of a glycine-$C_5$ addition product during the production of a pet food.
Figure 21G:
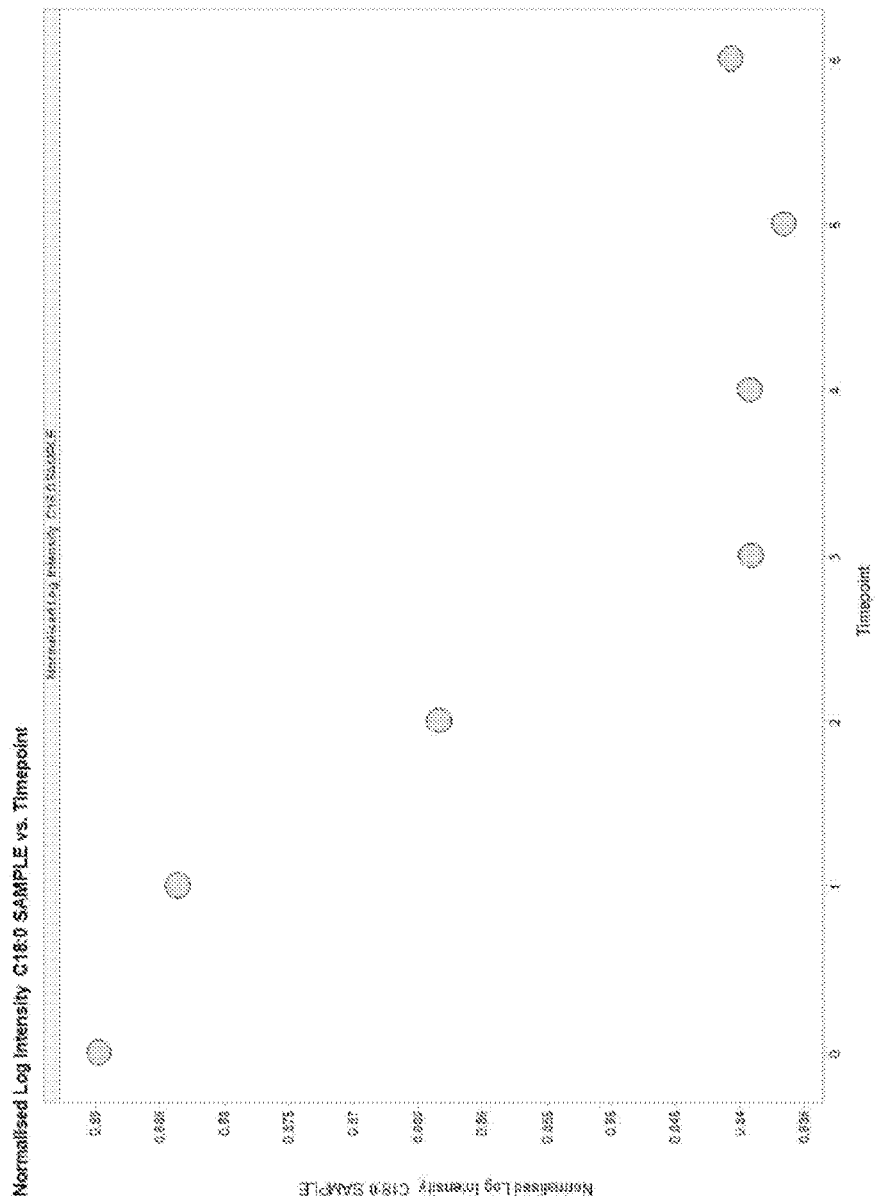
FIG. 21G. Ion intensity plot showing the changes in the level of glycine-$C_5$ addition product over time during the production of a pet food.
Figure 21H:
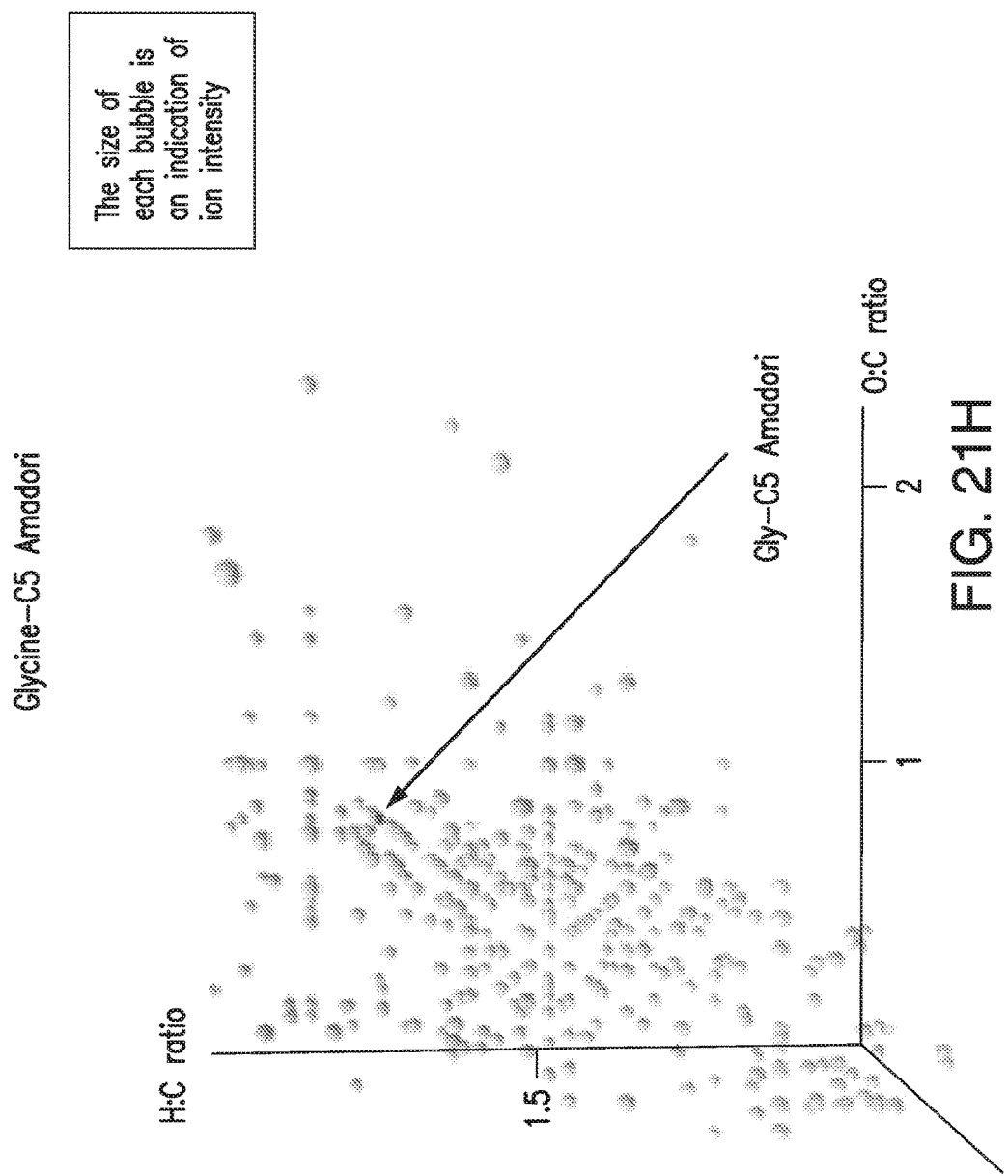
FIG. 21H. Van Krevelen diagram showing the presence of a glycine-$C_5$ Amadori product during the production of a pet food.
Figure 21I:
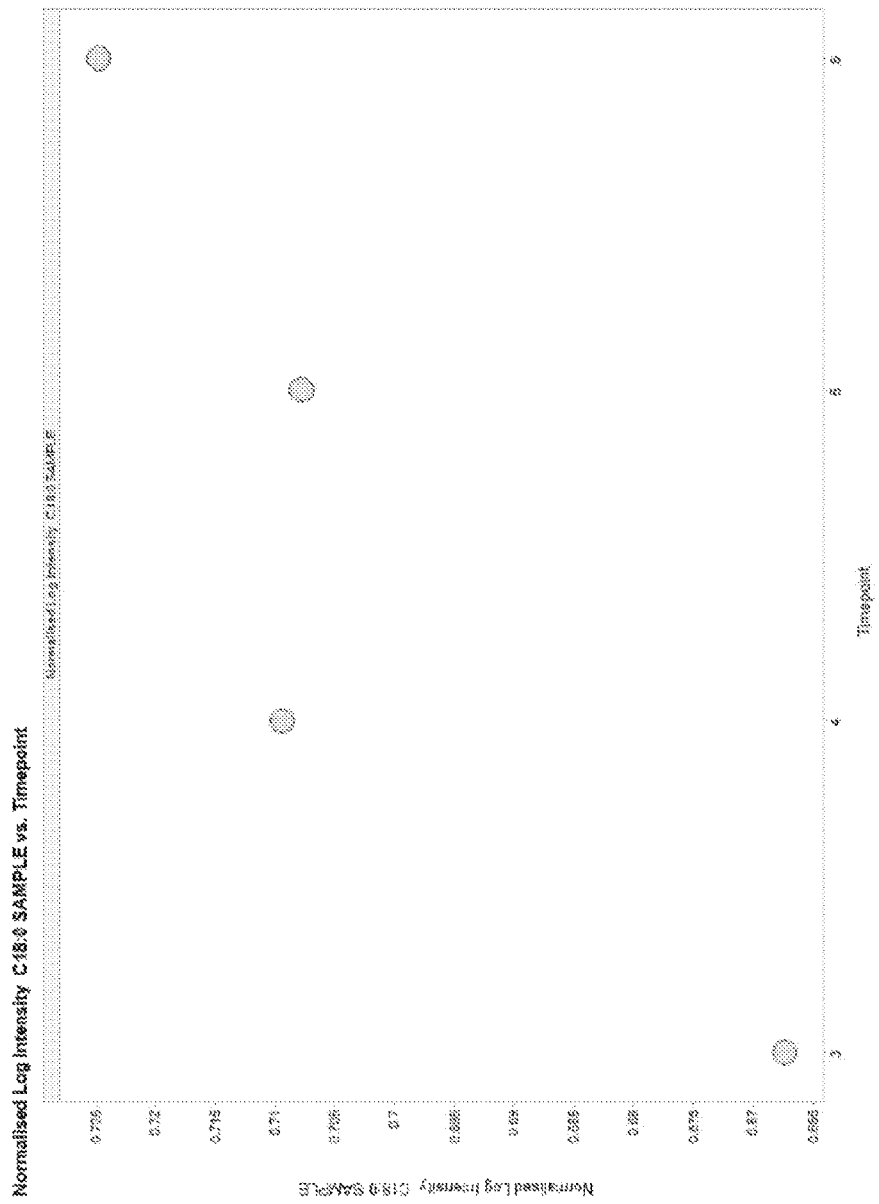
FIG. 21I. Ion intensity plot showing the changes in the level of glycine-$C_5$ Amadori product over time during the production of a pet food.
Figure 22:
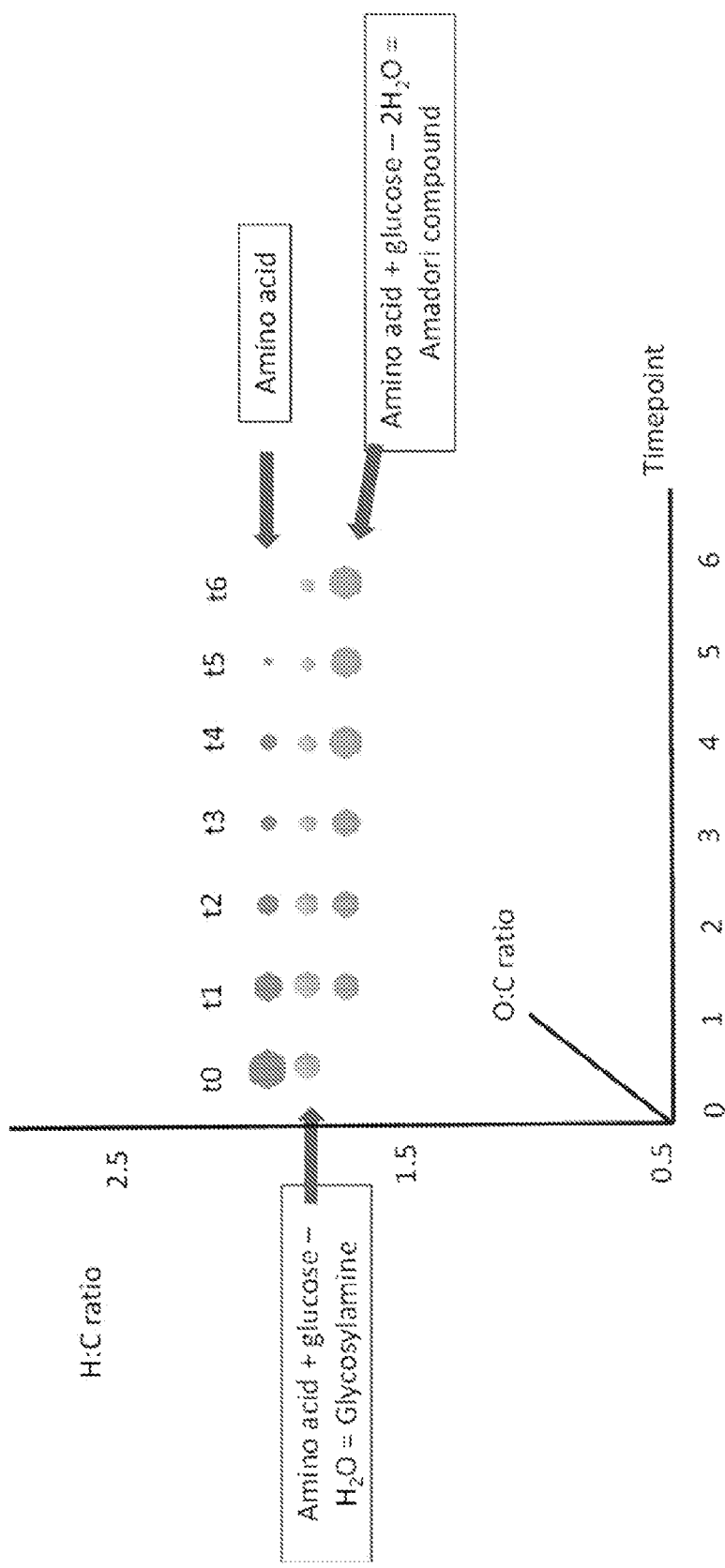
FIG. 22. Van Krevelen diagram showing the changes in levels of amino acids, glycosylamines, and Amadori products during thermal processing of a food product.

In FIG. 21A, the initial reaction between an amino acid (e.g., glycine) and a sugar (e.g. glucose) that occurs during a Maillard reaction is shown. FIG. 21B shows the chemical components that are present in a pet food product following a sterilization process. The presence of a glycine-$C_6$ sugar addition product, which is an intermediate of the Maillard reaction, was detected (arrows). The glycine-$C_6$ addition product is the result of an addition reaction and the mass of such the product is equal to the mass of glycine and glucose. Such a compound can be detected by predicting the chemical formula and mass of the compound and detecting one or more peaks within a mass spectrum from a sample that corresponds to the mass of the compound. As shown in FIG. 21C, the glycine-$C_6$ addition product decreased over time during the production of the pet food, indicating that it was being consumed in the Maillard reaction. Conversely, the glycine-$C_6$ Amadori product, which was present in the pet food product following the sterilization process (FIG. 21D) increased during the production of the pet food (FIG. 21E), indicating that it was being produced by the Maillard reaction. The glycine-$C_6$ Amadori product is the result of a dehydration reaction of the glycine-$C_6$ addition product and the mass of the glycine-$C_6$ Amadori product is equal to the glycine-$C_6$ addition product minus water. In addition, as shown in FIG. 21G, the presence of a glycine-$C_5$ addition product, which is another intermediate of the Maillard reaction, was detected. This reaction intermediate was consumed by the Maillard reaction during the production process (FIG. 21G); whereas, the Amadori product (FIG. 21H) of this glycine-$C_5$ addition product increased during the production of the pet food (FIG. 21I). FIG. 22 displays the levels of amino acids, glycosylamine compounds, and Amadori products over time on a single van Krevelen diagram. FIG. 22 shows that the level of amino acids decreased with time, while the level of the Amadori products increased. The level of glycosylamine compounds initially increased, presumably as amino acids reacted with sugars to form glycosylamine compounds. However, after $t_2$ the level of glycosylamine compounds decreased, presumably as the glycosylamine compounds were converted to Amadori compounds. These data show that Maillard reactions can be monitored and analyzed during the production of a pet food using uHRMS.

Figure 23:
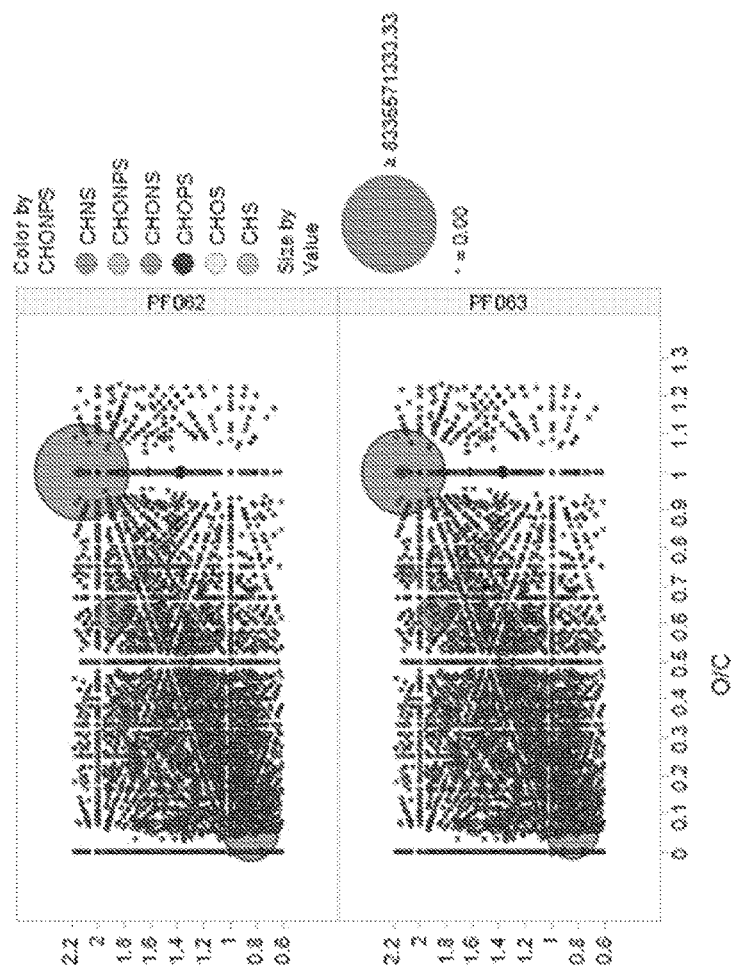
FIG. 23. Histograms and van Krevelen diagrams showing the total number of sulfur-containing compositions in two related food products, one with and one without chemical intervention.
Figure 23:
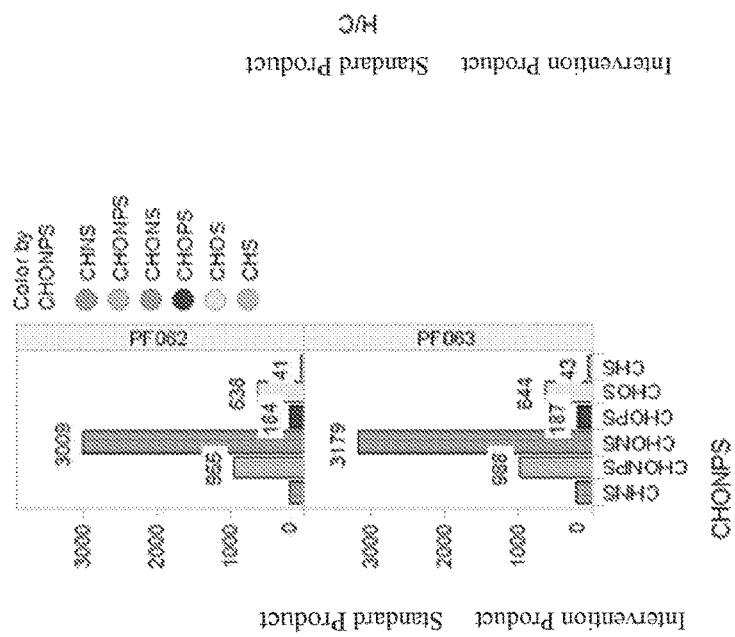
Figure 24:
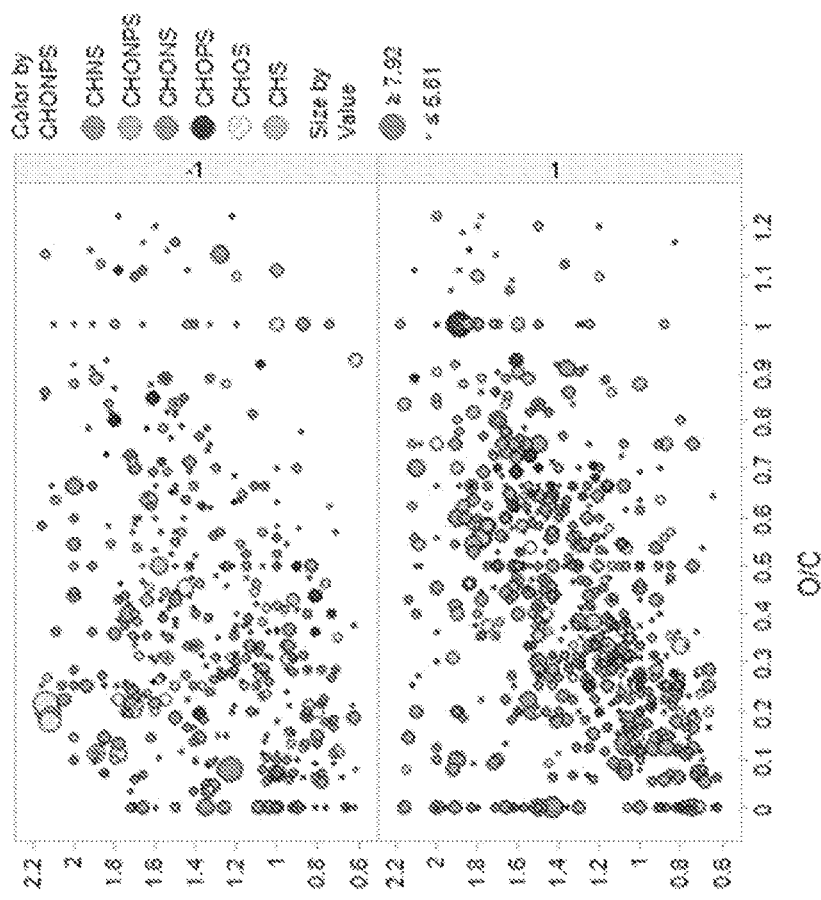
FIG. 24. Histograms and van Krevelen diagrams showing the number of unique sulfur-containing compositions as between the two food products of FIG. 23.
Figure 24:
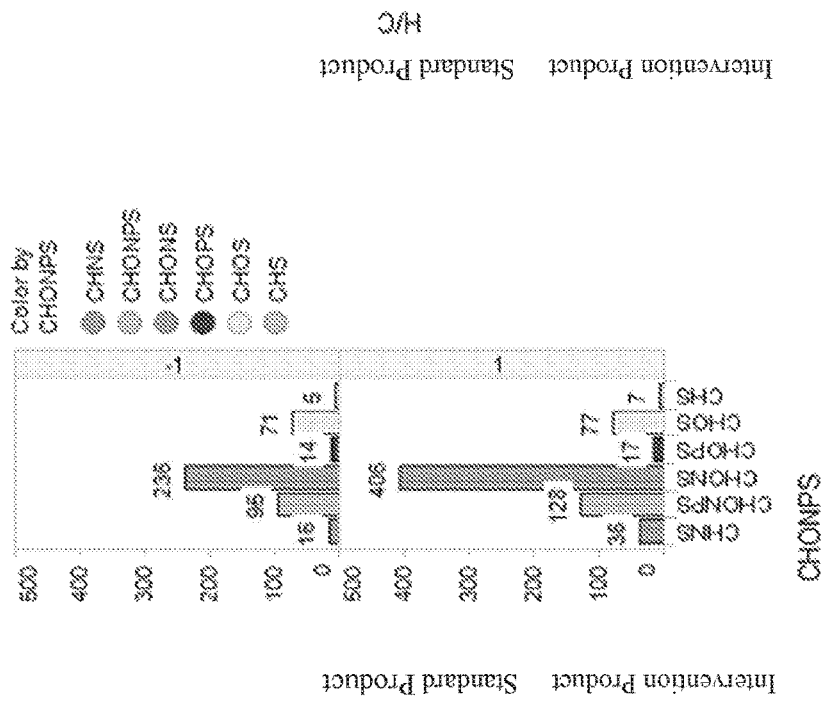

Additionally, Maillard reactions can be modulated based on results of uHRMS analysis and uHRMS can be used to validate the modulation of such reactions. For example, the raw materials of a pet food product can adjusted prior to thermal processing to alter the food product composition and chemical pathways. For example, one or more sulfur-containing amino acids can be added to a commercially available pet food ("standard product") to produce an "intervention product." After thermal processing, the compositions of the standard product and the intervention product can be compared using uHRMS. FIG. 23 displays the total number of sulfur-containing CHONSP elemental compositions (broken down by elemental composition) in each of the standard and intervention products, presented as histograms and van Krevelen diagrams. These data show that the addition of sulfur-containing amino acids to the intervention product, prior to thermal processing, increased the number of sulfur-containing compounds in the food product. Furthermore, applying additional filters can show an increase in the Maillard reaction chemical pathways for sulfur-containing amino acids. FIG. 24 displays the total number of sulfur-containing CHONSP elemental compositions unique to each of the standard and intervention products discussed in connection with FIG. 23, presented as histograms and van Krevelen diagrams. Although some sulfur-containing compounds are naturally present in the standard product, the intervention product had additional sulfur-containing compounds that were not also present in the standard product. For example, Maillard reaction products from sulfur-containing amino acids can have a CHONS elemental composition, and FIG. 24 shows that the number of compounds having this elemental composition was increased by the addition of the sulfur-containing amino acids to the intervention product.

Using these techniques, it is possible to accurately analyze and track which chemical compounds are generated and consumed during thermal processing, and to use this information to identify and manipulate the chemical reactions that occur during thermal processing. Additionally, these techniques can be preferable to certain isotopic labeling techniques, e.g., CAMOLA, where the addition of labels can accelerate or change chemical pathways and produce potentially inaccurate results. Furthermore, these data indicate that the chemical pathways and reaction products can be altered by adjusting the raw materials of a pet food product. Based on uHRMS analysis, it is possible to compare and adjust food product compositions. Alternatively, uHRMS can be used to test whether modulating the raw materials or processing techniques for a food product has the desired impact on final food product composition, for example by analyzing and comparing the amounts of chemical compounds in the food product, with and without modulation.

Example 5: Monitoring Product Consistency Using Ultra High Resolution Mass Spectrometry of Pet Food Products Analysis of uHRMS data can be used to identify and quantify changes in chemical composition between two samples of food products. For example, the accurate mass data obtained from uHRMS on one sample can be compared to the accurate mass data of another sample from the same production batch or a different production batch to monitor product consistency and provide quality control.

Figure 25:
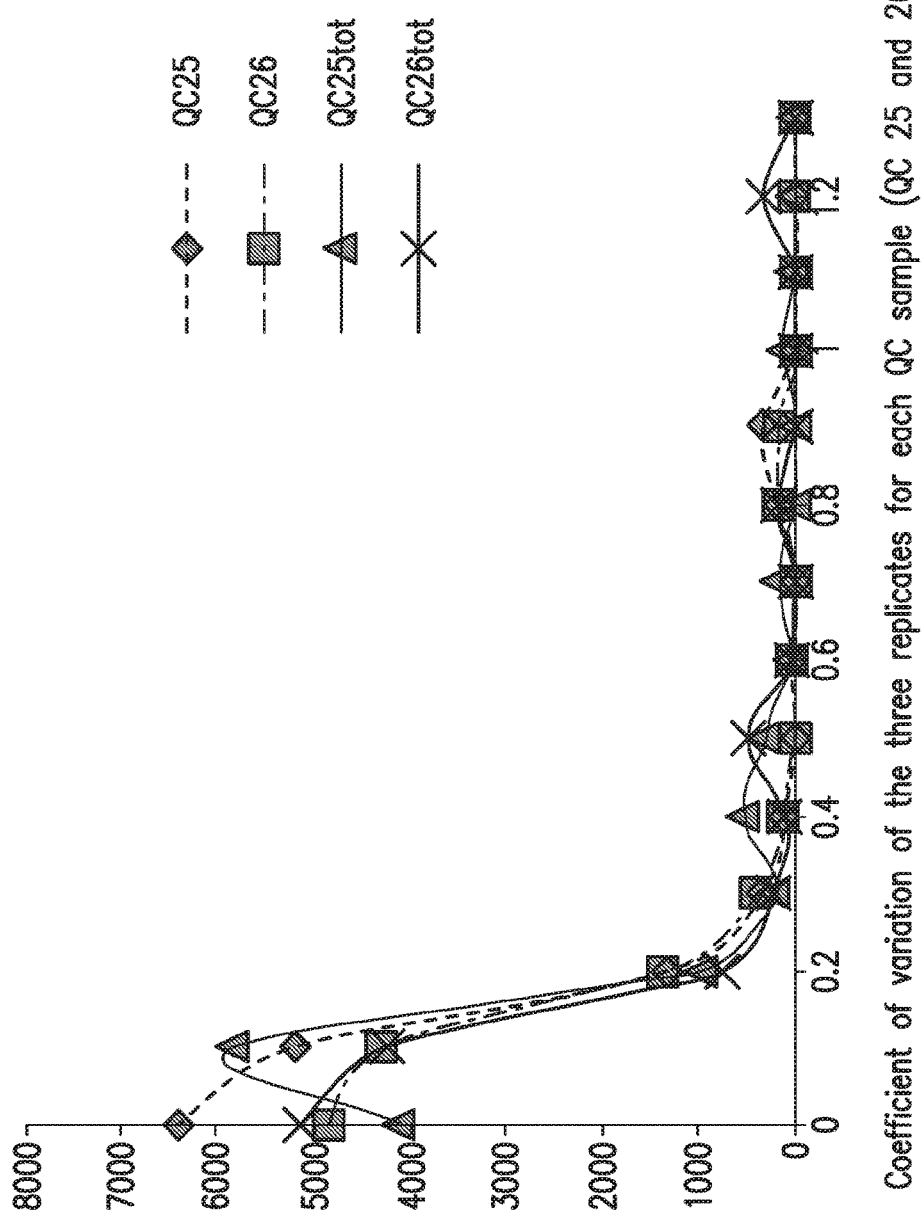
FIG. 25. Coefficients of variation of the accurate mass data across three runs of ultra high resolution mass spectrometry using two different food products. QC25 and QC26 represent one analysis per run and QC25tot and QC26tot represent 10 analyses per run.
Figure 26:
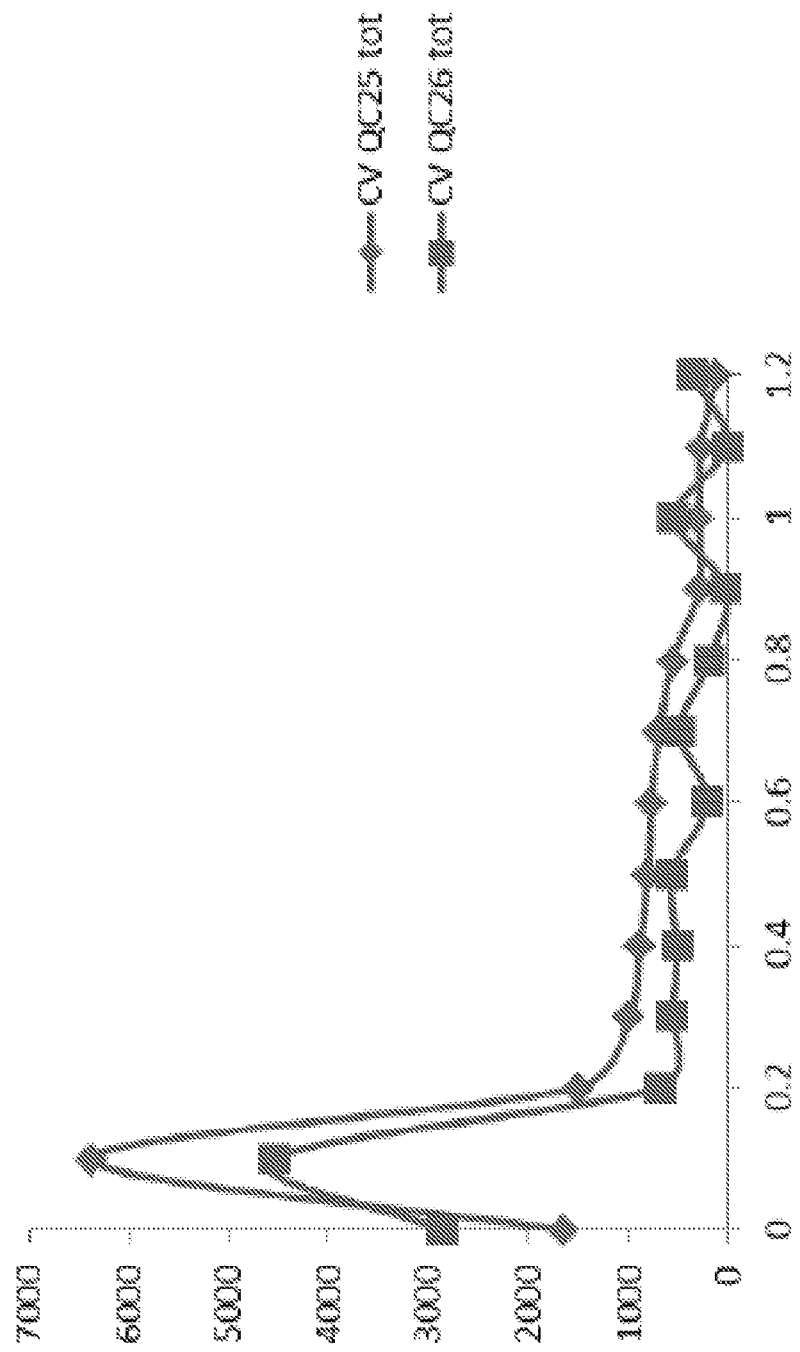
FIG. 26. Coefficients of variation of the accurate mass data across three runs of ultra high resolution mass spectrometry using the food products of FIG. 25, extracted and analyzed after approximately three months.

Comparison of uHRMS data from multiple runs of the same food product shows that the uHRMS data is highly reproducible. For example, FIG. 25 displays the coefficients of variation of samples of two food products (QC25 and QC26, each corresponding to a different pet food product). The coefficients of variation are calculated based on differences in the accurate mass data across the three runs. As shown in FIG. 25, both QC25 and QC26 had low coefficients of variation for most masses. For example, 90% of masses in QC25 and QC26 had coefficients of variation less than 0.2. Additionally, three uHRMS runs of the same food products, each with ten analyses of the samples, were performed. QC25tot and QC26tot correspond to QC25 and QC26, respectively. As shown in FIG. 25, both QC25tot and QC26tot likewise had low coefficients of variation for most masses. FIG. 26 displays the coefficients of variation across three runs of the same two food products (QC25tot and QC26tot), which were extracted and analyzed after approximately three months. Again, QC25tot and QC26tot showed low coefficients of variation for most masses across multiple runs.

These data show that uHRMS data is highly reproducible, and therefore can be used to monitor product consistency over time. For example, these techniques can be used to compare a sample taken from a one production batch (a "test sample") to a reference sample. The reference sample can be from another batch to ensure that product composition is similar. Alternatively, the reference sample can be a quality control sample to ensure that the batch meets quality control standards. The uHRMS of the reference sample can take place at the same time as the uHRMS of the test sample. Alternatively, the uHRMS data from the test sample can be compared to existing data on a reference sample. In this case, uHRMS can also be performed on a control sample that is the same composition as a sample used to create the existing data to ensure the consistency of the uHRMS analysis.

Example 6: Ionization Techniques for Ultra High Resolution Mass Spectrometry

Figure 27A:
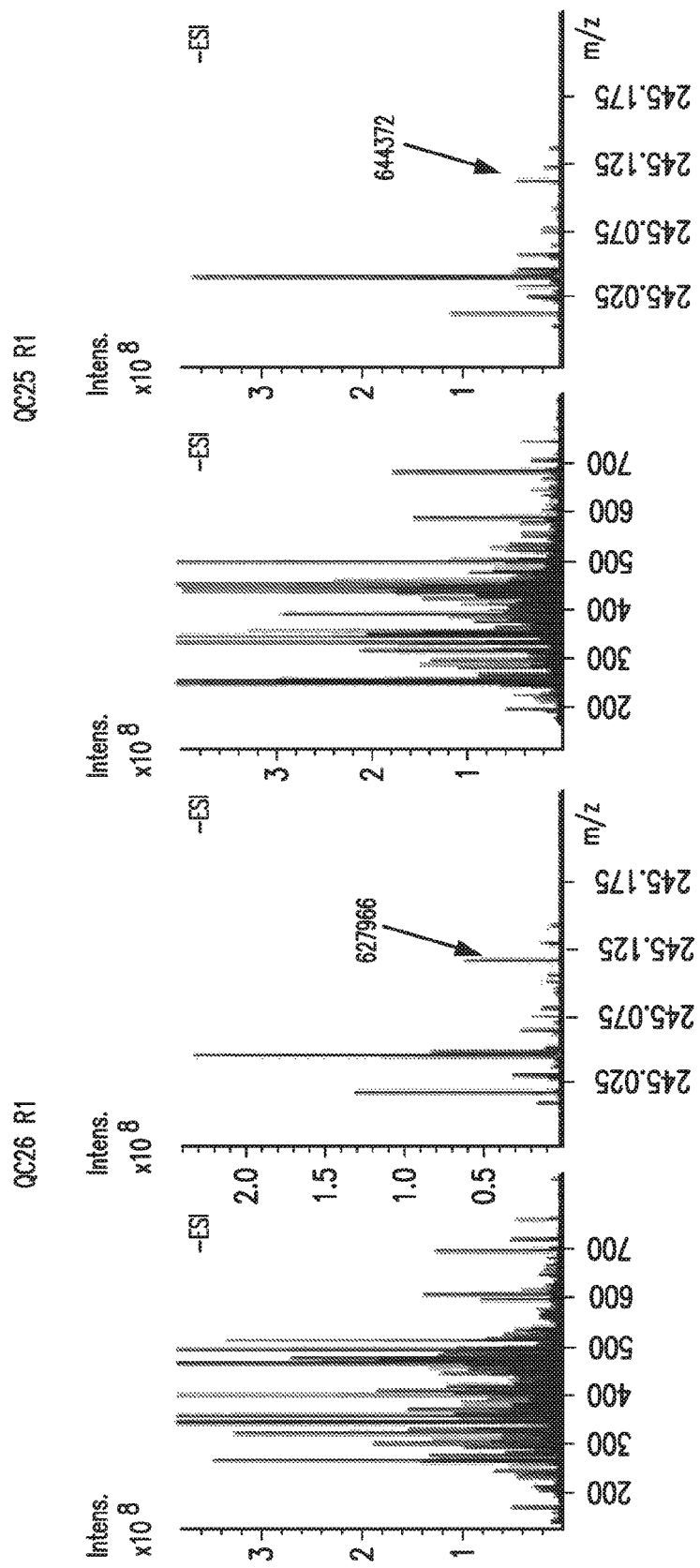
FIG. 27A. The mass spectra of samples acquired using negative ion mode ESI (−ESI).
Figure 27B:
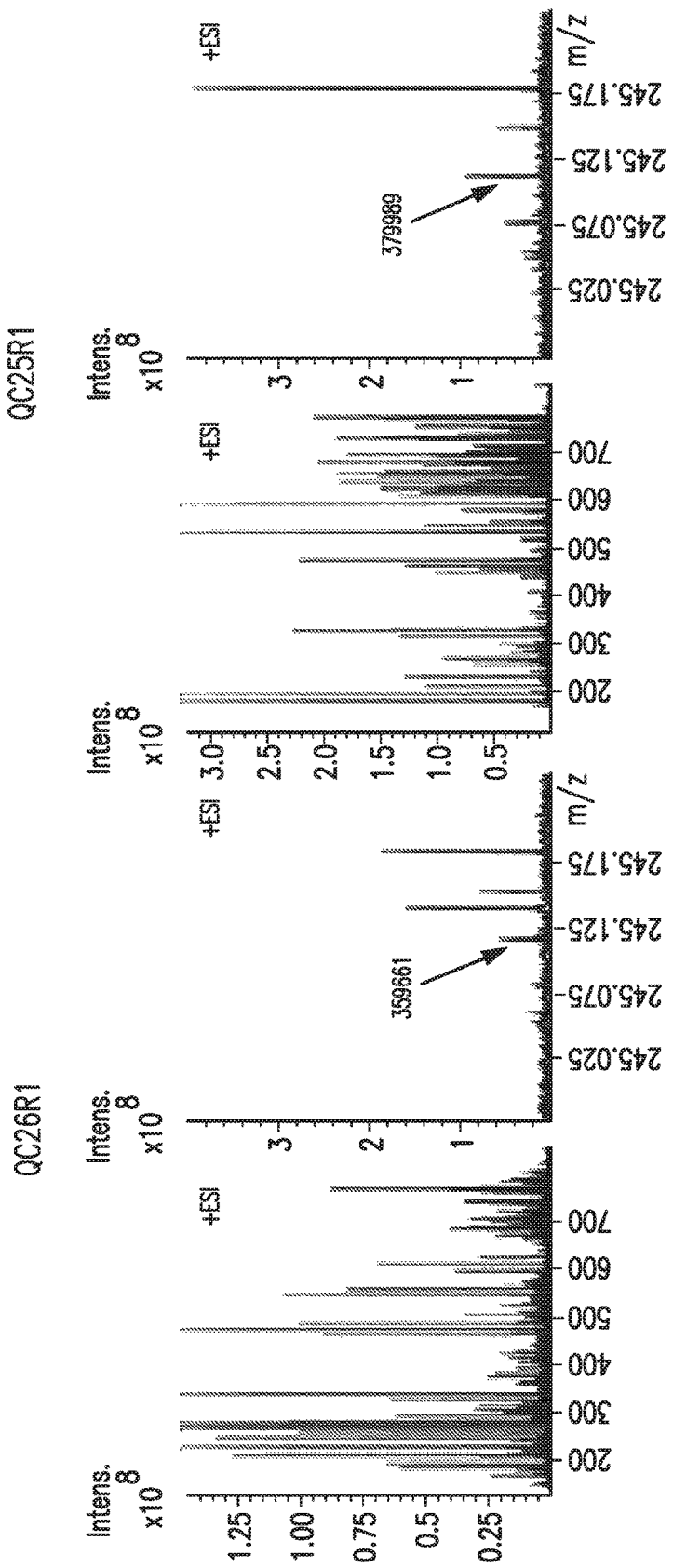
FIG. 27B. The mass spectra of samples acquired using positive ion mode ESI (+ESI).
Figure 27C:
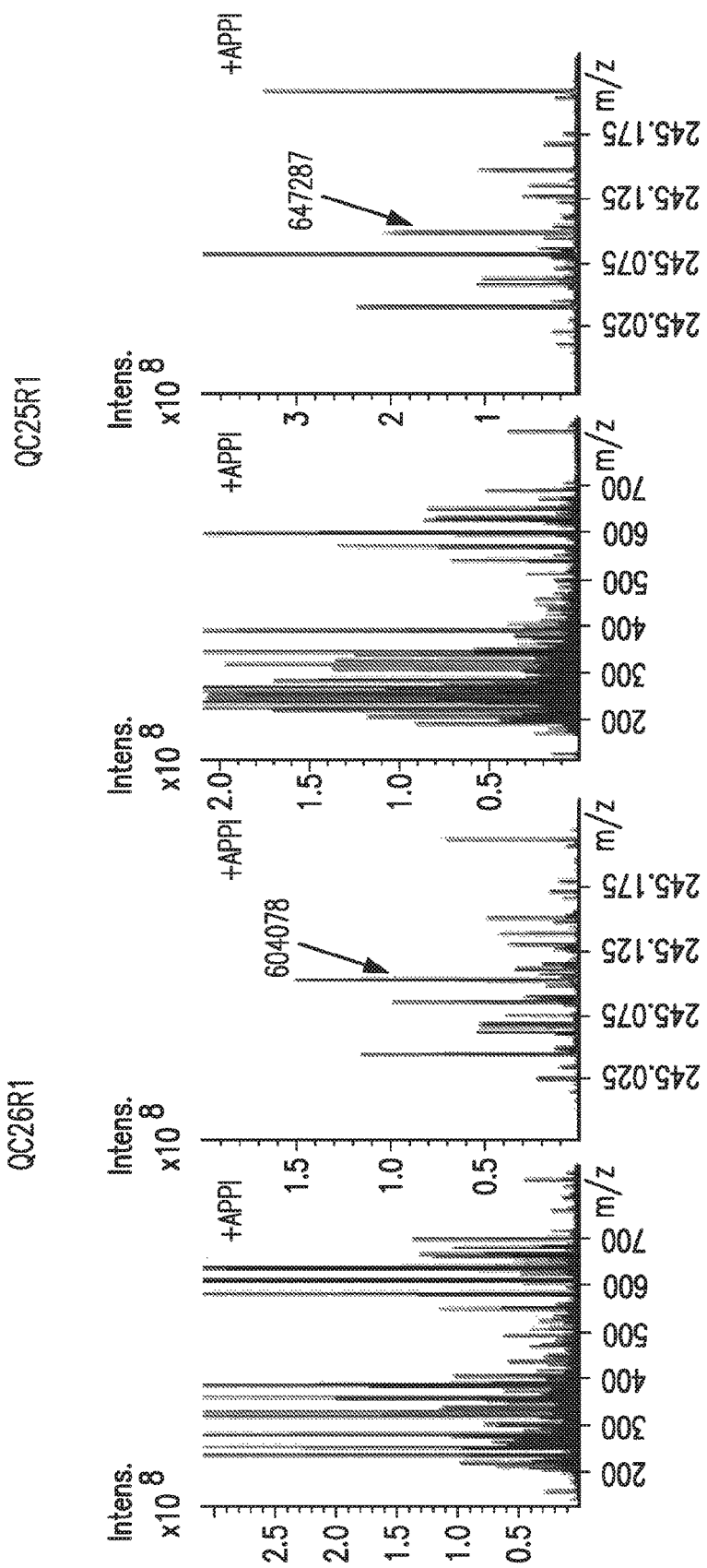
FIG. 27C. The mass spectra of samples acquired using Atmospheric Pressure Photo Ionization (APPI).
Figure 28:
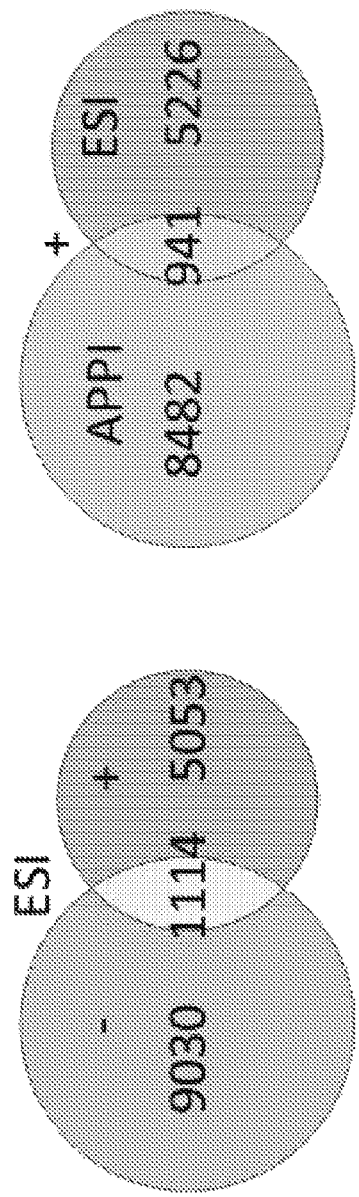
FIG. 28. The number of peaks and CHONSP elements identified after three different ionization techniques.
Figure 29A:
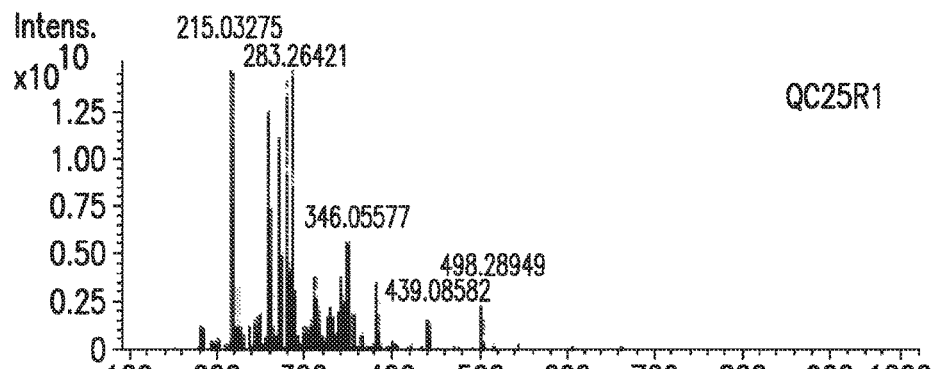
FIGS. 29A-29D. The mass spectra of samples prepared by volatile (above) and non-volatile extraction (below) methods.
Figure 29B:
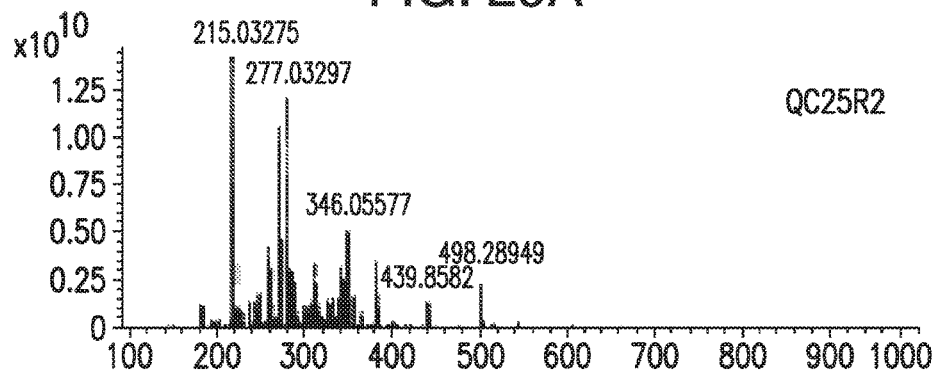
Figure 29C:
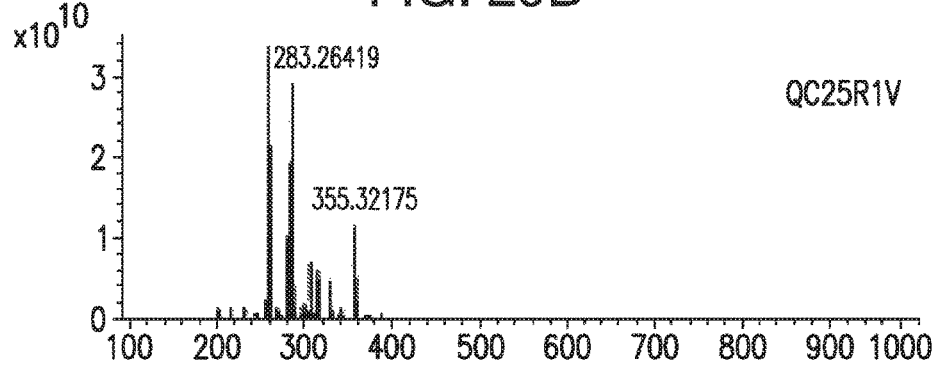
Figure 29D:
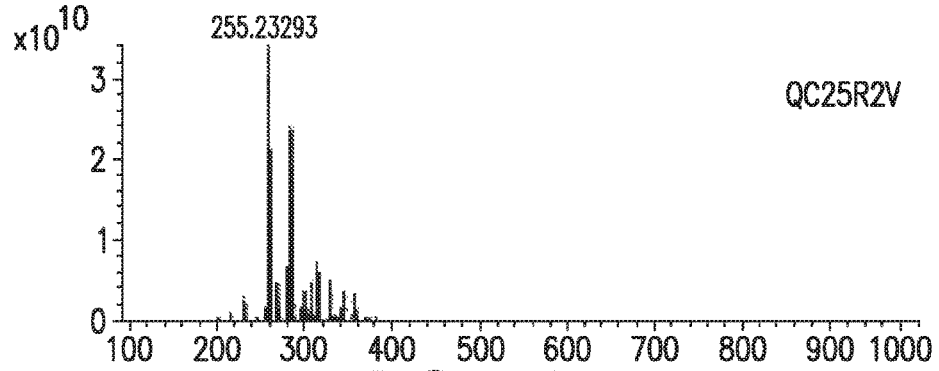
Figure 30A:
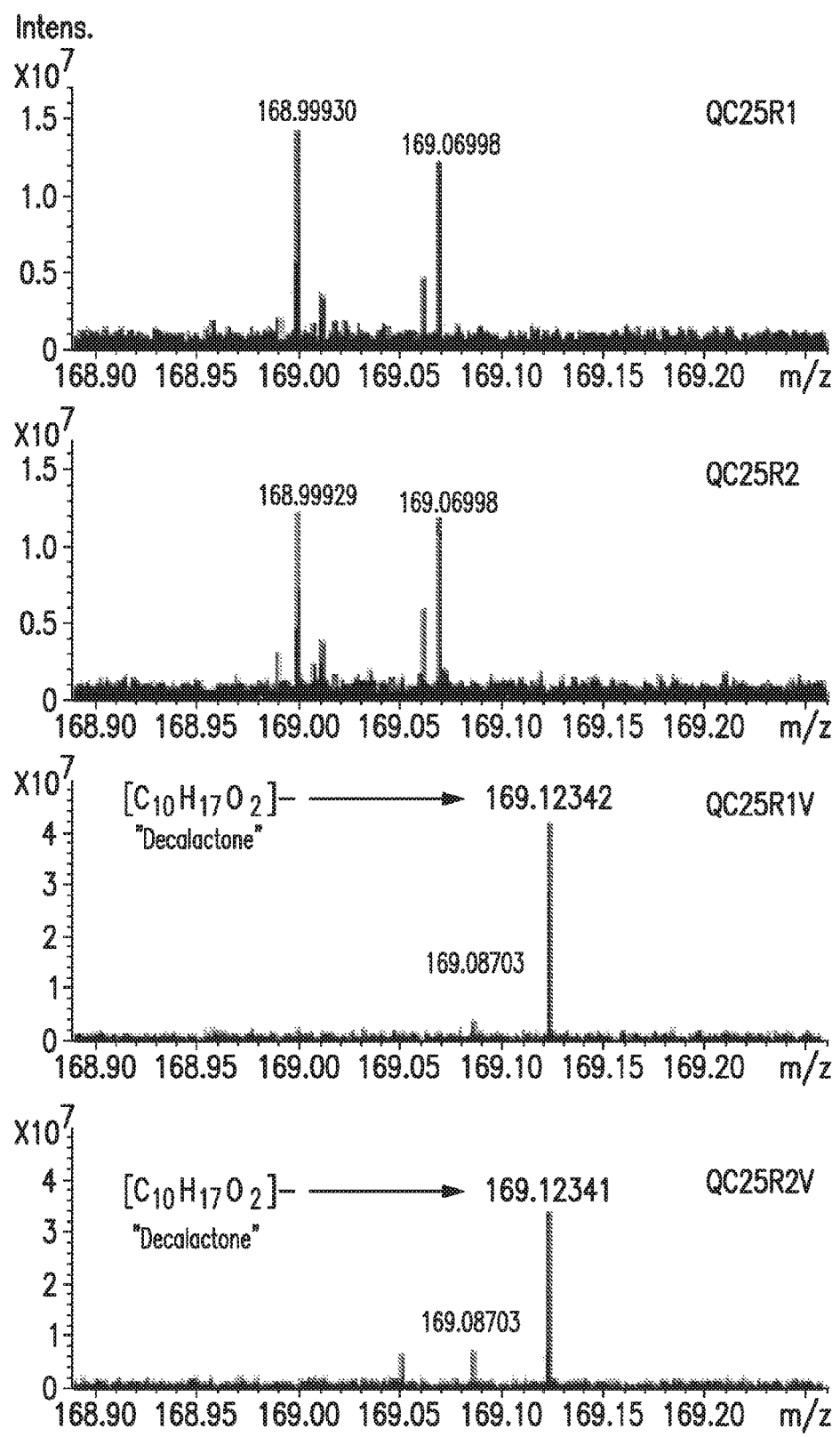
FIG. 30A. Mass spectra comparing levels of decalactone in samples prepared by volatile and non-volatile extraction methods.
Figure 30B:
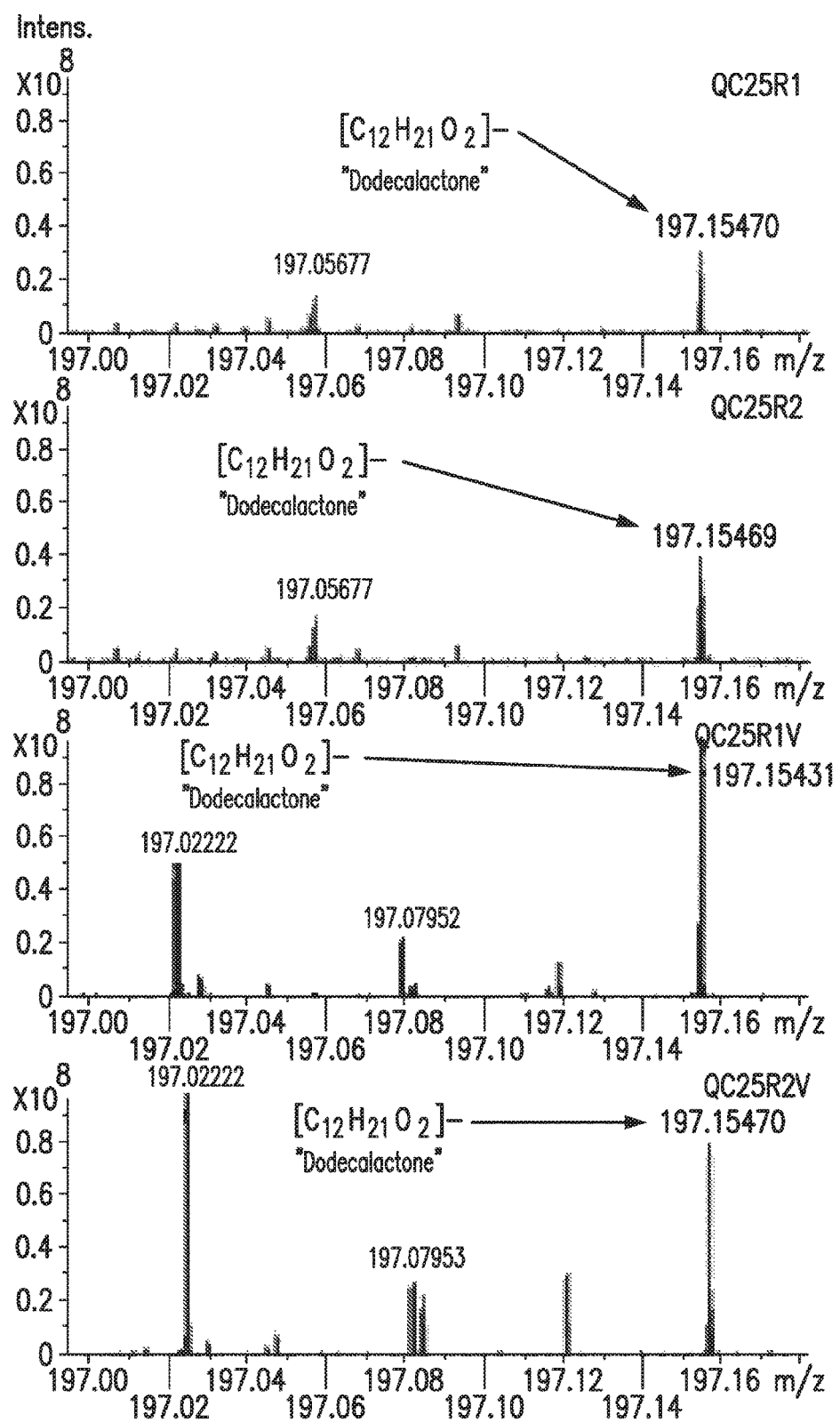
FIG. 30B. Mass spectra comparing levels of dodecalactone in samples prepared by volatile and non-volatile extraction methods.
Figure 30C:
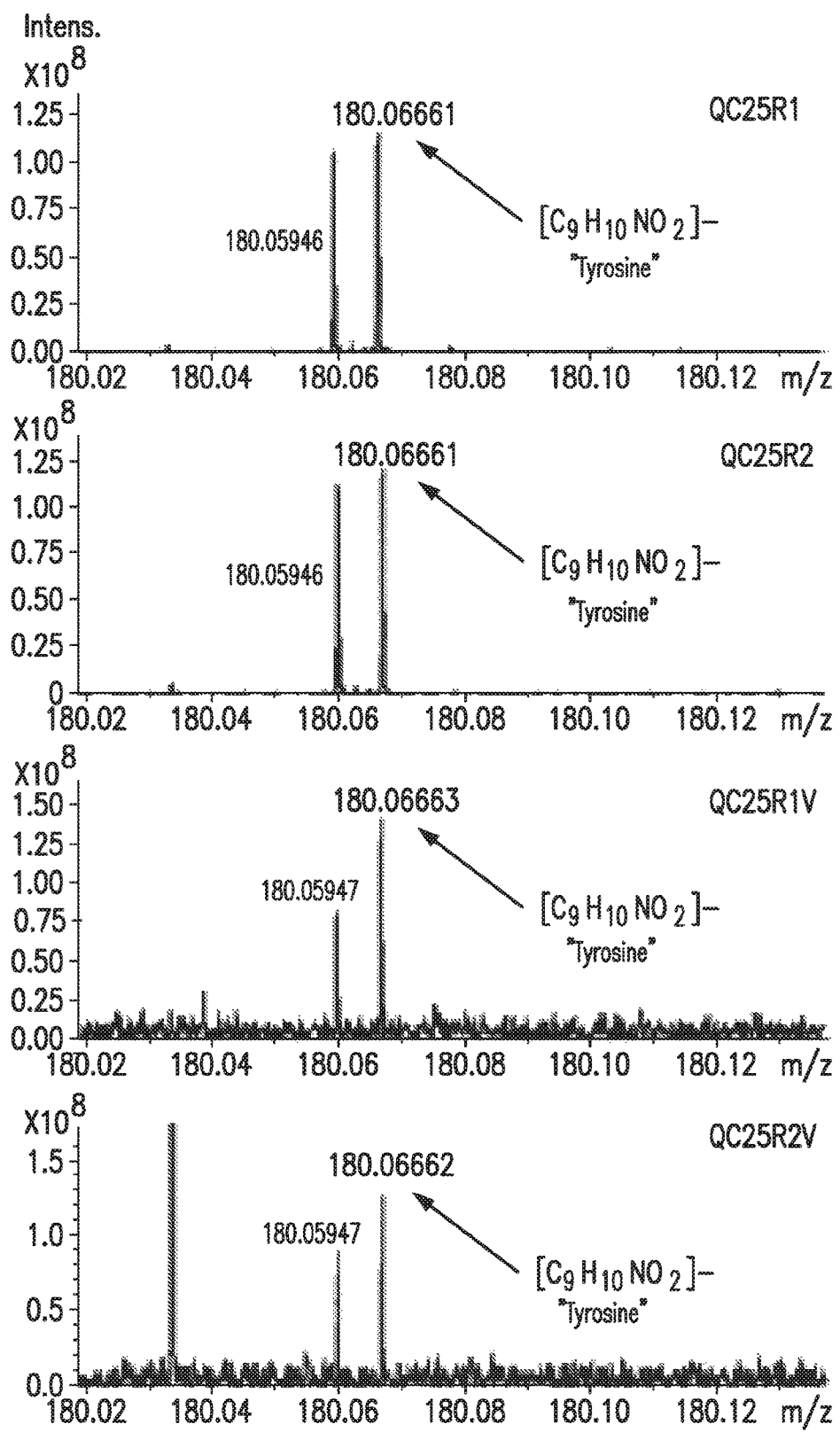
FIG. 30C. Mass spectra comparing levels of tyrosine in samples prepared by volatile and non-volatile extraction methods.
Figure 30D:
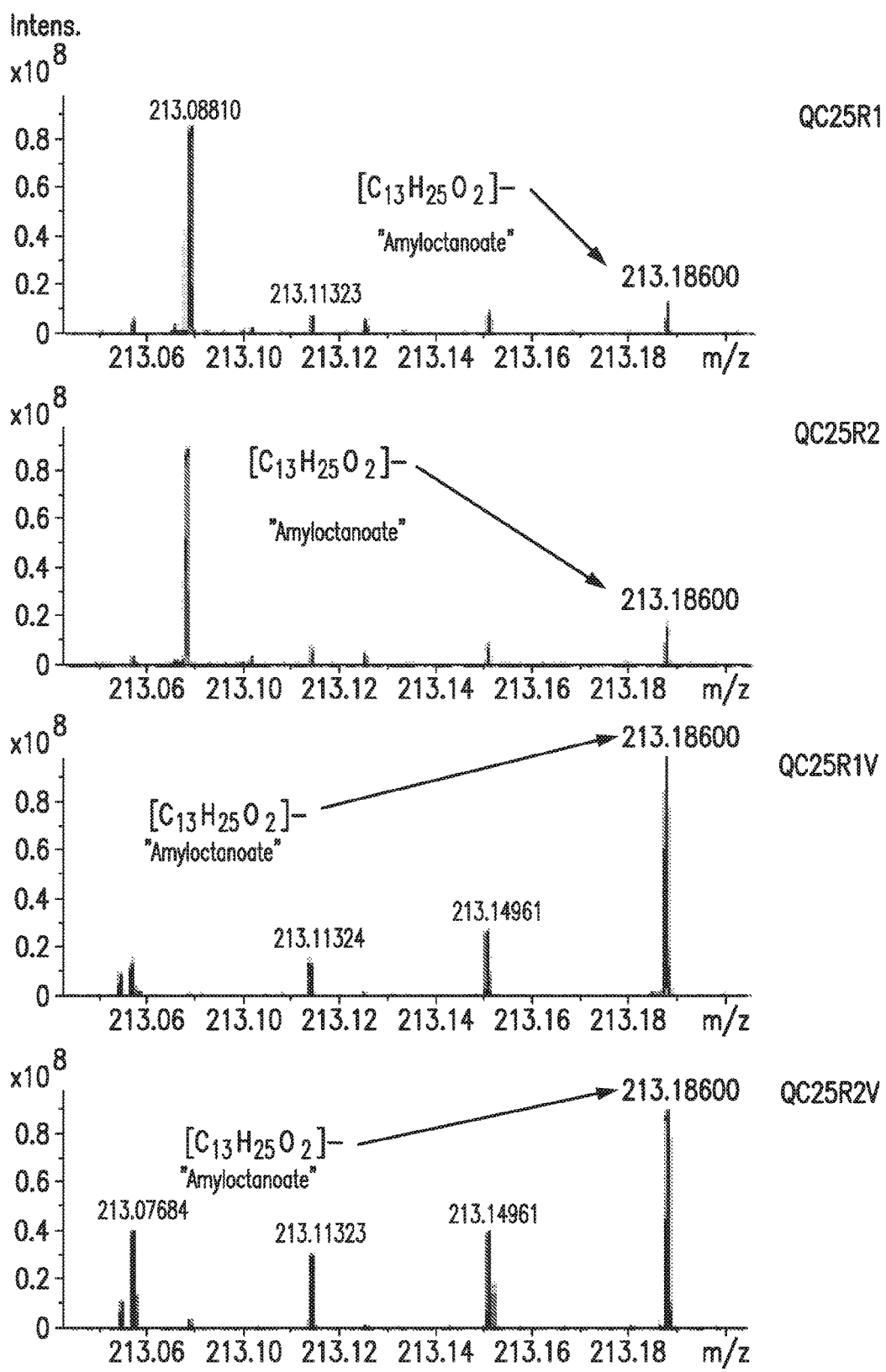
FIG. 30D. Mass spectra comparing levels of amyl octanoate in samples prepared by volatile and non-volatile extraction methods.

As previously discussed, various ionization techniques can be used prior to uHRMS analysis. In this example, two samples were subjected to three different methods of ionization, and then analyzed using uHRMS. FIGS. 27A, 27B, and 27C compare the mass spectra of two samples (QC26 and QC25) after each was subjected to negative ion mode ESI (−ESI), positive ion mode ESI (+ESI), and Atmospheric Pressure Photo Ionization (APPI), respectively. The mass spectra of the samples after each method of ionization show different peaks. FIG. 28 provides the number of mass spectra peaks and CHONSP elemental compositions identified after each method of ionization. FIG. 28 also shows two Venn diagrams depicting the overlap of CHONSP elemental compositions identified by each of the methods of ionization. The left Venn diagram compares the number of CHONSP elemental compositions identified after negative ion mode ESI, identified after positive ion mode ESI, and identified after both methods of ionization. The right Venn diagram provides the same comparison but of positive ion mode APPI versus positive ion mode ESI. These data show that using different ionization techniques can allow uHRMS to detect different chemical entities and classes of compounds in a complex mixture, and therefore using a combination of ionization modes, it is possible to extend the analytical coverage.

Example 7: Methods of Sample Extraction for Ultra High Resolution Mass Spectrometry Samples for use in uHRMS can be prepared using various extraction methods. The extraction method can be selected to concentrate the sample with certain classes of compounds. This example compares the uHRMS data of samples prepared by Solvent Assisted Flavor Evaporation (SAFE) distillation and methanolic extraction.

In this Example, the SAFE distillation was performed using the following exemplary method of SAFE distillation. Distilled ether (100 mL) was used to extract a sample of homogenized pet food (50.25 g) by shaking the mixture (30 min, ~450 ocs/min). The extracted sample was centrifuged (15 min, 5100 rpm, 4° C.). The supernatant was decanted into a measuring cylinder (104 mL). The solid sample was retained and washed a second time with distilled ether (50 mL), which was followed by shaking and centrifuging as described above. The supernatant was added to the measuring cylinder (for a total volume of 160 mL). The supernatant was dried with sodium sulfate (18.52 g, $Na_2SO_4$) and was filtered into a flask to create a sample. The SAFE apparatus was set up to achieve a stable vacuum ($1.34 \times 10^{-3}$ mbar) and the glassware was cooled with liquid nitrogen. A steady stream of the sample was introduced into the sample compartment of the SAFE apparatus. The stopper of the SAFE apparatus was removed just before the last of the sample was introduced to release the pressure (the vacuum was maintained below $2 \times 10^{-3}$ mbar throughout). A flask collected the SAFE extract. The flask was removed and frozen overnight. The extract was removed from the freezer and dried with $Na_2SO_4$ to remove any water. The extract was filtered into a fluted flask, which was submerged in a water bath (40° C.) and attached to a Vigreux column to concentrate the extract (2 mL).

SAFE distillation can create an extract that concentrates the volatile components of a food product or sample. FIG. 29 compares the mass spectra of two samples prepared by SAFE distillation (QC25R1V and QC25R2V) against the mass spectra of the same two samples prepared using methanolic extraction, i.e., a non-volatile extraction method, (QC25R1 and QC25R2). As shown by FIG. 29, the peaks of the samples prepared by the two extraction methods are different. FIG. 30 provides a comparison of other narrow mass spectra ranges of the same mass spectra presented in FIG. 29 to illustrate the concentration of volatile or non-volatile components in samples prepared by the two extraction methods. For example, in FIG. 30B there is less tyrosine (a non-volatile component) in the samples extracted by SAFE distillation compared to methanolic extraction. Conversely, in FIGS. 30A, 30C, and 30D, there is, respectively, more decalactone, dodecalactone, and amyl octanoate (volatile components) in the samples extracted by SAFE distillation compared the samples extracted by methanolic extraction.

Figure 31A:
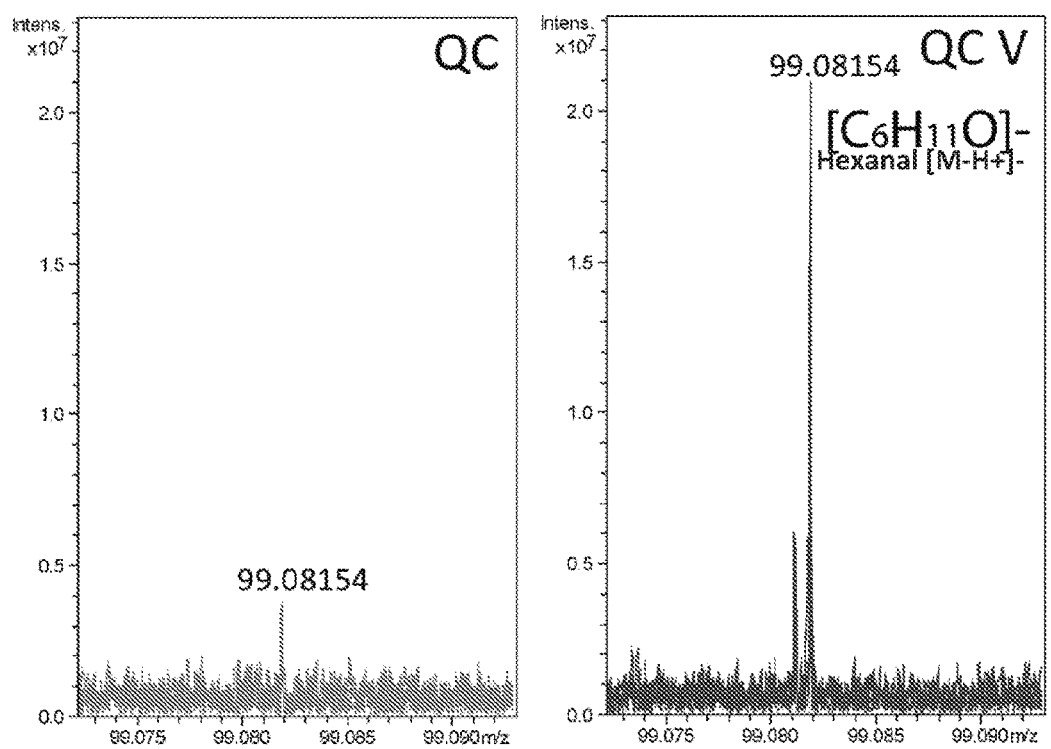
FIG. 31A. Mass spectra comparing levels of hexanal in samples prepared by volatile and non-volatile extraction methods. The peak on the mass spectra corresponds to the hexanal anion.
Figure 31B:
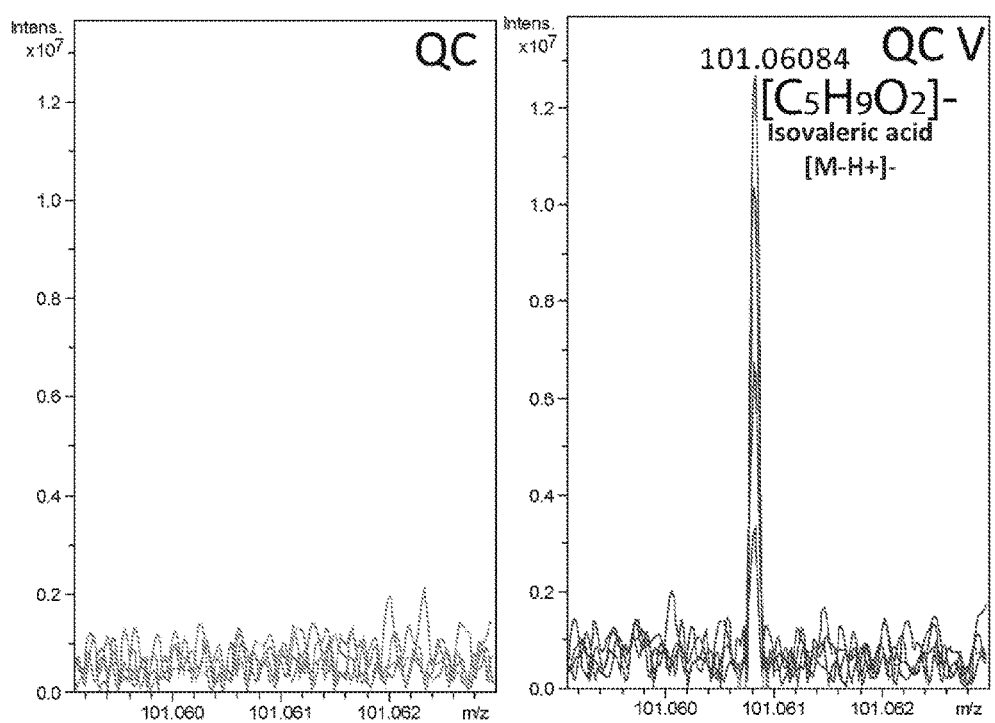
FIG. 31B. Mass spectra comparing levels of isovaleric acid in samples prepared by volatile and non-volatile extraction methods. The peak on the mass spectra corresponds to the isovaleric acid anion.

FIG. 31 compares the mass spectra of two sample extracts, a first which was prepared by SAFE distillation (QCV), and a second which was prepared by a non-volatile extraction method (QC). As shown in FIG. 31A, the sample prepared by a non-volatile extraction method contained less hexanal (a volatile component) compared to the sample prepared by SAFE distillation. In FIG. 31A, the peak corresponds to the hexanal anion, and not the neutral molecule. Similarly, as shown in FIG. 31B, the sample prepared by a non-volatile extraction method likewise contained less isovaleric acid (a volatile component). In FIG. 31B, the peak corresponds to the isovaleric acid anion, and not the neutral molecule. These data illustrate that various extraction methods can be used to concentrate certain components or classes of chemical compounds for uHRMS analysis.

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods or steps.

Patents, patent applications, publications, product descriptions and protocols are cited throughout this application the disclosures of which are incorporated herein by reference in their entireties for all purposes.

What we claim is:

1. A method for reducing an amount of a compound within a complex mixture, comprising:
    a) providing a first sample and a second sample of the complex mixture, wherein the first sample is obtained prior to the second sample, and wherein the first sample and the second sample are obtained during a process of producing the complex mixture;
    b) performing mass spectrometry on the first sample using an ultra high resolution mass spectrometer to obtain a first mass spectrum;
    c) performing mass spectrometry on the second sample using an ultra high resolution mass spectrometer to obtain a second mass spectrum;
    d) comparing one or more peaks of the first mass spectrum corresponding to the compound to one or more peaks of the second mass spectrum corresponding to the compound to determine an amount of the compound within the second sample as compared to an amount of the compound in the first sample; and
    e) modulating the process of producing the complex mixture to reduce the amount of the compound in the complex mixture,
    wherein modulating the process of producing the complex mixture comprises varying one or more of temperature, pressure, process time, flow rate, stoichiometry, concentration of one or more process components, or altering chemical reactions that consume or produce the compound.

2. The method of claim 1, further comprising analyzing a reduction of the compound within the complex mixture.

3. The method of claim 1, wherein the compound is a toxic compound, vitamin degradation product, nutrient, peptide, pro-oxidant, flavor compound, impurity and combinations thereof.

4. The method of claim 1, further comprising identifying an occurrence of one or more chemical reactions that consumes or produces the compound by identifying a second compound that differs by a specific mass.

5. The method of claim 4, wherein modulating the process of producing the complex mixture comprises altering one or more of the chemical reactions that consumes or produces the compound.

6. The method of claim 1, wherein modulating the process of producing the complex mixture comprises either increasing or decreasing a process temperature.

7. The method of claim 1, wherein the first sample and/or the second sample is prepared by a single alcohol/water extraction step.

8. The method of claim 1, wherein the first sample and/or the second sample is prepared by a single methanol/water extraction step.

9. The method of claim 1, wherein the first sample and the second sample are obtained from two different production batches of the complex mixture.

10. The method of claim 1, wherein at least one of the first sample and the second sample is a reference sample comprising a known composition.

11. The method of claim 1, wherein the one or more peaks from the first mass spectrum and the second mass spectrum corresponding to the compound corresponds to a reaction product or a degradation product of the compound.

12. The method of claim 1, wherein the compound corresponds to a raw material used to prepare the complex mixture.

13. The method of claim 1, wherein the ultra high resolution mass spectrometer is a Fourier transform ion cyclotron resonance mass spectrometer.

14. The method of claim 1, wherein the complex mixture comprises a food product.

15. The method of claim 14, wherein the food product is selected from the group consisting of a pet food product, a chocolate product, a candy product, a gum product and combinations thereof.

16. The method of claim 1, wherein the amount of the compound in the complex mixture corresponds to a level of lipid oxidation during the process of producing the complex mixture.

17. The method of claim 1, wherein the amount of the compound in the complex mixture corresponds to a level of protein hydrolysis during the process of producing the complex mixture.

18. A method for increasing an amount of a compound within a complex mixture, comprising:
  a) providing a first sample and a second sample of the complex mixture, wherein the first sample is obtained prior to the second sample, and wherein the first sample and the second samples are obtained during a process of producing the complex mixture;
  b) performing mass spectrometry on the first sample using an ultra high resolution mass spectrometer to obtain a first mass spectrum;
  c) performing mass spectrometry on the second sample using an ultra high resolution mass spectrometer to obtain a second mass spectrum;
  d) comparing one or more peaks of the first mass spectrum corresponding to the compound to one or more peaks of the second mass spectrum corresponding to the compound to determine an amount of the compound within the second sample as compared to an amount of the compound in the first sample; and
  e) modulating the process of producing the complex mixture to increase the amount of the compound in the complex mixture,
  wherein modulating the process of producing the complex mixture comprises varying one or more of temperature, pressure, process time, flow rate, stoichiometry, concentration of one or more process components, or altering chemical reactions that consume or produce the compound.

19. The method of claim 18, further comprising analyzing an increase of the compound within the complex mixture.

20. The method of claim 18, wherein the compound comprises a flavor compound, nutrient, vitamin, degradation product, peptide, mineral, antioxidant, product of a Maillard reaction and combinations thereof.

21. The method of claim 20, wherein the nutrient is selected from the group consisting of a Vitamin B compound, thiamine, riboflavin, a Vitamin A compound, retinol, an essential amino acid and combinations thereof.

22. A method for altering a level of fermentation of cocoa beans comprising:
  a) providing a first sample and a second sample of fermented cocoa beans, wherein the first sample is obtained prior to the second sample, and wherein the first sample and the second sample are obtained during a cocoa bean fermentation process;
  b) performing mass spectrometry on the first sample using an ultra high resolution mass spectrometer to obtain a first mass spectrum;
  c) performing mass spectrometry on the second sample using an ultra high resolution mass spectrometer to obtain a second mass spectrum;
  d) comparing one or more peaks of the first mass spectrum corresponding to a cocoa bean fermentation product to one or more peaks of the second mass spectrum corresponding to the cocoa bean fermentation product to determine a level of cocoa bean fermentation; and
  e) modulating the cocoa bean fermentation process to alter the level of fermentation of cocoa beans,
  wherein modulating the cocoa bean fermentation process comprises varying one or more of temperature, pressure, process time, flow rate, stoichiometry, or concentration of one or more process components.

23. The method of claim 22, wherein the cocoa bean fermentation product is a sugar molecule, fat molecule, peptide, protein, flavor precursor compound or combinations thereof.

24. A method for modulating an amount of a target compound within a complex mixture, comprising:
  a) providing a first sample and a second sample of the complex mixture, wherein the first sample is obtained prior to the second sample, and wherein the first sample and the second sample are obtained during a process of producing the complex mixture;
  b) performing mass spectrometry on the first sample using an ultra high resolution mass spectrometer to obtain a first mass spectrum;
  c) performing mass spectrometry on the second sample using an ultra high resolution mass spectrometer to obtain a second mass spectrum;
  d) comparing one or more peaks of the first mass spectrum corresponding to an intermediate compound that is a precursor to the target compound to one or more peaks of the second mass spectrum corresponding to the intermediate compound to determine an amount of the intermediate compound within the second sample as compared to an amount of the intermediate compound in the first sample; and
  e) modulating the process of producing the complex mixture to increase or decrease an amount of the intermediate compound in the complex mixture, thereby modulating the amount of the target compound, wherein modulating the process of producing the complex mixture comprises varying one or more of temperature, pressure, process time, flow rate, stoichiometry, concentration of one or more process components, or altering chemical reactions that consume or produce the intermediate compound.

25. The method of claim 24, further comprising analyzing a change of the amount of the intermediate compound within the complex mixture.

26. The method of claim 24, wherein the intermediate compound is a precursor of the target compound, and
wherein the target compound is selected from the group consisting of a flavor compound, nutrient, vitamin, degradation product, peptide, mineral, antioxidant, product of a Maillard reaction, and combinations thereof.

27. The method of claim 24, wherein the intermediate compound is a precursor of the target compound, and
wherein the target compound is selected from the group consisting of a toxic compound, vitamin degradation product, nutrient, peptide, pro-oxidant, flavor compound, impurity, and combinations thereof.

28. The method of claim 24, further comprising identifying an occurrence of one or more chemical reactions that consumes or produces the intermediate compound by identifying a second compound that differs by a specific mass.

29. The method of claim 28, wherein modulating the process comprises altering the one or more chemical reactions that consume or produce the intermediate compound.

30. The method of claim 24, wherein modulating the process comprises either increasing or decreasing a process temperature.

31. The method of claim 24, wherein the one or more peaks from the first mass spectrum and the second mass spectrum corresponding to the intermediate compound corresponds to a reaction product or a degradation product of the target compound.

32. The method of claim 24, wherein the intermediate compound corresponds to a raw material used to prepare the complex mixture.

33. The method of claim 24, wherein the amount of the target compound in the complex mixture corresponds to a level of lipid oxidation during the process of producing the complex mixture.

34. The method of claim 24, wherein the amount of the target compound in the complex mixture corresponds to a level of protein hydrolysis during the process of producing the complex mixture.

35. A method for adjusting an amount of a target compound within a complex mixture, comprising:
a) providing a first sample of the complex mixture, wherein the first sample is obtained during a process of producing the complex mixture;
b) performing mass spectrometry on the first sample of the complex mixture using an ultra high resolution mass spectrometer to obtain a first mass spectrum;
c) adding a precursor to the target compound to the complex mixture during the process of producing the complex mixture to obtain an intervention complex mixture;
d) providing a second sample from the intervention complex mixture, wherein the second sample is obtained during the process of producing the complex mixture;
e) performing mass spectrometry on the second sample of the intervention complex mixture using an ultra high resolution mass spectrometer to obtain a second mass spectrum;
f) comparing one or more peaks of the first mass spectrum corresponding to the target compound to one or more peaks of the second mass spectrum corresponding to the target compound to determine an amount of the target compound within the second sample as compared to the amount of the target compound in the first sample; and
g) modulating an amount of the precursor added to the complex mixture during the process of producing the complex mixture to modulate the amount of the target compound in the complex mixture.

36. The method of claim 35, further comprising analyzing a change of the amount of the target compound within the complex mixture.

37. The method of claim 35, wherein the method further comprises either increasing or decreasing a process temperature during the process of producing the complex mixture.

38. The method of claim 35, wherein the target compound is nutritional.

39. The method of claim 38, wherein the target compound is a trace metal.

40. The method of claim 35, wherein the target compound comprises sulfur.

41. The method of claim 35, wherein the precursor corresponds to a raw material used to prepare the complex mixture.

* * * * *